US012004959B2

(12) United States Patent
Collazo

(10) Patent No.: US 12,004,959 B2
(45) Date of Patent: Jun. 11, 2024

(54) HINGE KNEE PREPARATION INSTRUMENTATION AND ASSOCIATED METHODS

(71) Applicant: Howmedica Osteonics Corp., Mahwah, NJ (US)

(72) Inventor: Carlos E. Collazo, Old Greenwich, CT (US)

(73) Assignee: Howmedica Osteonics Corp., Mahwah, NJ (US)

( * ) Notice: Subject to any disclaimer, the term of this patent is extended or adjusted under 35 U.S.C. 154(b) by 948 days.

(21) Appl. No.: 16/904,667

(22) Filed: Jun. 18, 2020

(65) Prior Publication Data

US 2020/0315806 A1    Oct. 8, 2020

Related U.S. Application Data

(63) Continuation of application No. 15/637,619, filed on Jun. 29, 2017, now Pat. No. 10,722,372.

(Continued)

(51) Int. Cl.
*A61F 2/38* (2006.01)
*A61B 17/15* (2006.01)
(Continued)

(52) U.S. Cl.
CPC .......... *A61F 2/3854* (2013.01); *A61B 17/155* (2013.01); *A61F 2/30721* (2013.01);
(Continued)

(58) Field of Classification Search
None
See application file for complete search history.

(56) References Cited

U.S. PATENT DOCUMENTS

| 3,837,009 A | 9/1974 | Walker |
| 4,136,405 A | 1/1979 | Pastrick et al. |

(Continued)

FOREIGN PATENT DOCUMENTS

| DE | 2901009 A1 | 7/1980 |
| DE | 3343606 A1 | 7/1985 |

(Continued)

OTHER PUBLICATIONS

Biomet Orthopedics Inc., Resurfacing Distal Femur, OSS, Orthopaedic Salvage System, 2003.

(Continued)

*Primary Examiner* — Brian A Dukert
*Assistant Examiner* — Melissa A Hoban
(74) *Attorney, Agent, or Firm* — Lerner David LLP

(57) ABSTRACT

A hinge knee system includes a tibial assembly having a baseplate component and an axle component. The baseplate component has an opening that extends therein from a proximal end toward a distal end thereof. The axle component has a shaft portion receivable within the opening of the baseplate component and an axle connected to the shaft portion that extends in a direction transverse to a longitudinal axis of the shaft portion. The system also includes a femoral assembly that includes a distal femoral component. The distal femoral component includes condylar portions and an intercondylar portion disposed between the condylar portions. The intercondylar portion includes a bearing surface that defines a recess configured to rotatably receive the axle for articulation therewith.

17 Claims, 46 Drawing Sheets

Related U.S. Application Data

(60) Provisional application No. 62/358,222, filed on Jul. 5, 2016.

(51) Int. Cl.
  *A61F 2/30* (2006.01)
  *A61F 2/46* (2006.01)
  *A61B 17/17* (2006.01)

(52) U.S. Cl.
  CPC ............ *A61F 2/3836* (2013.01); *A61F 2/385* (2013.01); *A61F 2/4684* (2013.01); *A61B 17/157* (2013.01); *A61B 17/1764* (2013.01)

(56) References Cited

U.S. PATENT DOCUMENTS

| | | | |
|---|---|---|---|
| 4,219,893 A | 9/1980 | Noiles | |
| 4,262,368 A | 4/1981 | Lacey | |
| 4,301,553 A | 11/1981 | Noiles | |
| 4,358,859 A | 11/1982 | Schurman et al. | |
| 4,985,037 A * | 1/1991 | Petersen | A61F 2/3859 623/20.15 |
| 5,011,496 A | 4/1991 | Forte et al. | |
| 5,133,760 A * | 7/1992 | Petersen | A61F 2/38 623/20.36 |
| 5,358,527 A | 10/1994 | Forte | |
| 5,370,701 A | 12/1994 | Finn | |
| 5,413,607 A | 5/1995 | Engelbrecht et al. | |
| 5,569,263 A | 10/1996 | Hein | |
| 5,702,460 A * | 12/1997 | Carls | A61B 17/1764 623/20.14 |
| 5,733,292 A | 3/1998 | Gustilo et al. | |
| 5,766,257 A | 6/1998 | Goodman et al. | |
| 5,800,552 A | 9/1998 | Forte | |
| 5,824,096 A | 10/1998 | Pappas et al. | |
| 5,954,770 A | 9/1999 | Schmotzer et al. | |
| 6,013,103 A | 1/2000 | Kaufman et al. | |
| 6,447,549 B1 | 9/2002 | Taft | |
| 6,719,800 B2 | 4/2004 | Meyers et al. | |
| 6,962,607 B2 | 11/2005 | Gundlapalli et al. | |
| 7,387,644 B2 | 6/2008 | Beynnon et al. | |
| 7,497,874 B1 * | 3/2009 | Metzger | A61F 2/38 623/20.15 |
| 7,572,292 B2 | 8/2009 | Crabtree et al. | |
| 7,591,855 B2 | 9/2009 | Keller | |
| 7,658,767 B2 | 2/2010 | Wyss | |
| 7,695,520 B2 | 4/2010 | Metzger et al. | |
| 7,708,782 B2 | 5/2010 | Burstein et al. | |
| 7,871,442 B2 | 1/2011 | Servidio | |
| 7,918,893 B2 | 4/2011 | Romeis et al. | |
| 7,998,218 B1 | 8/2011 | Brown | |
| 8,163,028 B2 | 4/2012 | Metzger et al. | |
| 8,268,006 B2 | 9/2012 | Meyers et al. | |
| 8,328,873 B2 | 12/2012 | Metzger et al. | |
| 8,382,848 B2 | 2/2013 | Ries et al. | |
| 8,523,950 B2 | 9/2013 | Dees et al. | |
| 8,545,570 B2 | 10/2013 | Crabtree et al. | |
| 8,545,571 B2 | 10/2013 | Collazo et al. | |
| 8,568,485 B2 | 10/2013 | Ries et al. | |
| 8,617,250 B2 | 12/2013 | Metzger | |
| 8,628,579 B2 | 1/2014 | Ries et al. | |
| 9,011,444 B2 | 4/2015 | Primiano et al. | |
| 9,149,282 B2 | 10/2015 | Servidio et al. | |
| 9,283,081 B2 | 3/2016 | Bartels et al. | |
| 2003/0171815 A1 | 9/2003 | Kana et al. | |
| 2004/0249467 A1 | 12/2004 | Meyers et al. | |
| 2005/0246028 A1 | 11/2005 | Pappas et al. | |
| 2006/0041317 A1 | 2/2006 | Hazebrouck et al. | |
| 2006/0167554 A1 | 7/2006 | Heck et al. | |
| 2009/0125114 A1 * | 5/2009 | May | A61F 2/38 623/20.14 |
| 2009/0149964 A1 * | 6/2009 | May | A61F 2/30721 623/20.29 |
| 2010/0174378 A1 | 7/2010 | Metzger et al. | |
| 2011/0270403 A1 | 11/2011 | Ries et al. | |
| 2012/0271427 A1 | 10/2012 | Serafin, Jr. et al. | |
| 2012/0330430 A1 | 12/2012 | Meyers et al. | |
| 2013/0190883 A1 | 7/2013 | Collard et al. | |
| 2013/0325135 A1 | 12/2013 | Crabtree, Jr. et al. | |
| 2014/0025172 A1 | 1/2014 | Lucas et al. | |
| 2014/0025174 A1 | 1/2014 | Lucas et al. | |
| 2014/0114318 A1 | 4/2014 | May et al. | |
| 2014/0277567 A1 | 9/2014 | Collazo et al. | |
| 2016/0199101 A1 * | 7/2016 | Sharifi-Mehr | A61B 17/7002 606/258 |
| 2016/0199187 A1 | 7/2016 | Krebs et al. | |
| 2017/0035572 A1 | 2/2017 | Servidio | |

FOREIGN PATENT DOCUMENTS

| | | |
|---|---|---|
| DE | 202012004128 U1 | 7/2012 |
| EP | 0716839 A1 | 6/1996 |
| EP | 0724868 A1 | 8/1996 |
| FR | 2760352 A1 | 9/1998 |
| FR | 2980104 B1 | 12/2013 |
| WO | 03059203 A1 | 7/2003 |
| WO | 2013003433 A1 | 1/2013 |

OTHER PUBLICATIONS

DePuy Companies of Johnson & Johnson, S-ROM NOILES Surgical Technique, 2011.
European Search Report in EP16182774, dated Jan. 4, 2017, 3 pages.
Extended European Search Report for Application No. EP 19161155.7 dated Jul. 1, 2019.
Extended European Search Report for EP 17 17 9706 dated Sep. 18, 2017.
Stryker Howmedica Osteonics, Modular Roating Hinge Knee System, 2000.
Zimmer® NexGen® Rotating Hinge Knee Primary/Revision, 2002.

* cited by examiner

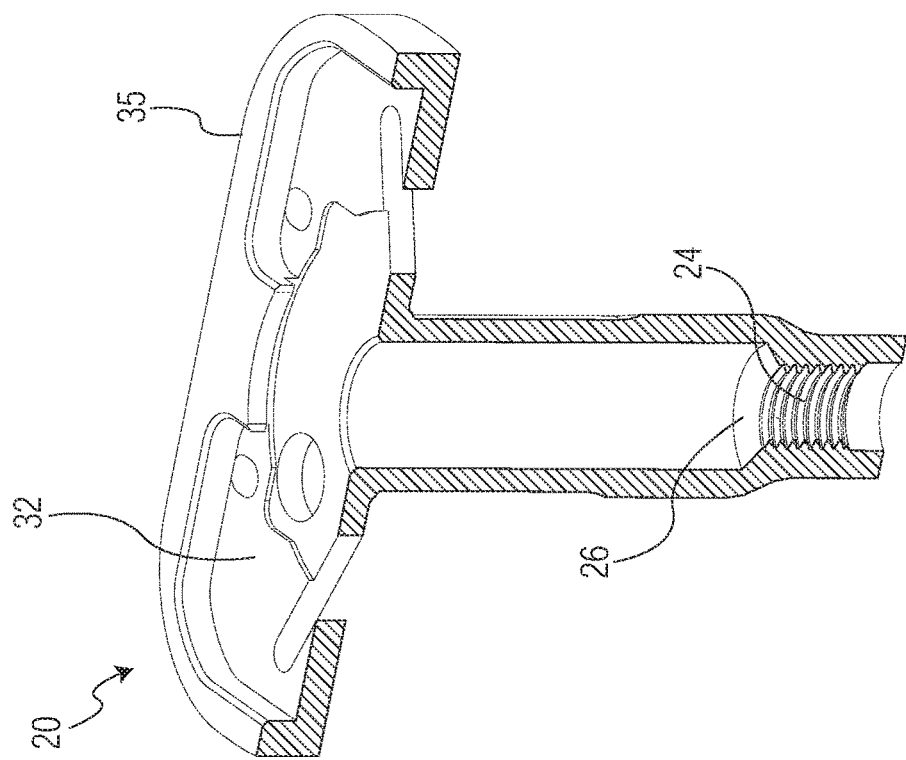
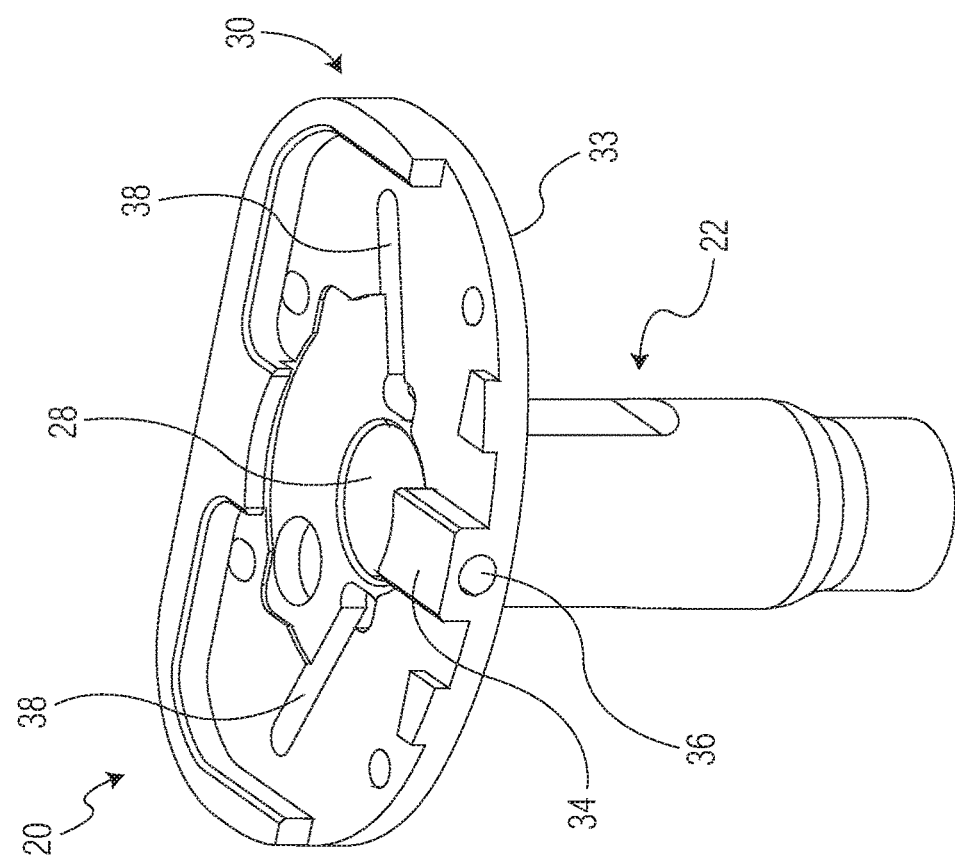
FIG. 2B
FIG. 2A

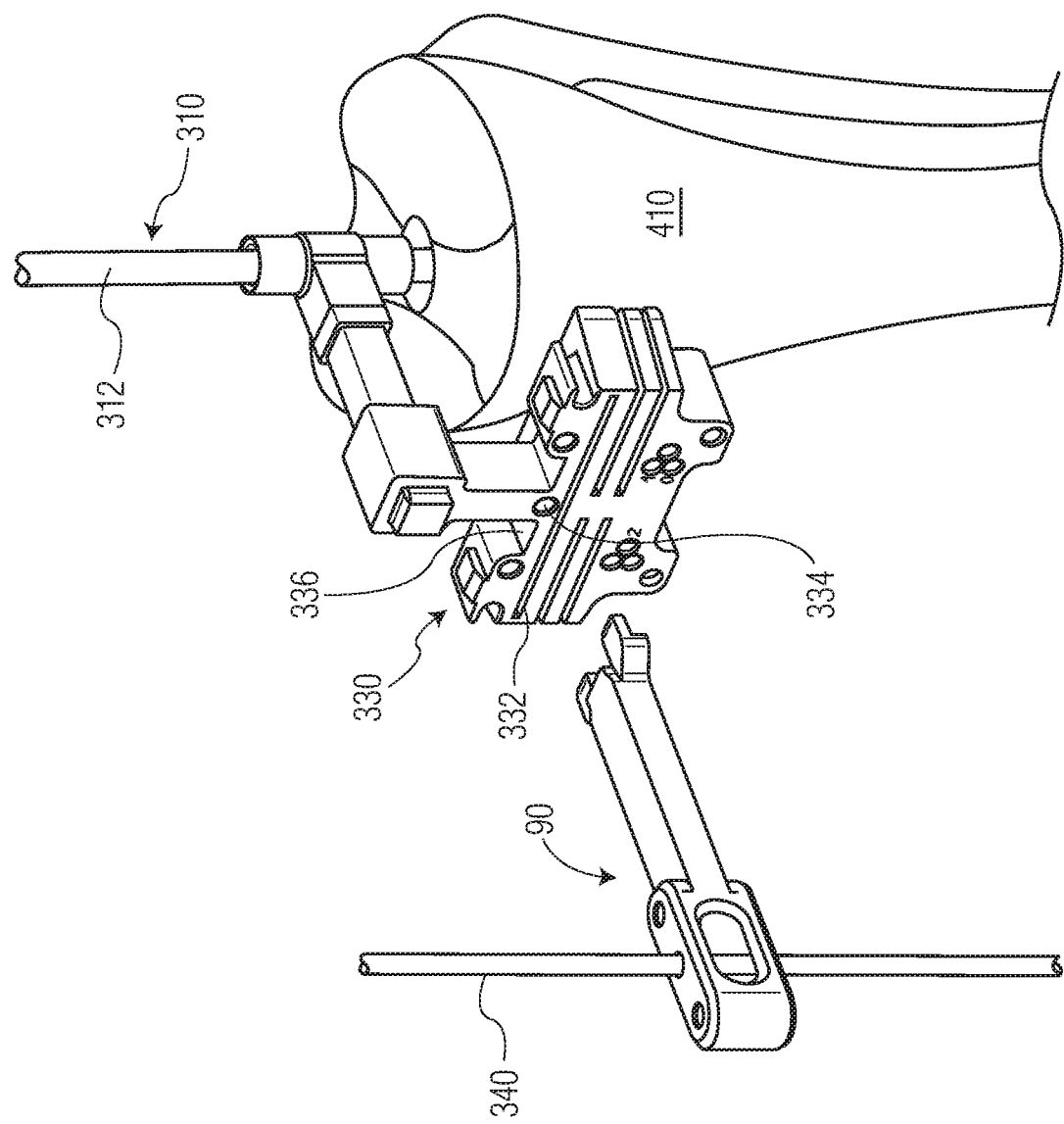

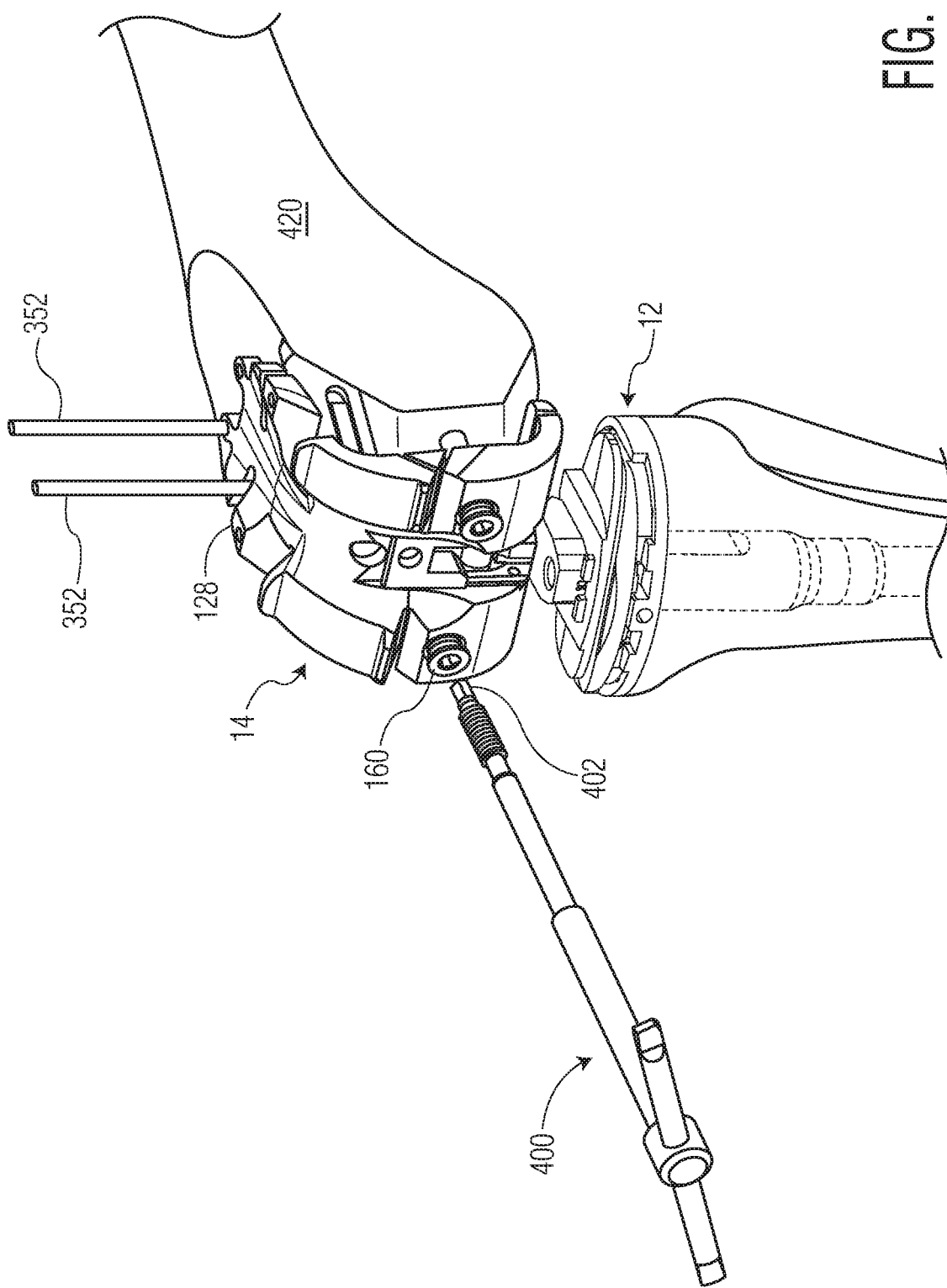

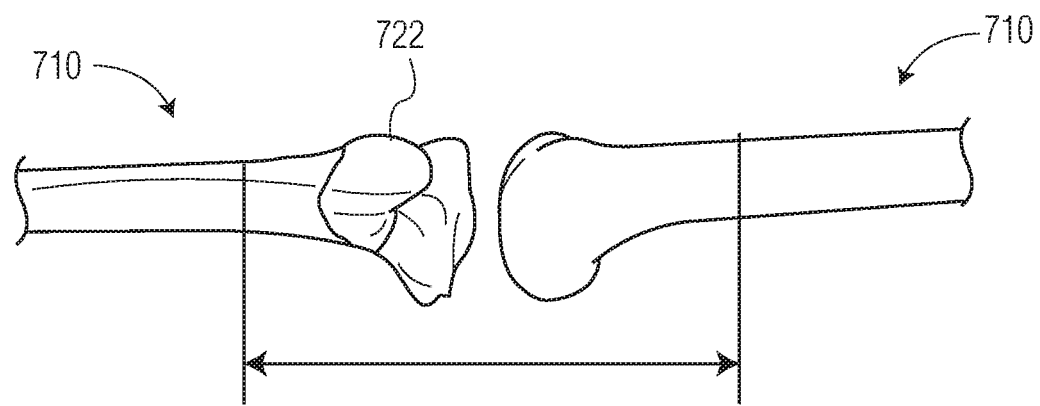
FIG. 17A
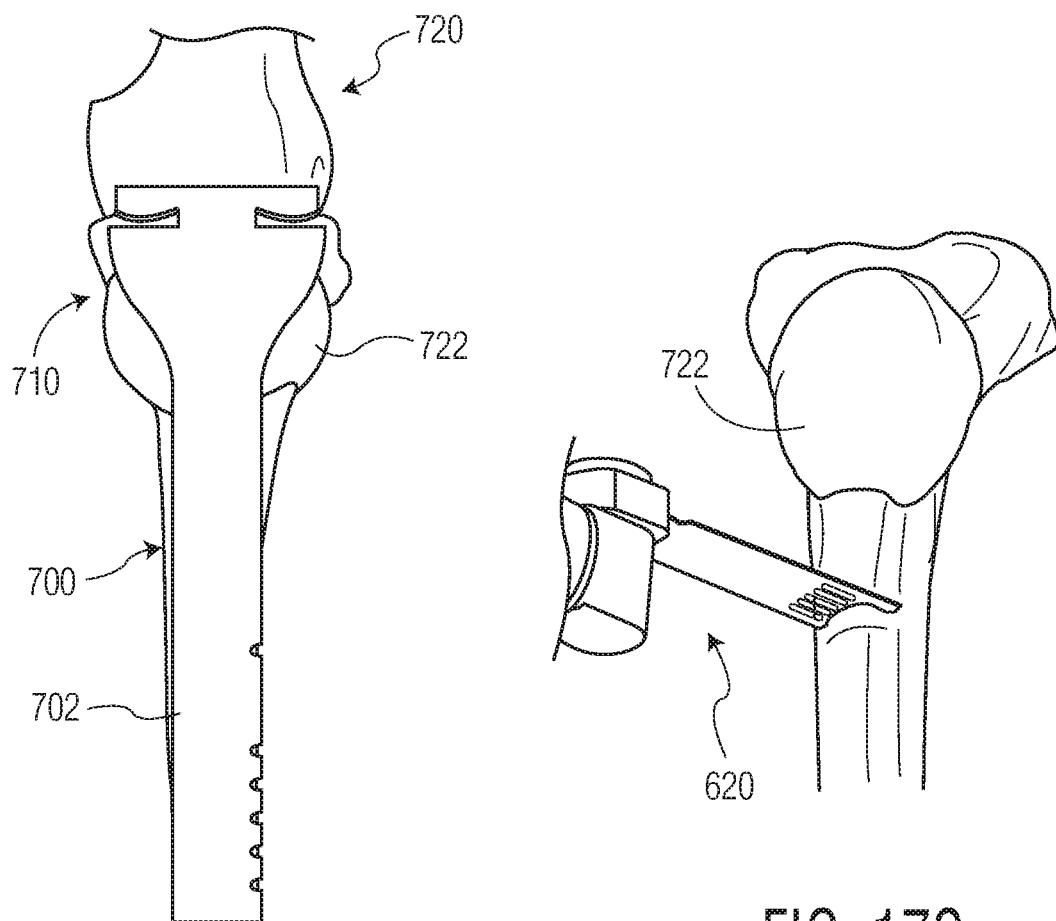
FIG. 17B
FIG. 17C

HINGE KNEE PREPARATION INSTRUMENTATION AND ASSOCIATED METHODS

CROSS-REFERENCE TO RELATED APPLICATION

The present application is a continuation of U.S. application Ser. No. 15/637,619, filed Jun. 29, 2017, which claims the benefit of the filing date of U.S. Provisional Patent Application No. 62/358,222 filed Jul. 5, 2016, the disclosures of which are hereby incorporated herein by reference.

BACKGROUND OF THE INVENTION

Total knee arthroplasty (TKA) or total knee replacement is a common orthopedic procedure in which damaged or diseased articular cartilage and/or bone of the knee is replaced with a prosthesis. In a TKA, a surgeon generally selects one of several different categories of total knee prostheses for implantation depending on the needs of the patient. Prior to implantation of such prosthesis, a surgeon generally resects a portion of the patient's native tibia and femur so as to shape these bones to receive the particular prosthesis selected.

A hinged total knee prosthesis is one category of total knee prostheses. Hinge knee prostheses are typically the most constrained category of total knee prostheses as they most significantly limit the total range of motion of a patient's repaired knee. However, because of such constraint, hinge knee prostheses often provide the most stability and are, therefore, most useful to patients' who have severe joint instability caused by bone loss, ligament deficiencies, and the like. In this regard, hinge knee prostheses are often selected for patients undergoing a revision procedure in which a previously implanted prosthesis is replaced. This can be due to significant bone loss or ligament deficiencies at least partially caused by the previous prosthesis. In addition, hinge knee prostheses are also commonly selected for patients who have bone cancer, such as osteosarcoma, of the tibia and/or femur.

Performing a revision procedure to implant a hinge knee prosthesis can differ quite significantly from that of an oncology procedure to do the same. For example, in a revision procedure, a surgeon removes the previously implanted prosthesis exposing bone that had been shaped in a previous procedure. Although significant deformities can be present, the resected bone and bone deformities often do not extend beyond the metaphysis. So whatever bone stock remains is further shaped and bolstered to receive the hinge knee prosthesis.

In contrast, in an oncology procedure, a patient may have a cancerous tumor in the distal femur or proximal tibia. In order to remove such cancer, a significant portion of the patient's bone is removed along with the cancer. In this regard, resection may be performed along the bone's diaphysis thereby removing the entire proximal tibia or distal femur. In addition, the patient often has a healthy, pristine bone opposite that of the malignant bone. Thus, in order to perform the appropriate replacement, the resected malignant bone must be rebuilt and the pristine bone must be shaped to receive the appropriate components.

Despite the differences between revision and oncology TKA procedures there is some commonality between these procedures in that the tibia and femur are typically resected first, and then a hinge knee trial is assembled onto the resected bone to assess patellofemoral kinematics and joint capsule tightness. If adjustments need to be made, the trial is disassembled and further resections are performed, which may result in an iterative process of assembly, disassembly, and resection that tends to raise the joint line. In addition, the assembly and disassembly of the hinge trial, which often requires an axle to be inserted into a femoral component from a lateral or medial side thereof and through a bearing plate disposed between adjacent condylar portions of the femoral component, can be time consuming which can result in increased risk of infection and overall recovery time.

Numerous instruments, such as trials, cutting guides, and the like, have been made available to help perform hinge knee prosthesis implantation for both revision and oncology procedures. However, such instruments often differ significantly to account for the differences between the procedures. Thus, a manufacturer is often required to offer a large assortment of instrumentation that results in significant manufacturing costs.

In addition, such instruments are provided to an operating theater in sets. Such sets themselves are often comprised of numerous instruments. For example, a currently performed hinge knee procedure may require about 24 instrument cases and 28 instrument trays. These instruments may be stored, cleaned, packaged, and shipped by the manufacturer to the healthcare facility in which the procedure is to take place. In some instances, the instruments may be stored and sterilized at the healthcare facility itself. The demands of manufacturing, storing, maintaining, sterilizing, packaging, shipping and tracking such a diverse, complicated and large quantity of instruments can be expensive, particularly in a world that is increasingly demanding cheaper surgical procedures. For example, a set of instruments for performing a TKA procedure may cost about 40,000 USD to manufacture. These instruments may then be placed into circulation. While in circulation, these instruments must be stored, repaired, sterilized, packaged and shipped numerous times over contributing to the overall costs of the instruments. The more instruments provided in each set, the greater the life-cycle costs become, which may reflect back to the cost of the TKA procedure.

Therefore, further improved instruments and consolidation of instruments for use in hinge knee procedures is desired.

BRIEF SUMMARY OF THE INVENTION

Described herein are devices, systems, and methods for performing TKA. In particular, a hinge knee trial assembly is disclosed which can be utilized in revision procedures and oncology procedures to help prepare bone for a hinge knee prosthesis. One example of such a hinge knee prosthesis is disclosed in U.S. application Ser. No. 14/820,151, the disclosure of which is hereby incorporated herein by reference in its entirety. The hinge knee trial assembly generally includes a tibial trial assembly and femoral trial assembly. The tibial trial assembly includes an intercondylar axle that can be inserted into an intercondylar space of a femoral component of the femoral trial assembly and be easily connected thereto for assessment of joint kinematics. In addition, the distance between the tibial trial assemblies from the femoral trial assembly can be adjusted in measured increments while the axle remains connected to the femoral trial assembly. Furthermore, adjustments of the proximal-distal location of the femoral component of the femoral trial assembly can be adjusted relative to the patient's patella while the hinge knee trial assembly is mounted to the femur and tibia. This allows the joint to be assessed prior to femoral resection so as to help maintain a natural joint line. In addition to the hinge knee trial assembly, other associated instruments and methods of use are also described.

In one aspect of the present disclosure, a hinge knee system includes a tibial assembly and a femoral assembly. The tibial assembly includes a distal end, a proximal end, and an axle component. The distal end is configured to connect to an end of a tibia. The proximal end has a proximally facing bearing surface. The axle component extends from the proximal end and has an axle and axle support. The femoral assembly includes a distal femoral component, the distal femoral component includes first and second condylar portions and an intercondylar portion disposed therebetween. The intercondylar portion has a recess configured to receive the axle and is defined by one or more contoured surfaces that are configured to articulate with the axle when the axle is received within the recess so that the tibial assembly can be rotated relative to the femoral assembly about the axle.

Additionally, the tibial assembly may include a proximal tibial component having a diaphyseal portion. The distal end of the tibial assembly may be at a distal end of the diaphyseal portion and may be configured to connect to a tibia that has been resected along a diaphysis thereof. The tibial assembly may further include a modular tibial insert that defines the proximally facing bearing surface. The proximal tibial component may include a tray portion that receives the tibial insert. Also, the axle component may include a boss slidingly received within an opening extending into the proximal tibial component from a proximal end thereof. The tibial assembly may further include a bearing plate having a distally facing bearing surface. The bearing plate may be engageable to the boss of the axle component at one of a plurality of locations along its length. The distally facing bearing surface may correspond to the proximally facing bearing surface so as to interface therewith when the bearing plate is engaged to the axle component. The boss may include an array of transverse grooves disposed along its length at predetermined intervals, and the bearing plate may include first and second bearing portions that each may each include a flange configured to engage a respective transverse groove of the boss. The axle component may define an opening extending through the boss along its length, and the proximal tibial component and axle component may include internal threads situated along their respective openings so that when the boss is received within the opening of the proximal tibial component, the internal threads of the boss are disposed adjacent the internal threads of the proximal tibial component. The axle may have a longitudinal length that is smaller than a distance between the first and second condylar portions.

Continuing with this aspect, the tibial assembly may include a baseplate component having a tray portion and a boss extending from the tray portion. The distal end of the tibial assembly may include a bone facing surface of the tray portion that is configured to connect to a resected proximal tibia. Also, the tibial assembly may further include a modular tibial insert that defines the proximally facing bearing surface and is received by the tray portion. The axle component may include a boss slidingly received within an opening extending into the baseplate component and along the boss thereof. The tibial assembly may further include a bearing plate having a distally facing bearing surface. The bearing plate may be engageable to the boss of the axle component at one of a plurality of locations along its length. The distally facing bearing surface may correspond to the proximally facing bearing surface so as to interface therewith when the bearing plate is engaged to the axle component. The boss of the axle component may include an array of transverse grooves disposed along its length at predetermined intervals, and the bearing plate may include first and second bearing portions that each include a flange configured to engage a respective transverse groove of the boss. The axle component may define an opening extending through the boss thereof along its length, and the baseplate component and axle component may include internal threads situated along their respective openings so that when the boss is received within the opening of the baseplate component, the internal threads of the boss are disposed adjacent the internal threads of the proximal tibial component.

Furthermore, the femoral assembly may include a shuttle slidingly disposed between the first and second condylar portions and adjacent the recess. The shuttle may have a first position in which the recess is exposed so as to receive the axle and a second position in which the shuttle covers the recess so as to retain the axle within the recess. The shuttle may include flanges extending from opposite sides thereof, and the first and second condylar portions may each define slots that slidingly receive respective flanges of the shuttle. The femoral assembly may include a diaphyseal portion that extends from the distal femoral component and may be configured to connect to a femur that has been resected along a diaphysis thereof. The distal femoral component may include a plurality of resection slots extending through the first and second condylar portions for resecting a distal femur. The distal femoral component may include a bone interface surface configured to interface with previously resected surfaces of a distal femur. The femoral assembly may further include a stem adapter and the intercondylar portion may include an adaptor connection member. The stem adaptor may have a stem connection portion that may have a threaded opening for threaded connection to an intramedullary stem and a post that may extend from the stem connection portion. The adaptor connection member may include a post opening configured to receive the post. The stem adaptor may also include a locking pawl rotatably connected to the stem adaptor, and the adaptor connection member may include a latch opening disposed adjacent to the post opening so that when the post is disposed in the post opening the locking pawl engages the latch opening. The post may define a first longitudinal axis and the stem connection member may define a second longitudinal axis. The first and second axes may intersect at an oblique angle. The femoral assembly may further include first and second screws. The first condylar portion may define a threaded opening extending therethrough for threadedly engaging the first screw, and the second condylar portion may define a threaded opening extending therethrough for threadedly engaging the second screw.

In another aspect of the present disclosure, a method of preparing a knee joint to receive a hinge knee prosthesis includes mounting a tibial trial assembly to a tibia and a femoral trial assembly to a femur; connecting an axle of tibial trial assembly to the femoral trial assembly by inserting the axle into a recess disposed between a first and second condylar portions of the femoral trial assembly; assessing patellofemoral and tibiofemoral kinematics by rotating the knee joint about the axle through flexion and extension; and resecting the distal femur through resection slots extending through the first and second condylar portions of the femoral trial assembly.

Additionally, the method may include removing a previously implanted knee prosthesis from the femur and tibia. The mounting step may include engaging surfaces of the distal femur resected in a previous surgical procedure with an interior surface of a femoral component of the femoral trial assembly. The method may also include further resecting a proximal end of the tibia, reaming an intramedullary canal of the tibia, and reaming an intramedullary canal of the femur. Resecting the tibia and reaming the tibia and femur may be performed before the mounting step, and resecting the distal femur may be performed after the mounting step. The connecting step may include sliding a shuttle of the femoral trial assembly over the axle and recess so as to retain the axle within the recess. Also, the method may include adjusting a proximal-distal position of the femoral trial assembly relative the femur and a patella by rotating a screw extending through one of the first and second condylar portions and in contact with the femur.

Continuing with this aspect, the method may include moving an axle component that comprises the axle relative to a baseplate component of the tibial trial assembly while the axle is connected to the femoral trial assembly so as to adjust the distance between the baseplate component and femoral trial assembly. The moving step may include sliding a boss of the axle component through an opening in the baseplate component. Also, the moving step may include moving the axle component from a first set position to a second set position. The moving step may include disengaging a first groove disposed along the length of the boss with a bearing plate, and engaging a second groove offset from the first groove with the bearing plate. The first groove may be associated with the first set position, and the second groove may be associated with the second set position. The bearing plate may have a distally facing bearing surface that interfaces with a proximally facing bearing surface of the tibial trial assembly when the axle component is in both the first and second set positions.

In a further aspect of the present disclosure, a method of preparing a knee joint to receive a hinge knee prosthesis includes resecting a femur and tibia; mounting a tibial trial assembly to the tibia and a femoral trial assembly to the femur; connecting an axle of an axle component of the tibial trial assembly to the femoral trial assembly; assessing patellofemoral and tibiofemoral kinematics by rotating the knee joint about the axle through flexion and extension; and moving the tibial trial assembly relative to the femoral trial assembly from a first predetermined distance to a second predetermined distance while the axle remains connected to the femoral trial assembly.

Additionally, resecting the femur may be performed after the mounting step. However, resecting the femur may be performed before the mounting step. In addition, resecting the femur may include resecting a cancerous portion of the femur. Also, resecting the tibia may include resecting a cancerous portion of the tibia. The connecting step may include inserting the axle into a recess disposed between first and second condylar portions of the femoral trial assembly. The moving step may include inserting a threaded tool into an opening within a boss of the axle component, engaging internal threads defined the boss and defined by a tibial component within which the boss is received, and rotating the threaded tool to distract the axle component relative to tibial component. The moving step may be performed with the tibia and femur being in about 90 degrees of flexion. Also, the moving step may include disengaging a first groove disposed along the length of the boss with a bearing plate, and engaging a second groove offset from the first groove with the bearing plate. The first groove may be associated with the first predetermined distance, and the second groove may be associated with the second predetermined distances. Also, the axle may be rigidly fixed and immovable relative to the shaft portion of the axle component, and the bearing surface may be disposed entirely between the condylar portions.

BRIEF DESCRIPTION OF THE DRAWINGS

The features, aspects, and advantages of the present invention will become better understood with regard to the following description, appended claims, and accompanying drawings in which:

FIG. 2A is a perspective view of a baseplate trial of the tibial trial assembly of FIG. 1.

FIG. 2B is a cross-sectional view of the baseplate trail of FIG. 2A taken along a midline thereof.

FIGS. 17A-17J depict a method of preparing a femur and tibia for a hinge knee prosthesis in an oncology procedure involving a cancerous tibia.

DETAILED DESCRIPTION

When referring to specific directions in the following discussion of certain devices, it should be understood that such directions are described with regard to the device's orientation and position during exemplary application to the human body. Thus, as used herein, the term "proximal" means closer to the heart, and the term "distal" means further from the heart. The term "anterior" means toward the front part of the body or the face, the term "posterior" means toward the back of the body. The term "medial" means closer to or toward the midline of the body, and the term "lateral" means further from or away from the midline of the body. The term "inferior" means closer to or toward the feet, and the term "superior" means closer to or toward the crown of the head. As used herein, the terms "about," "generally," and "substantially" are intended to mean that slight deviations from absolute are included within the scope of the term so modified.

Figure 1:
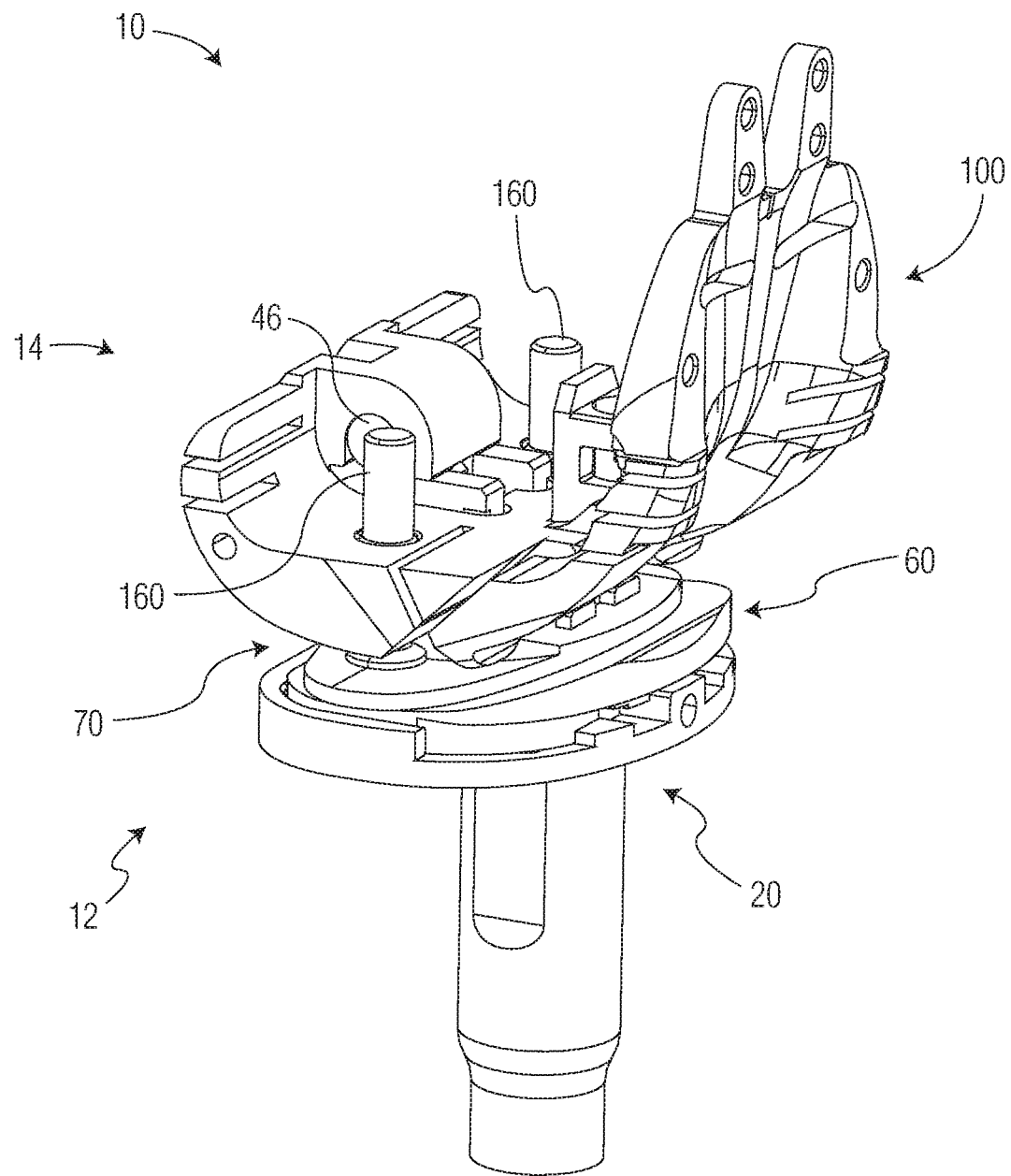
FIG. 1 is a perspective view of a hinge knee trial assembly that includes a tibial trial assembly and femoral trial assembly according to an embodiment of the present disclosure.

FIG. 1 depicts a hinge knee trial assembly 10 according to an embodiment of the present disclosure. Hinge knee trial assembly 10 includes a femoral trial assembly 14 and a tibial trial assembly 12. Tibial trial assembly 12 generally includes a baseplate component 20, axle component 40, tibial insert 60, bearing plate 70, and keel trial 80 (see FIG. 7B).

FIGS. 2A and 2B depict baseplate component 20. Baseplate component 20 includes a tray portion 30 and a boss 22. Boss 22 extends from a distal side of tray portion 30 and defines a boss opening 28 that extends entirely through boss 22 and through tray portion 30. Boss opening 28 is sized to slidingly receive a boss 50 of axle component 40, as described further below. Boss 22 includes internal threads 24 at a distal end thereof while the remainder of boss 22 defines a smooth bore. The interface of the smooth bore and threads 24 forms a shelf 26, as shown in FIG. 2B. Internal threads 24 are configured to threadedly engage external threads of a stem trial 21 (see FIG. 15H).

Tray portion 30 includes a proximal plate surface 32 that has a rim 35 extending partially about its perimeter which forms a dish that is configured to receive tibial insert 60. Keel slots 38 extend through tray portion 30 adjacent boss 22. An anterior protrusion 34 extends from plate surface 32 and defines an anterior opening 36 that is configured to receive a cylindrical projection 98 of an alignment handle 90, as is described below. A distal surface 33 of tray portion 30 is configured to be mounted onto a resected proximal tibia. Tibial augments (not shown) can be coupled to distal surface 33 as necessary to accommodate bone deficiencies that may be realized during a revision procedure, for example.

Figure 3B:
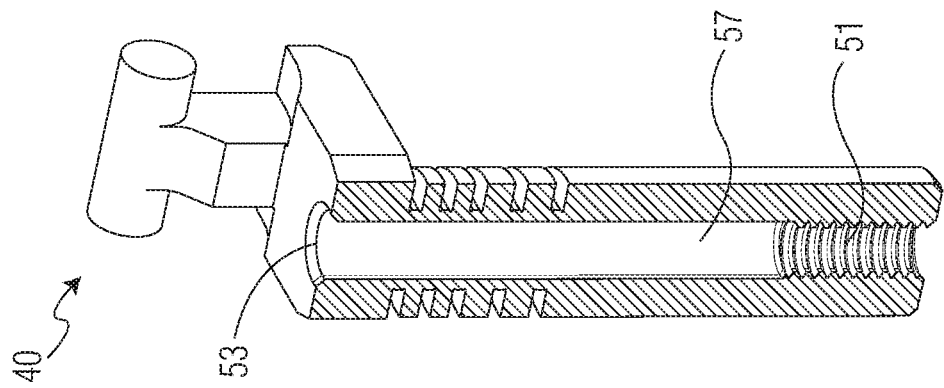
FIG. 3B is a partial cutaway view of the intercondylar axle component of FIG. 3A.
Figure 3A:
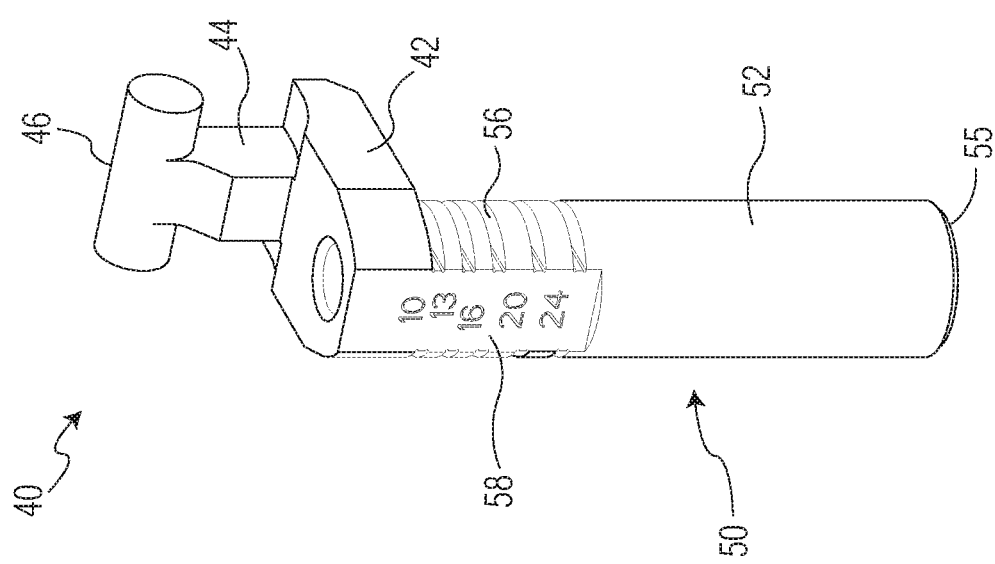
FIG. 3A is a perspective view of an intercondylar axle component of the tibial trial assembly of FIG. 1.

FIGS. 3A and 3B depict axle component 40. Axle component 40 includes an axle 46, axle support 44, base 42 and boss 50. Boss 50 projects from base 42 in a distal direction. Boss 50 includes a shaft portion 52. A distal end of the cylindrical shaft portion 52 is beveled to form a shoulder 55. In some embodiments, a second cylindrical shaft portion (not shown) may extend coaxially from shaft portion 52 and may have a smaller diameter than shaft portion 52 to form the shoulder 55.

An array of engagement grooves 56 is disposed along the length of shaft portion 52 so that individual grooves 56 of the array are spaced at predetermined intervals. These grooves 56 extend into an outer surface of shaft portion 52 and in an anterior-posterior direction. Each groove 56 on one side of shaft portion 52 is paired with a corresponding groove 56 at the opposite side of shaft portion 52. Each of these pairs of grooves 56 are associated with indicia 58 that indicate a tibial insert thickness to be used for the final hinge prosthesis. Thus, the distance between each groove 56 in a proximal-distal direction corresponds to a difference in thickness between different sized tibial inserts. A tool opening 53 extends through shaft portion 52 and along the length thereof. Internal threads 51 are disposed at a distal end of shaft portion 52. The remainder of shaft portion 52 proximal to internal threads 51 defines a smooth bore 57.

Axle support 44 extends proximally from base 42 and is offset posteriorly from boss 50. Such offset helps provide clearance so that tool opening 53 can be easily accessed by a tool. Axle support 44, as shown, has a substantially rectangular cross-sectional geometry. Axle 46 is attached at a proximal end of axle support 44. Axle 46 is substantially cylindrical and defines a longitudinal axis that extends in a lateral-medial direction transverse to a longitudinal axis defined by boss 50. Axle 46 has a length that is less than a distance between condylar portions 122 of a femoral component 100 of femoral trial assembly 14 which allows axle 46 to be passed therebetween into an intercondylar space, as is described in more detail below. Moreover, axle 46, as depicted, is rigidly fixed and immovable relative to shaft portion 52. In this regard, axle does not have moving parts which are susceptible to failure under normal operating conditions. However, it should be understood that axle could be modularly connectable to shaft portion 52.

Figure 4A:
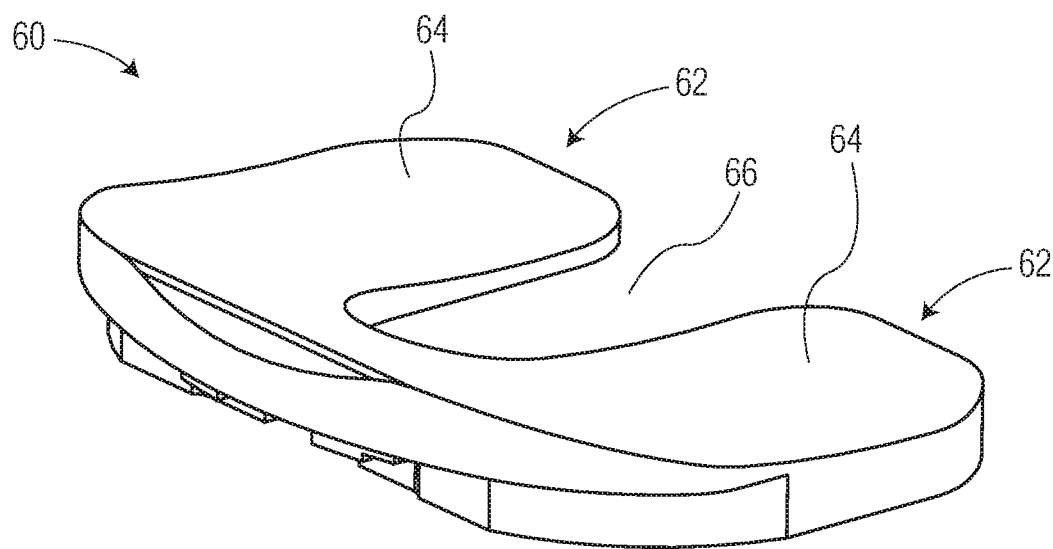
FIG. 4A is a top perspective view of a tibial insert of the tibial trial assembly of FIG. 1.
Figure 4B:
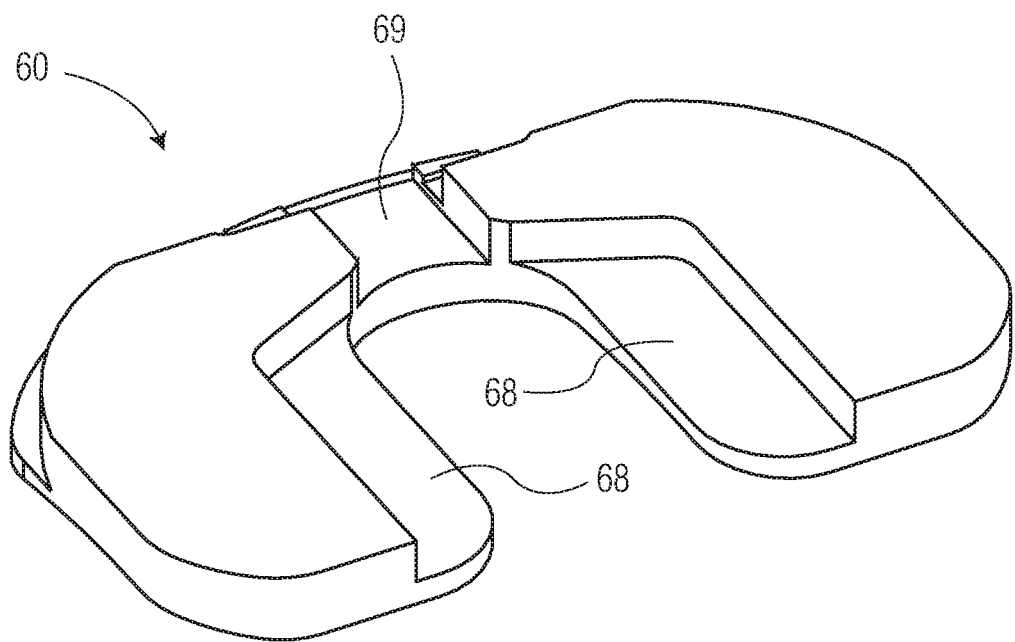
FIG. 4B is a bottom perspective view of the tibial insert of FIG. 4A.

FIGS. 4A and 4B depict tibial insert 60. Tibial insert 60 includes bearing portions 62 that define proximally facing bearing surfaces 64 that are preferably concavely curved in a sagittal plane. An intrabearing recess 66 partially separates bearing portions 62. At distal side of insert 60 opposite that of bearing surfaces 64, insert 60 includes indented surfaces 68 that flank recess 66 from two sides, as best shown in FIG. 4B. Such indented surfaces 68 provide clearance for a bridge 84 of keel trial 80. An anterior notch 69 is also located on the same side of insert 60 as indented surfaces 68. Such notch 69 provides clearance for anterior protrusion 34 of baseplate 20.

Figure 5A:
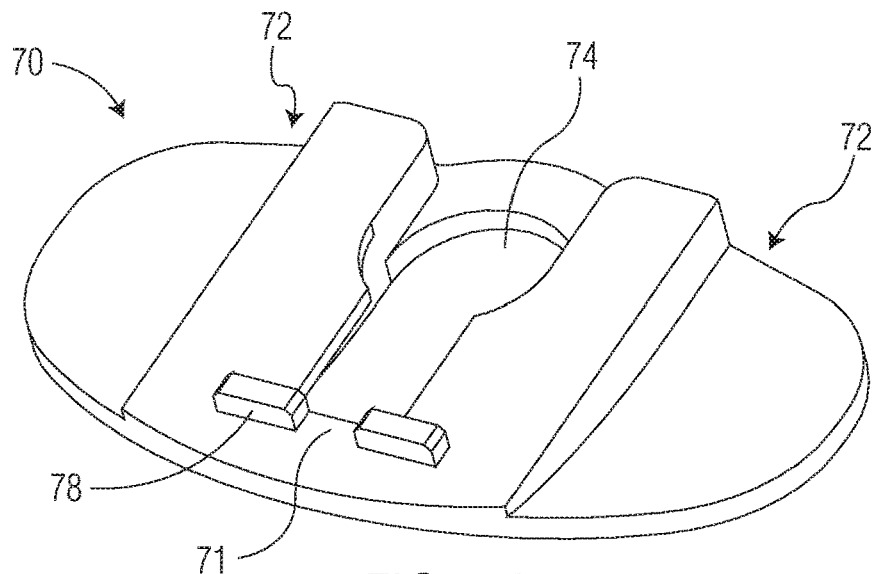
FIG. 5A is a top perspective view of a bearing plate of the tibial trial assembly of FIG. 1.
Figure 5B:
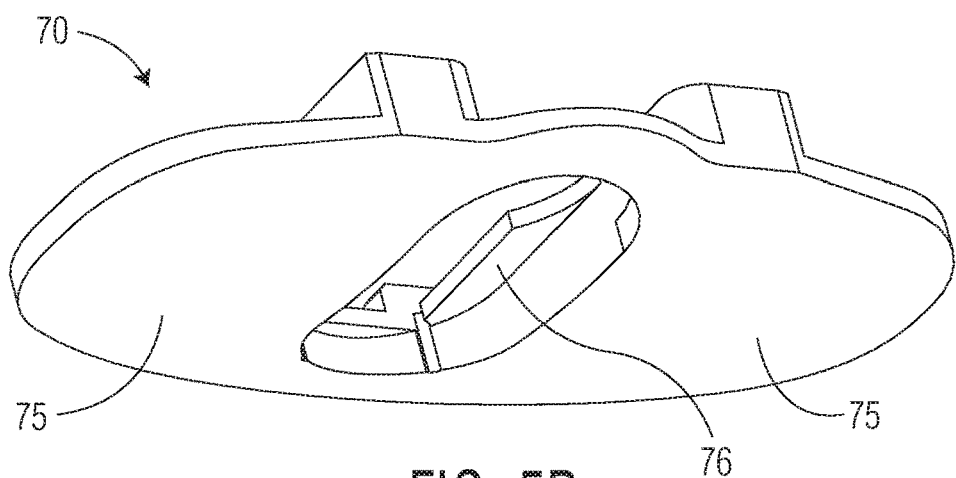
FIG. 5B is a bottom perspective view of the bearing plate of FIG. 4B.

FIGS. 5A and 5B depict bearing plate 70. Bearing plate 70 includes bearing portions 72 that define distally facing bearing surfaces 75 that are preferably convexly curved in a sagittal plane so as to correspond with proximally facing bearing surfaces 64 of tibial insert 60. An intrabearing elongate opening 74 partially separates bearing portions 72. In addition, anterior flanges 78 extend proximally from bearing plate 70 adjacent opening 74. A viewing notch 71 extends between anterior flanges 78 in an anterior-posterior direction which allows indicia 58 of axle component 40 to be viewed therethrough when axle boss 50 is disposed within opening 74. Each bearing portion 72 includes an elongate flange 76 that extends into opening 74. Such flanges 76 are configured to slidingly engage corresponding pairs of grooves 56 of axle component 40. However, flanges 76 do not extend along the entire length of opening 74 so that flanges 76 can disengage one pair of grooves 56 and then engage another pair of grooves 56 without having to remove boss 50 from opening 74.

Figure 6:
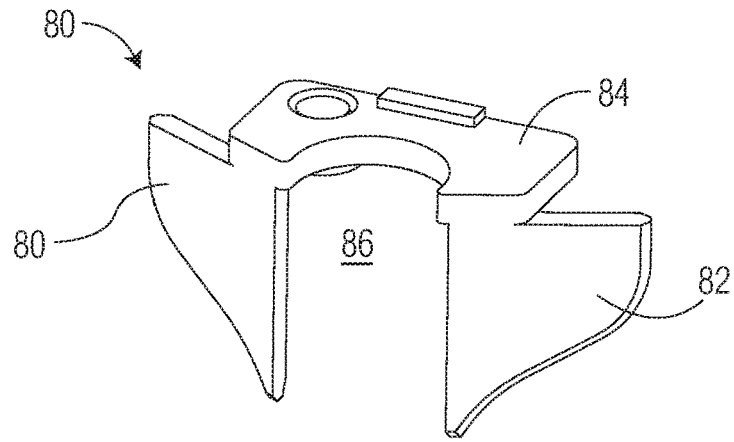
FIG. 6 is a top perspective view of a keel trial of the tibial trial assembly of FIG. 1.

FIG. 6 depicts keel trial 80. Keel trial 80 includes keel portions 82 that are connected by a bridge 84. Such bridge 84 defines a semicircular recess 86 that is configured to extend about a portion of axle boss 50 when keel trial 80 is connected to baseplate component 20.

Figure 7B:
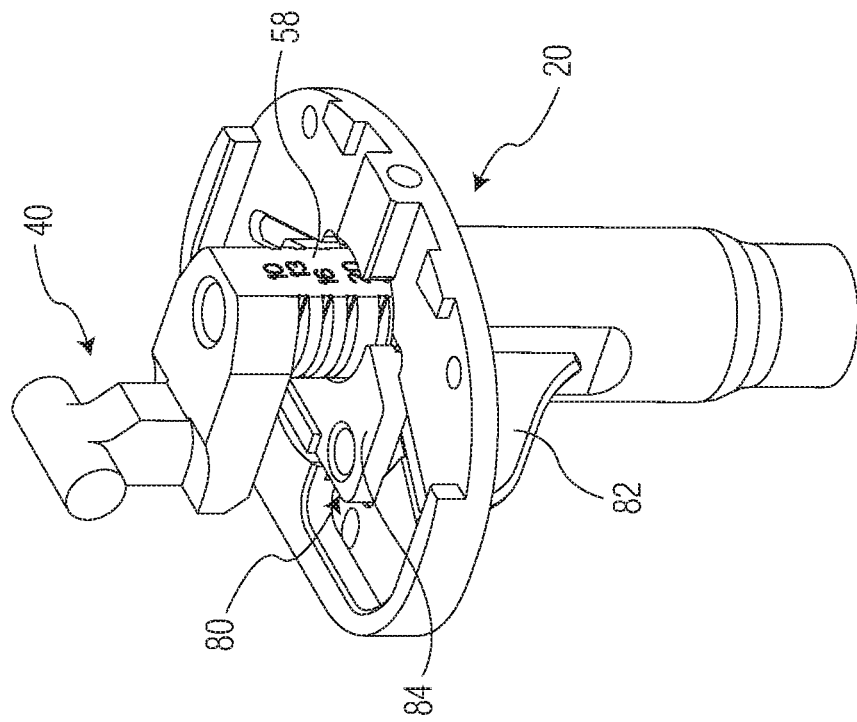
FIG. 7B is a side perspective view of the baseplate trial, keel trial, and intercondylar axle component of the tibial trial assembly of FIG. 1, as assembled.
Figure 7A:
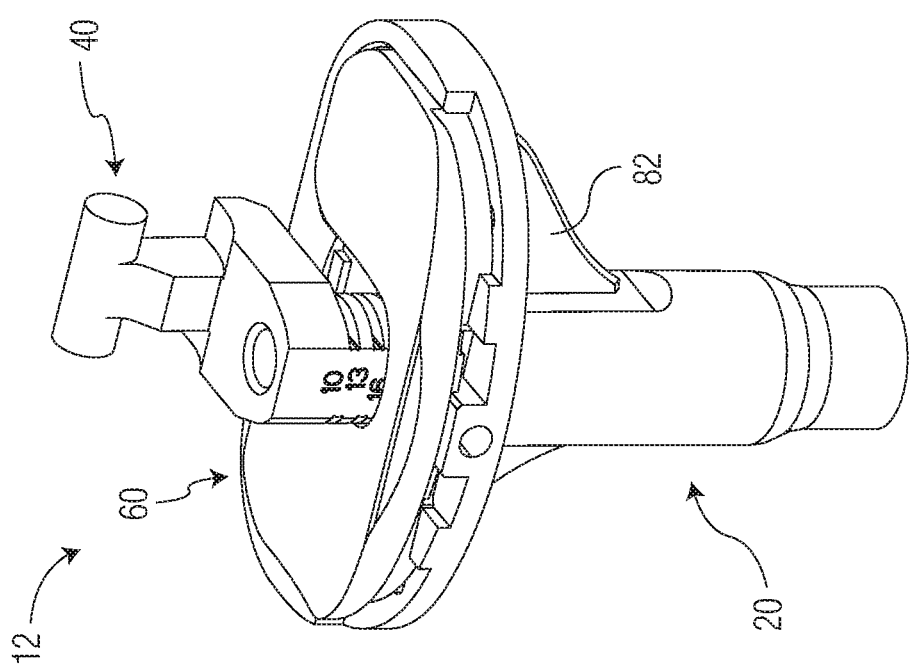
FIG. 7A is front perspective view of the baseplate trial, tibial insert, keel trial, and intercondylar axle component of the tibial trial assembly of FIG. 1, as assembled.
Figure 7D:
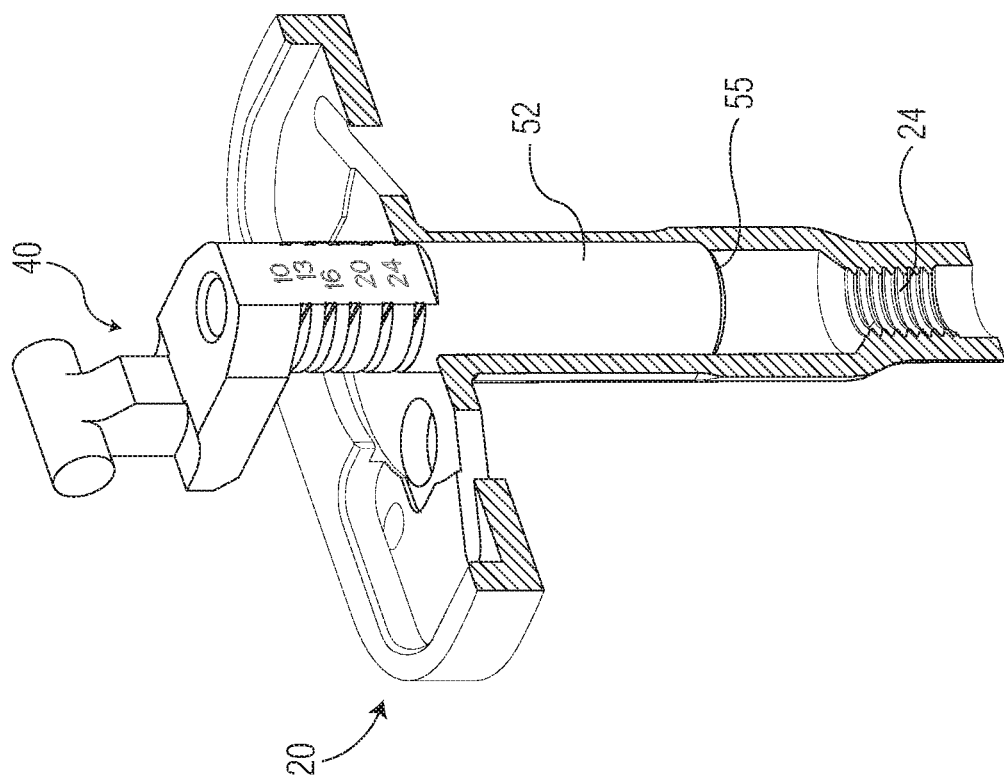
FIG. 7D is a cutaway view of the baseplate trial and intercondylar axle component of the tibial trial assembly of FIG. 1, as assembled.
Figure 7C:
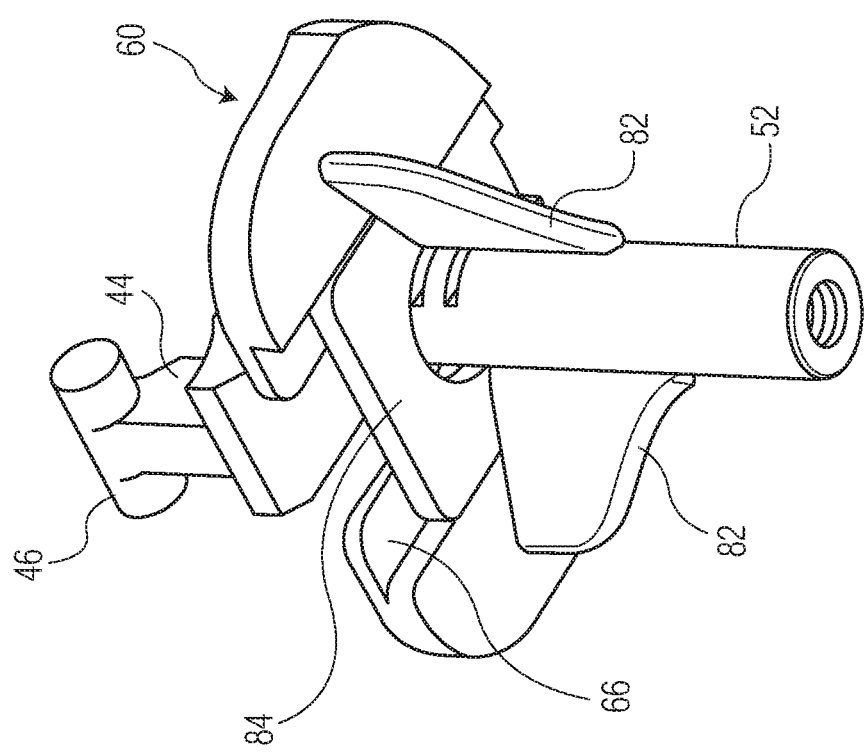
FIG. 7C is a bottom perspective view of the tibial insert, keel trial, and intercondylar axle component of the tibial trial assembly of FIG. 1, as assembled.

FIGS. 7A-7F illustrate the interconnection of components of tibial trial assembly 12. In this regard, as assembled, keel portions 82 of keel trial 80 extend distally through corresponding keel slots 38 in baseplate component 20. Bridge 84 of keel trial 80 is positioned posterior to boss opening 28 and spans between keel slots 38, as best shown in FIG. 7B. Tibial insert 60 rests on proximal plate surface 32 and is received by the dish defined by tray portion 30. In addition, indented surfaces 68 rest on bridge 84 of keel trial 80, as best shown in FIG. 7C.

Axle boss 50 is slidingly disposed within boss opening 28 of baseplate component 20 so that indicia 58 face anteriorly. In this regard, axle boss 50 can slide in a proximal-distal direction as well as rotate about a longitudinal axis thereof. When boss 50 is fully inserted into boss opening 28, shoulder 55 of boss 50 rests against shelf 26 of boss 22, and internal threads 51 of boss 50 are positioned adjacent internal threads 24 of boss 22. This allows a threaded tool to engage internal threads 51 and abut a stem trial engaged to internal threads 24 to help distract axle component 50 and baseplate component 20, as is described below.

Figure 7F:
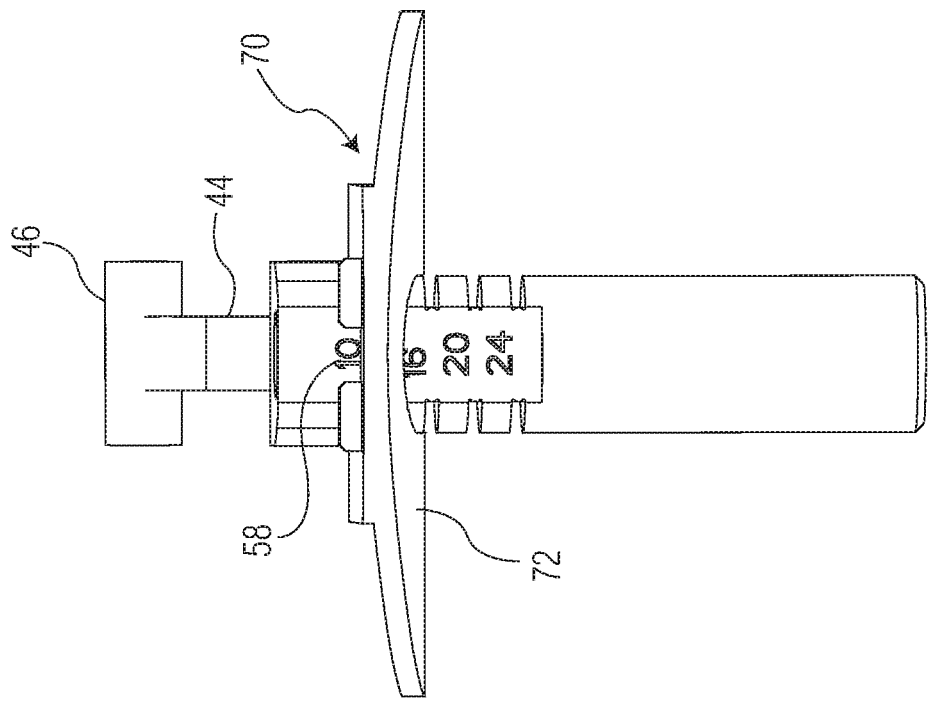
FIG. 7F is a front perspective view of FIG. 7E.
Figure 7E:
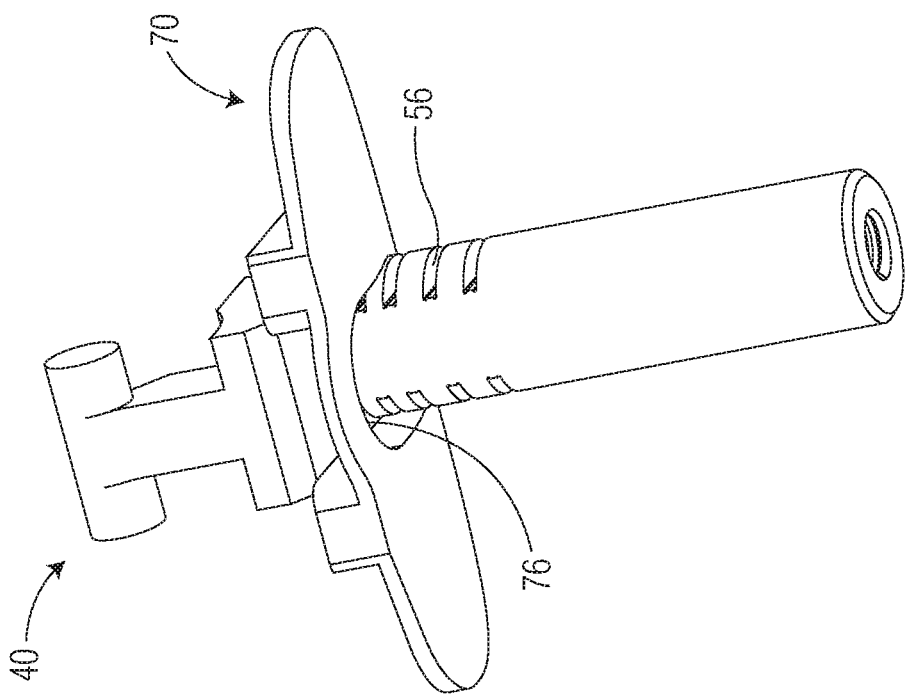
FIG. 7E is a rear perspective view of the bearing plate and intercondylar axle component the tibial trial assembly of FIG. 1, as assembled.

Bearing plate 70 is attached to boss 50 of axle component 40, as shown in FIGS. 7E and 7F. In this regard, flanges 76 slidingly engage a corresponding pair of grooves 56 which constrains bearing plate 70 in a proximal-distal direction relative to axle component 40. However, bearing plate 70 can slide anteriorly to disengage the grooves 56. This allows bearing plate 70 to engage any pair of corresponding grooves 56. When flanges 76 of bearing plate engage such grooves 56, viewing notch 71 aligns with corresponding indicia 58 indicating a tibial insert size (best shown in FIG. 7F). With bearing plate 70 engaged to boss 50, bearing plate 70 rests on tibial insert 60 so that distally facing bearing surfaces 75 interface with proximally facing bearing surfaces 64 (best shown in FIG. 1).

Tibial trial assembly 12, as previously described, allows axle 46 to be moved from one set position to another set position in a proximal-distal direction relative to baseplate component 20. In this regard, when bearing plate 70 is engaged to a first pair of grooves 56 and bearing plate 70 rests on tibial insert 60, axle 46 is located a first predetermined distance from baseplate 20. However, when bearing plate 70 engages a second pair of grooves 56 and bearing plate 70 rests on tibial insert 60, axle 46 is located a second predetermined distance from baseplate component 20 that is different from the first predetermined distance.

Figure 8A:
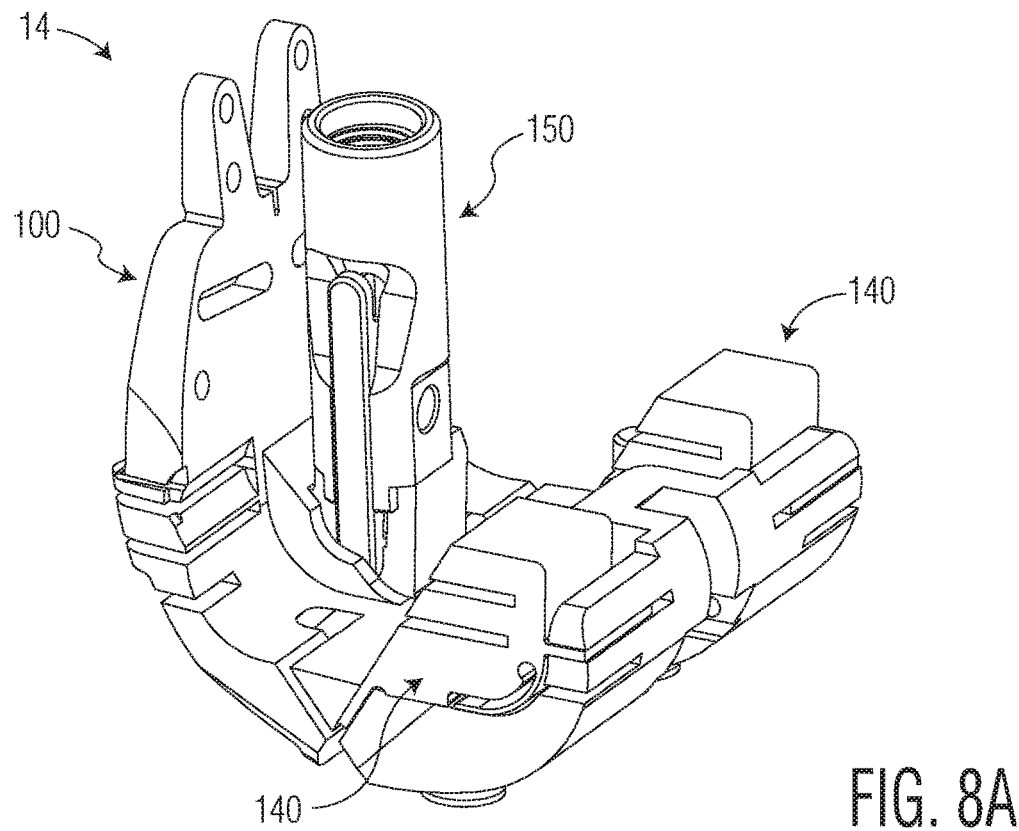
FIG. 8A is a side perspective view of the femoral trial assembly of FIG. 1 including augment trials and a valgus adaptor.
Figure 8B:
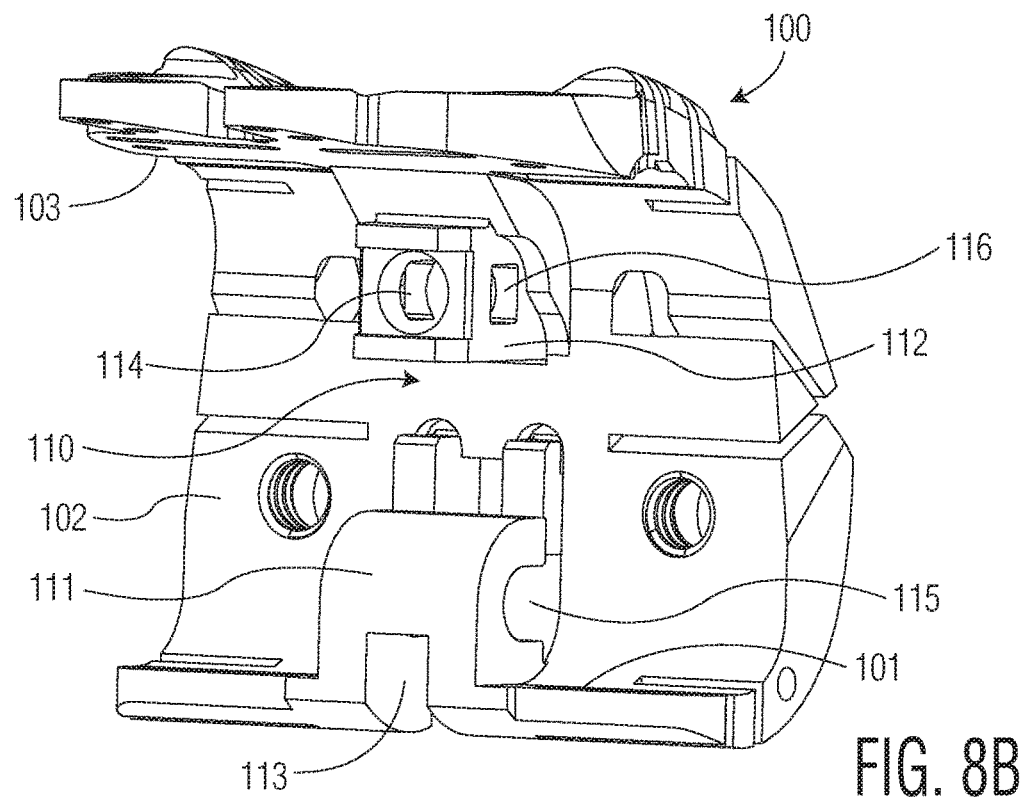
FIG. 8B is a top perspective view of a femoral component trial/guide of the femoral trial assembly of FIG. 8A.

Referring back to FIG. 1 and also to FIG. 8A, femoral trial assembly 14 generally includes a femoral component 100, distalizing screws 160, valgus adaptor 150, and augment trial 140.

Figure 8C:
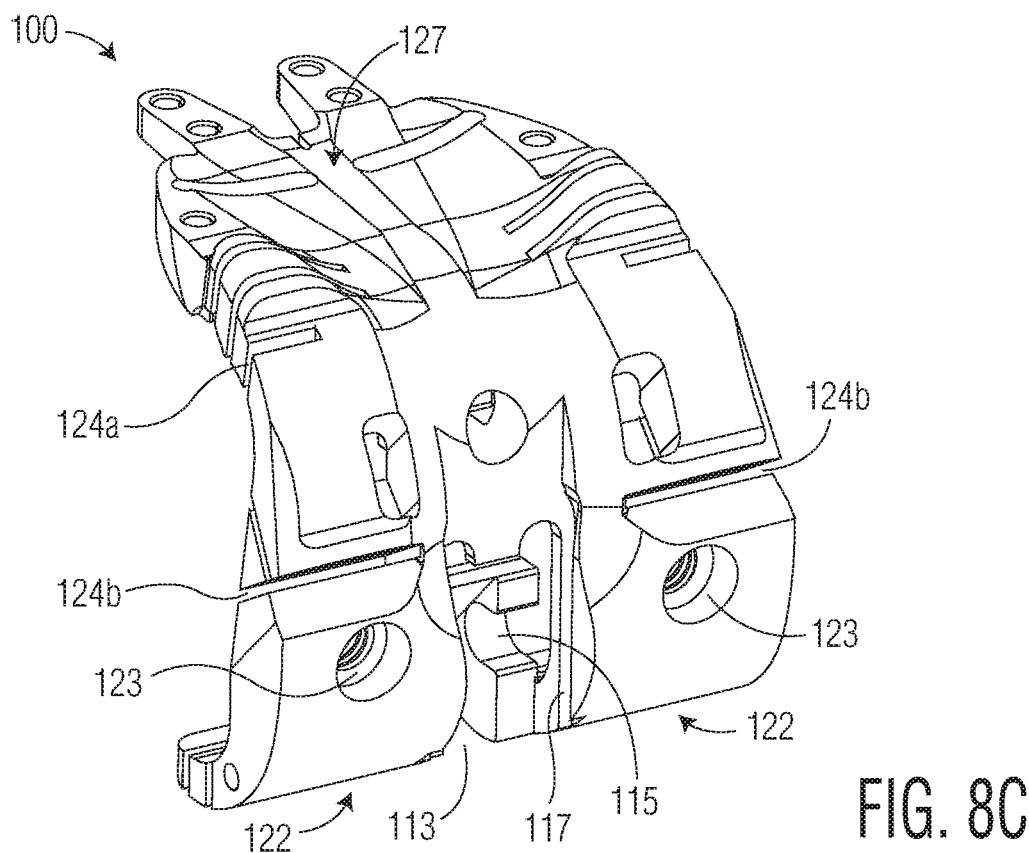
FIG. 8C is a bottom perspective view of the femoral component trial/guide of FIG. 8B.

As depicted in FIGS. 8A-8E, femoral component 100 includes an anterior flange portion 127, condylar portions 122 and an intercondylar portion 110 disposed between condylar portions 122. Threaded openings 123 extend through condylar portions 122 in a proximal-distal direction. In addition, first, second, and third resection slots 124a-c extend through condylar portions 122. In this regard, femoral component 100 acts as both a trial and a cutting guide. Such slots 124a-c are configured to guide a bone saw to perform two to three cuts of the femur, such as an anterior chamfer cut, a posterior chamfer cut and a distal augment cut (optional). Resection slots 124a-c define resection planes 125a-c along which these cuts are performed, as best shown in FIG. 8F. For example a first cutting plane 125a is defined by first and third resection slots 124a, 124c, a second cutting plane 125b is defined by second resection slots 124b, and a third cutting plane 125c is defined by first and second resection slots 124a-b. Femoral component 100 includes guide flanges 126 extending from an exterior surface thereof that are aligned with first and second resection planes 125a-b adjacent first and second cutting slots 124a-b, respectively, as these slots are each utilized for two of the three possible cuts that are performed utilizing femoral component. These flanges 126 do not interfere with articulation of femoral trial assembly 14 with tibial trial assembly 12 as condylar portions 122 do not articulate with tibial trial assembly 12.

Anterior flange 127 is configured to articulate with a patella. Pin holes 129 extend through anterior flange and are configured to receive bone pins. In addition, a pair of pin slots 128 extends through anterior flange 127. These slots 128 are oriented so that a pin can be inserted through such slots 128 to prohibit proximal-distal movement of femoral component 100 relative to a femur, while allowing femoral component 100 to be rotated internally or externally relative to the femur.

Intercondylar portion 110 is configured to connect femoral component 100 to axle component 40 and valgus adaptor 150. In this regard, intercondylar portion 110 is substantially located in a space between condylar portions 122 and includes an axle bearing member 111 and an adaptor connection member 112. Adaptor connection member 112 is disposed at an anterior side of femoral component 100 and defines a post opening 114 and a latch opening 116. Post opening 114 extends in a proximal-distal direction into connection member 112 while latch opening 116 extends into connection member 112 in a direction transverse to post opening 114. A pair of sidewalls 118 (see FIG. 8F) extends proximally from connection member 112 and is disposed adjacent post opening 114. Such sidewalls 118 interface with flat surfaces 159 of valgus adaptor 150 to prevent it from rotating relative to femoral component 100 when connected thereto.

Axle bearing member 111 includes contoured bearing surfaces 119, which as shown in FIG. 8F, define a partially cylindrical recess 115. Such recess 115 extends in a lateral-medial direction between condylar portions 122 and is sized to receive axle 46. A posterior notch 113 intersects the recess. Such notch 113 has a generally rectangular geometry and is sized to receive axle support 44. A pair of guide grooves 117 extends into the condylar portions 122 adjacent the intercondylar space and extends in an anterior-posterior direction, as best shown in FIG. 8C. A locking shuttle 130 is slidingly connected to such guide grooves 117.

Figure 8D:
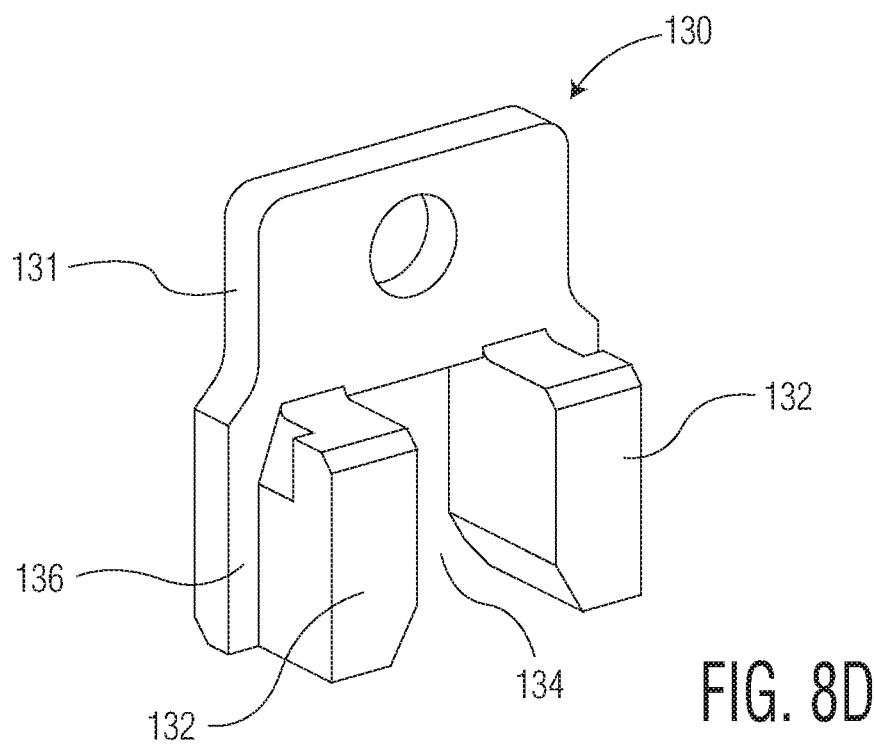
FIG. 8D is a top perspective view of a locking shuttle of the femoral trial assembly of FIG. 8A.
Figure 8E:
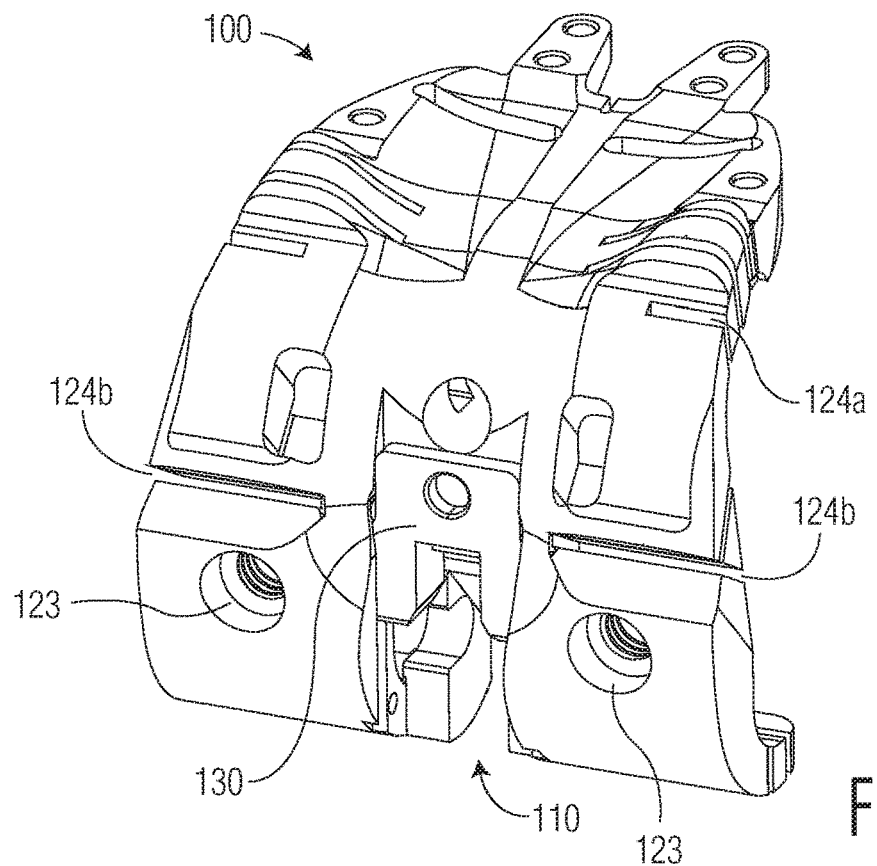
FIG. 8E is a bottom perspective view of the femoral component trial/guide and locking shuttle of the femoral trial assembly of FIG. 8A, as assembled.
Figure 8F:
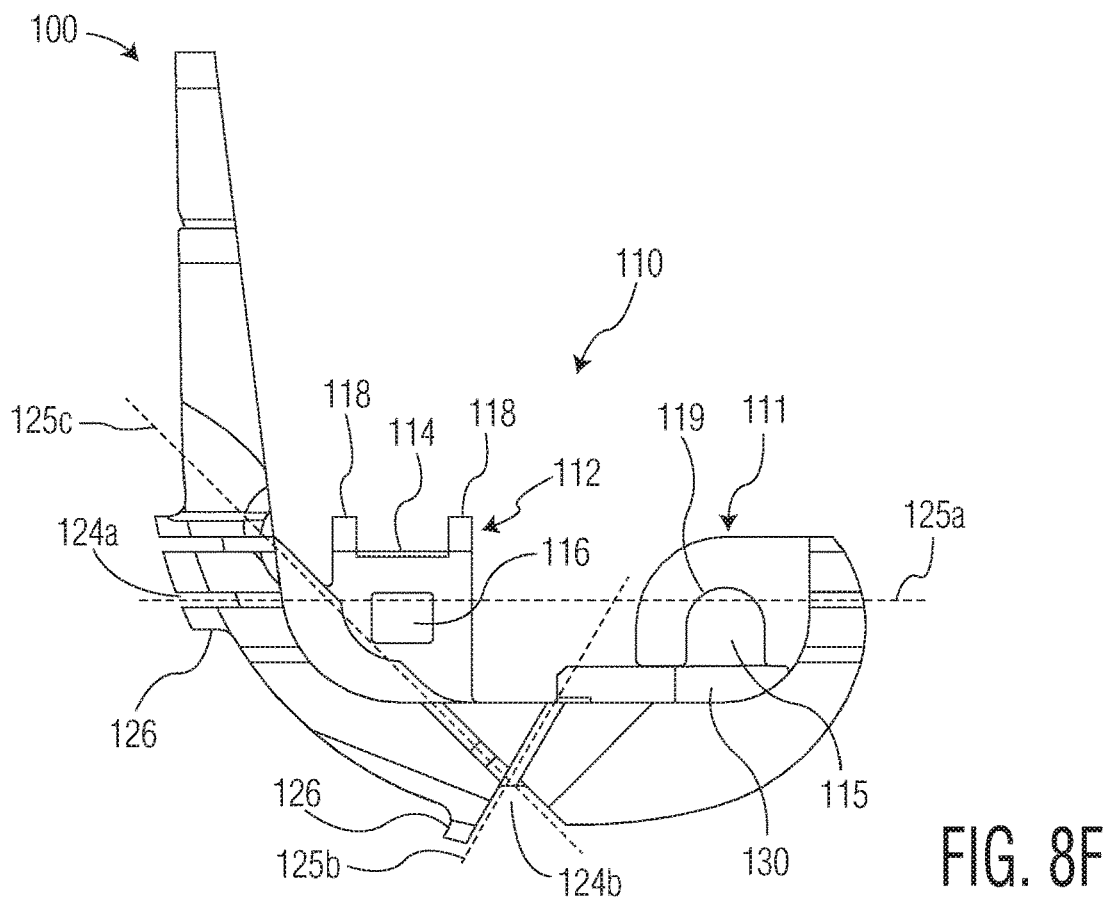
FIG. 8F is a side view of the femoral component trial/guide and locking shuttle of the femoral trial assembly of FIG. 8A, as assembled.
Figure 8G:
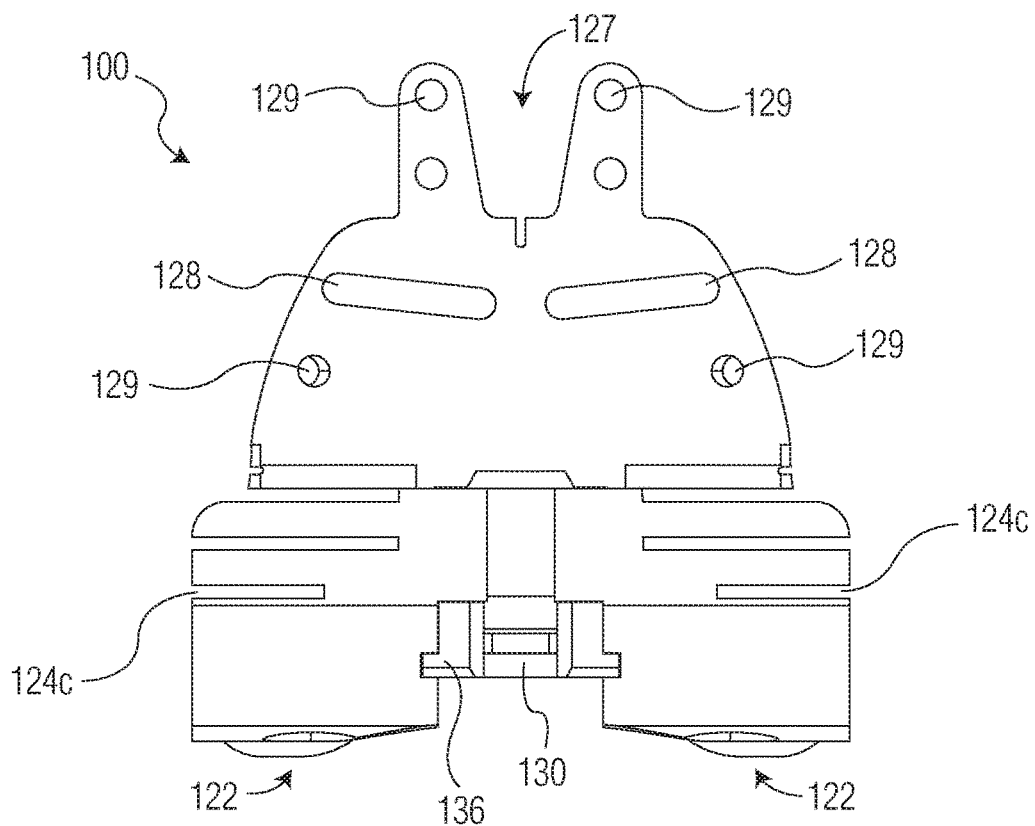
FIG. 8G is a rear view of the femoral component trial/guide and locking shuttle of the femoral trial assembly of FIG. 8A, as assembled.

Locking shuttle 130 is depicted in FIG. 8D and includes a body portion 131 and a pair of legs 132 extending from body portion 131. Legs 132 are separated by a recess 134 and each includes a flange 136 extending outwardly therefrom. These flanges 136 are configured to engage guide grooves 117 of the femoral component 100. In addition, recess 134 is sized and shaped to receive axle support 44. When connected to femoral component 100, as is depicted in FIGS. 8E-8G, locking shuttle 130 slides in an anterior-posterior direction so that in a first position, or anterior position, axle recess 115 is exposed, and in a second position, or posterior position, axle recess 115 is covered by shuttle 130. This helps lock axle 46 to femoral component 100.

Femoral component 100 can be utilized to trial and resect a distal femur in a revision procedure, and also utilized in an oncology procedure where the tibia has a cancerous growth and the femur adjacent the malignant tibia is pristine. In a revision procedure, the target distal femur has already been resected in a previous procedure typically in a five-cut fashion involving a distal, posterior, anterior, anterior chamfer, and posterior chamfer cuts, as is understood in the art. Thus, when femoral component 100 is utilized in a revision procedure, an interior portion or proximal side of femoral component is placed in an interfacing relationship with such resected surfaces. However, the general objective is to convert the five-cut femur to a three-cut femur, as is understood in the art, in order to create space at a posterior side of the distal femur for a hinge assembly of a hinge knee prosthesis. In order for the interior portion of femoral component 100 to conform to the five-cut femur so that it can be resected and transformed to a three-cut femur, the interior portion of femoral component 100 defines a first, second, and third bone contact surfaces 101, 102, 103 where first bone contact surface 101 contacts a posterior resected surface of the femur, second bone contact surface 102 contacts a distal resected surface, and third bone contact surface 103 contacts an anterior resected surface of the revision femur.

Figure 17D:
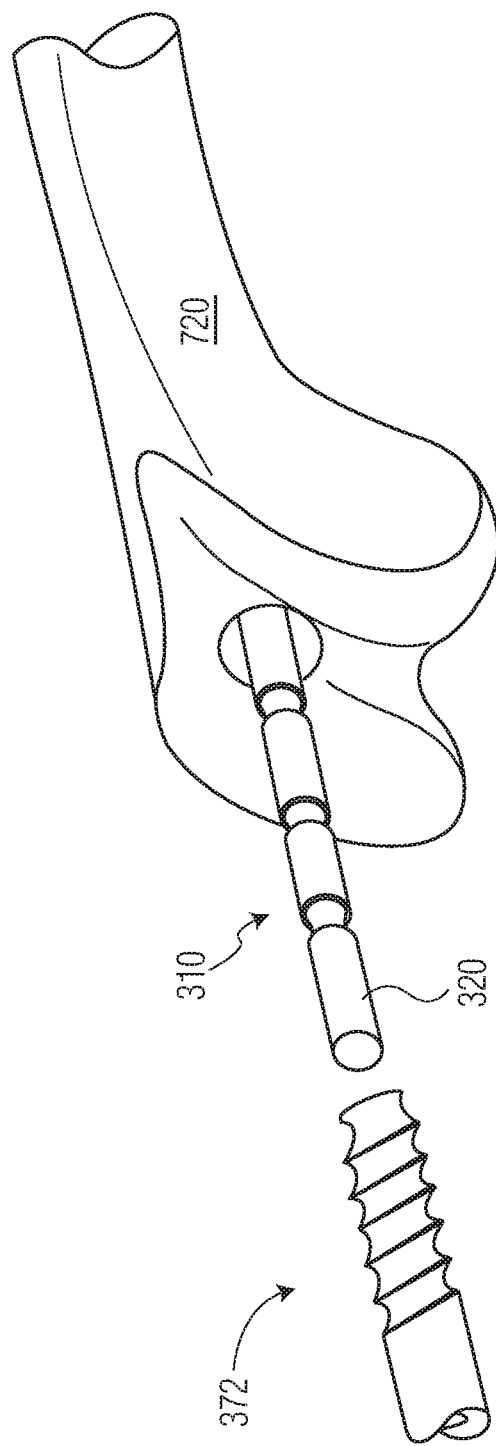
Figure 17E:
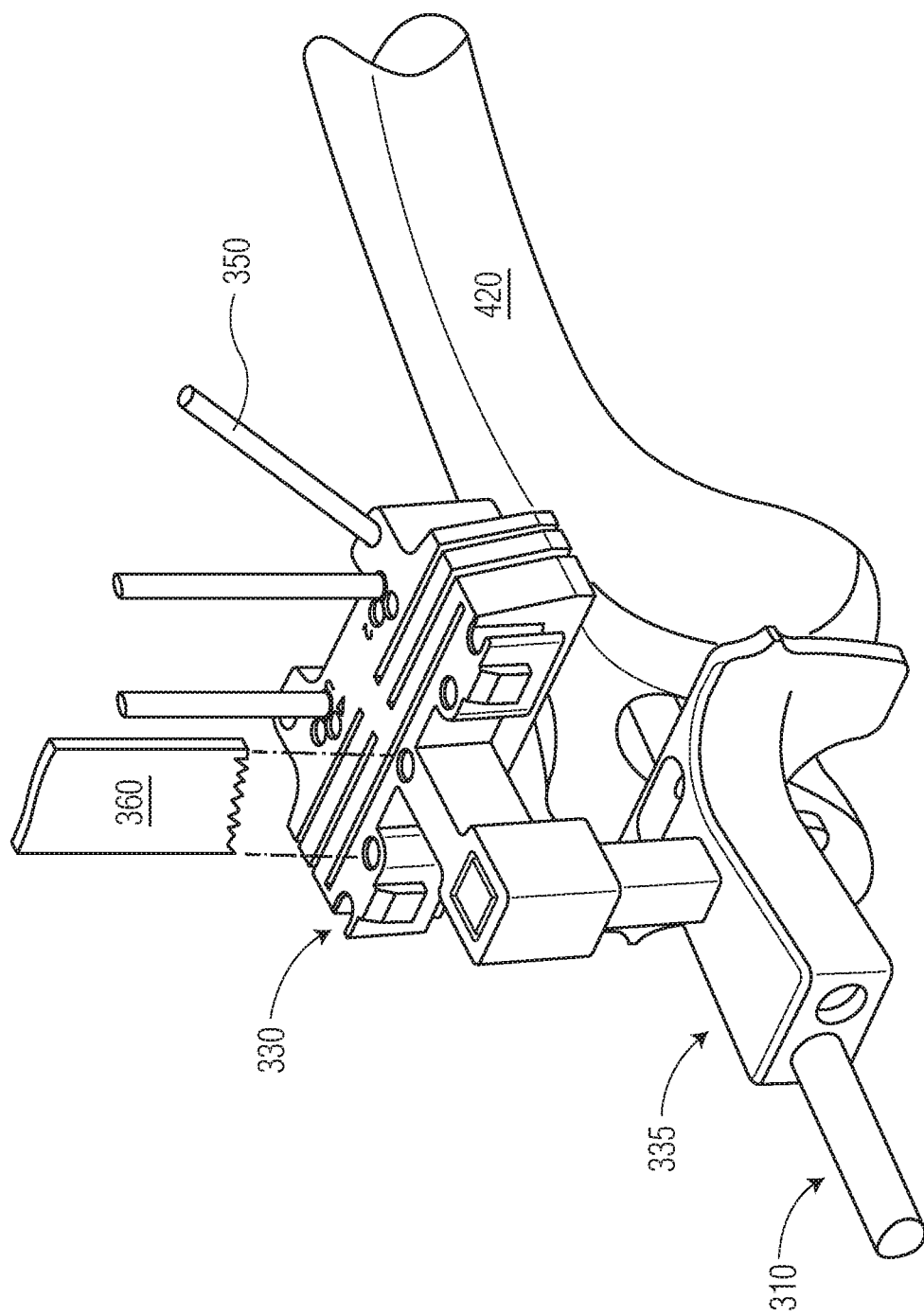
Figure 17F:
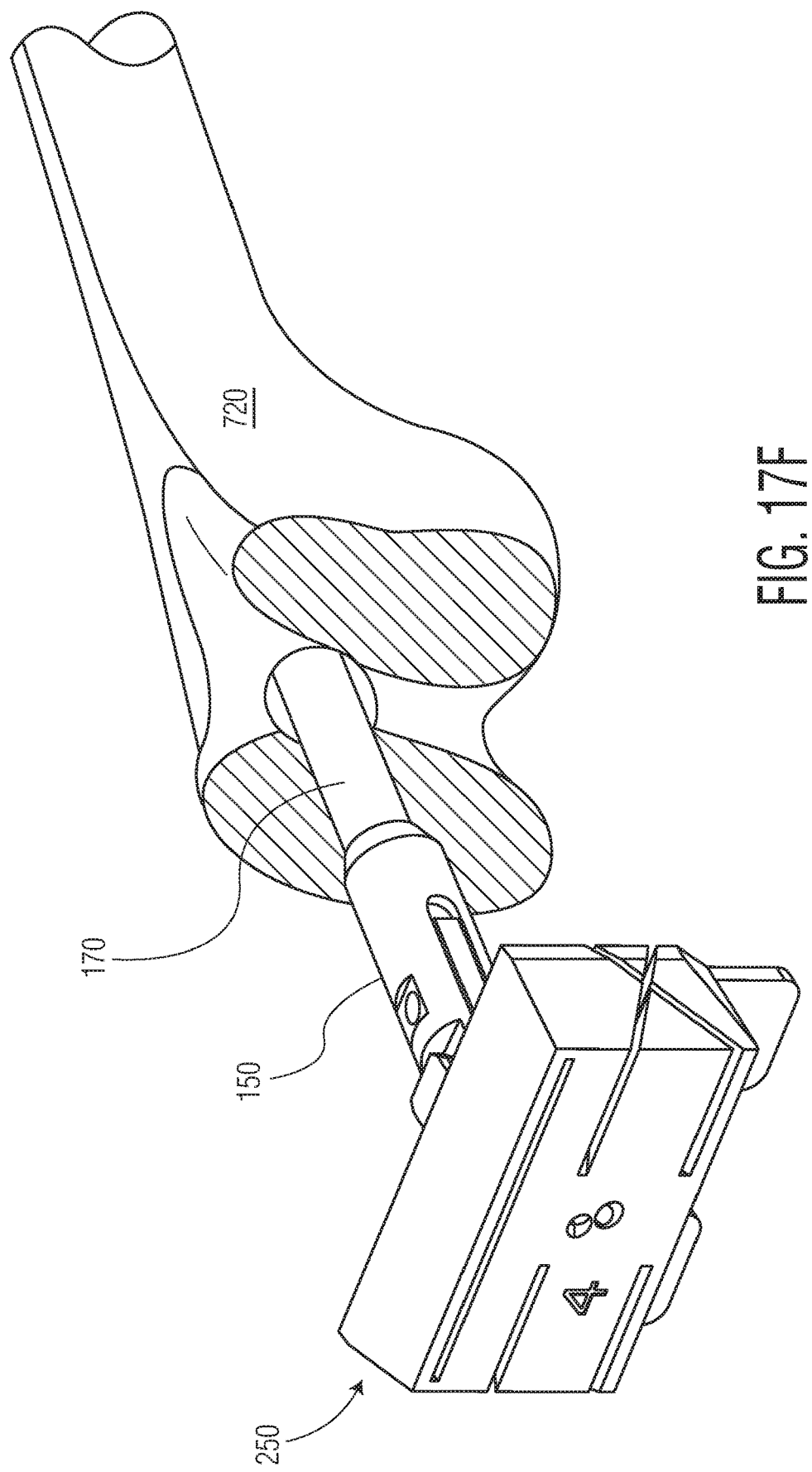
Figure 17G:
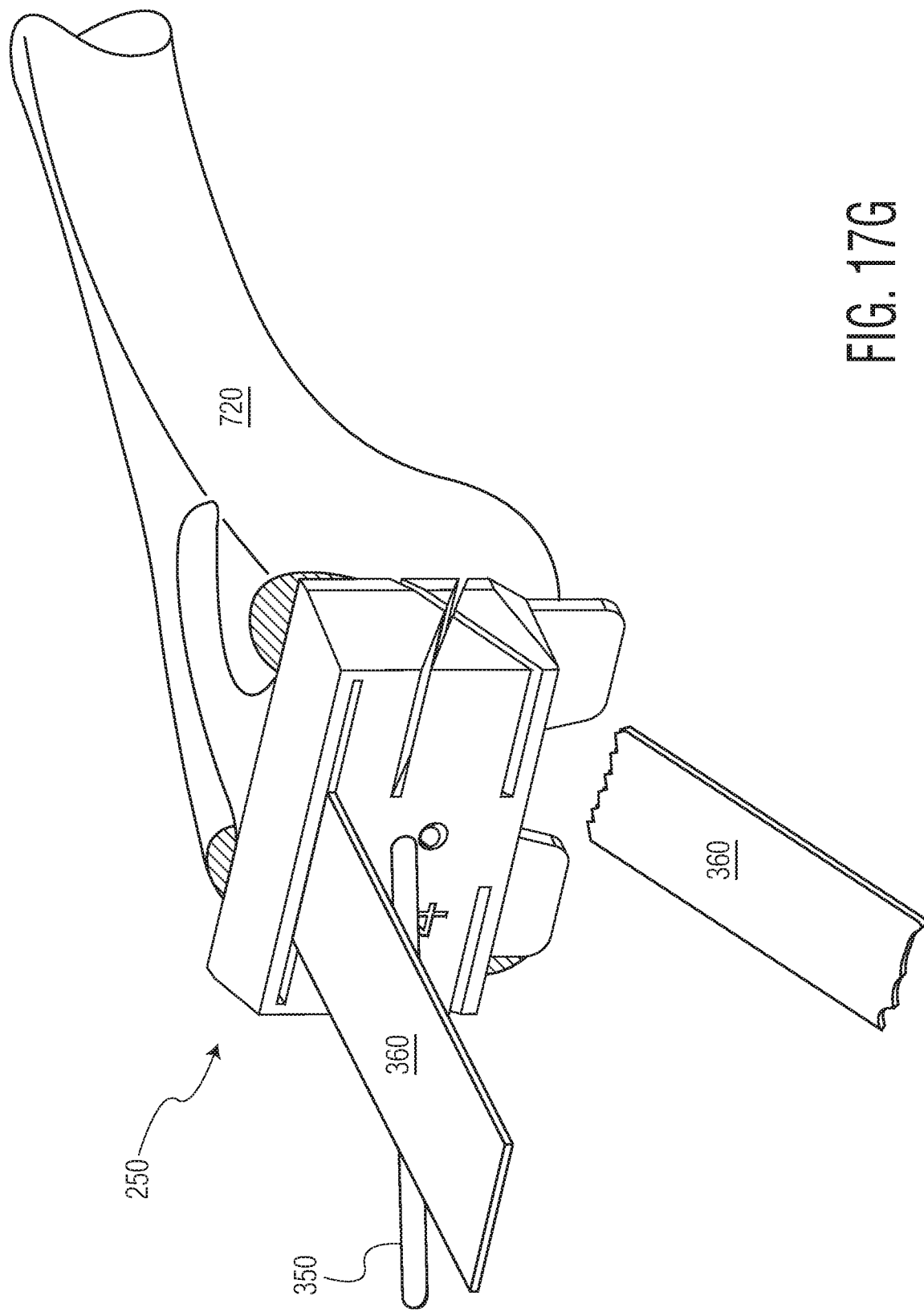
Figure 17H:
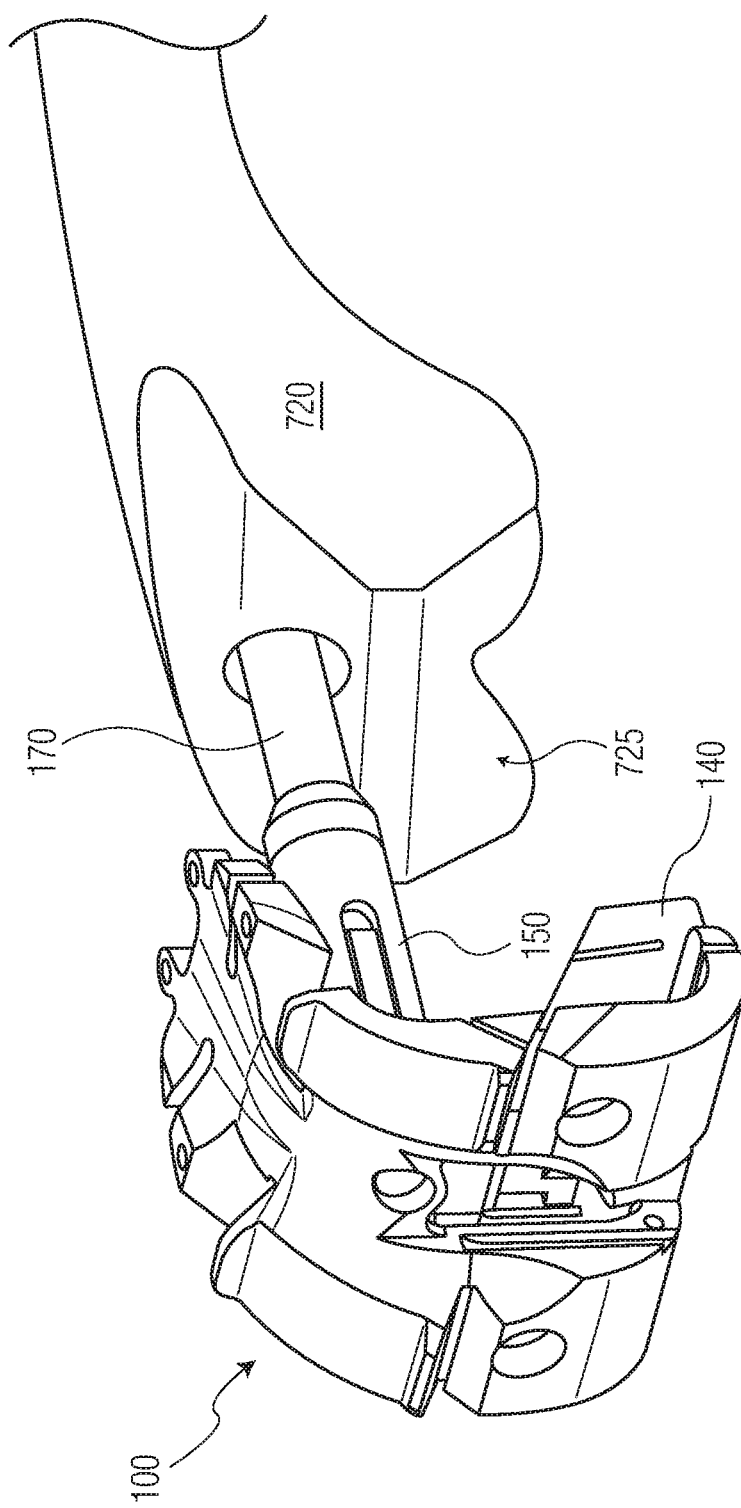

However, as mentioned femoral component 100 can also be utilized in an oncology procedure where a femur is pristine. In other words, the femur is in its natural state and has not been resected in a previous procedure. In this situation, the pristine femur is cut using a distal resection guide 330 and a 3-in-1 cutting block 250 (see FIGS. 17E and 17F) to form the femur into a three-cut femur for receipt of a hinge knee prosthesis. In order to utilize femoral component 100 for such three-cut femur, augment trials 140 are connected to first bone contact surface 101 to create a conforming interior geometry of femoral component 100 that is adapted to the three-cut femur, which allows femoral component 100 to be utilized in both revision and oncology procedures to trial a hinge knee prosthesis. Thus, femoral component 100 has one configuration adapted to be mounted to a five-cut femur, and a second configuration adapted to be mounted to a three-cut femur.

Figure 9A:
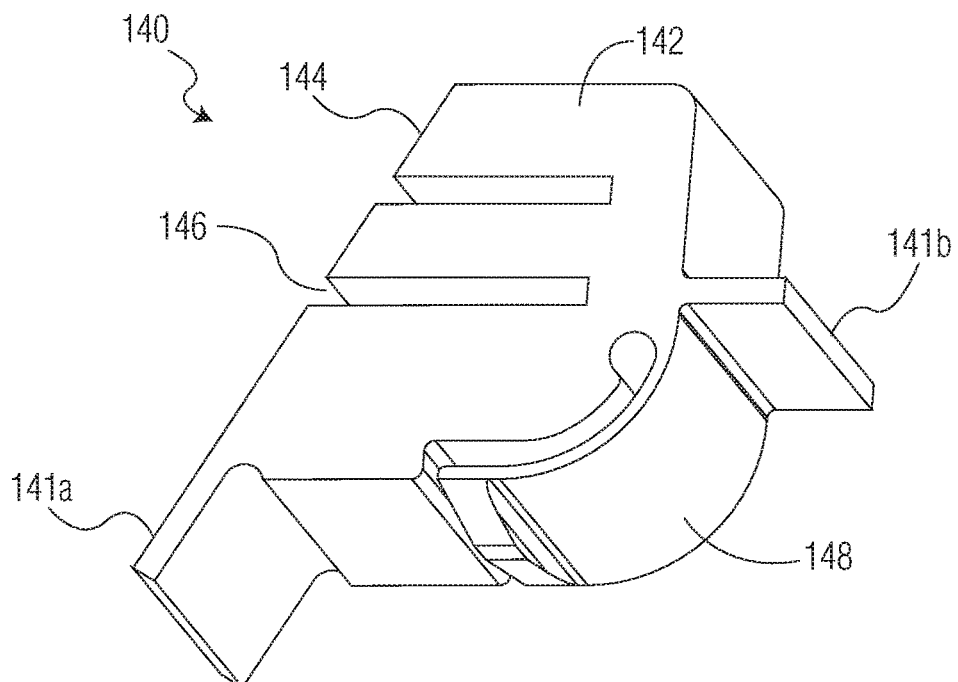
FIG. 9A is a perspective view of the augment trial of FIG. 8A.
Figure 9B:
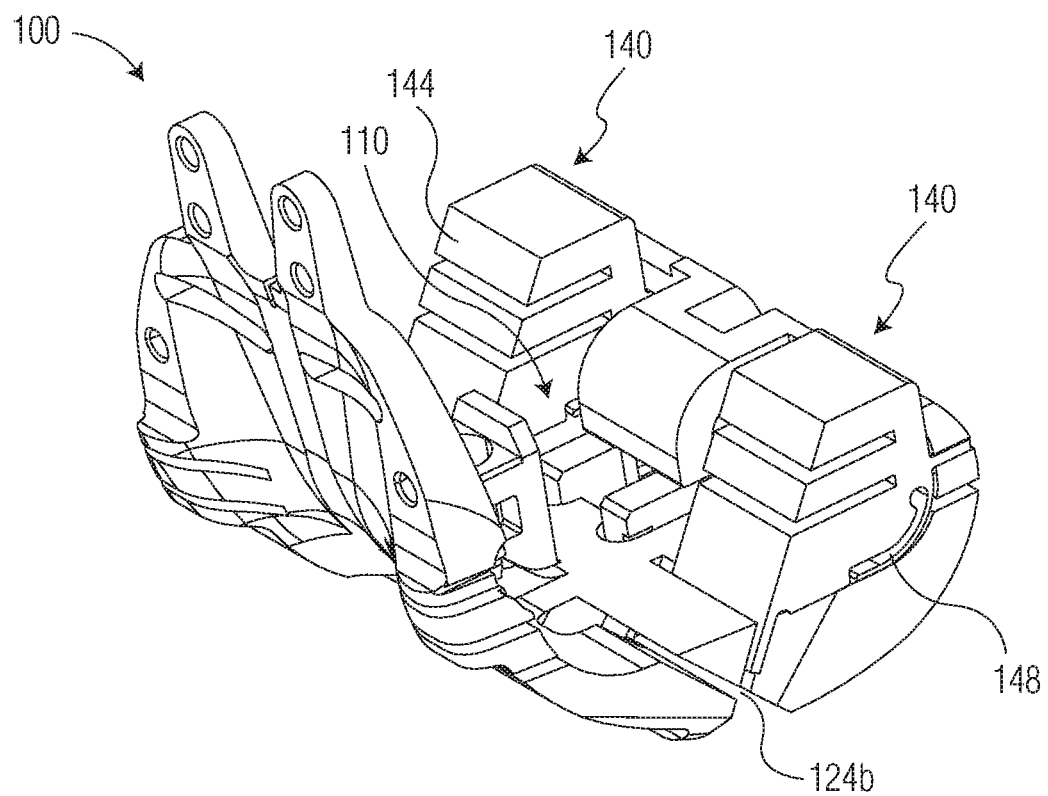
FIG. 9B is a perspective view of the augment trial and femoral component trial guide of the femoral trial assembly of FIG. 8A, as assembled.

Augment trial 140, as depicted in FIG. 9A, includes a body 142, first flange 141a, second flange 141b, and spring member 148. Body 142 is constructed to conform to first bone contact surface 101 and a portion of second bone contact surface 102. In addition, body defines a chamfer surface 144 which takes the place of first bone contact surface 101 when augment trial is connected to femoral component 100. First flange 141a extends from body 142 and aligns with chamfer surface 144. First flange 141a is sized to be received in second cutting slot 124b, as shown in FIG. 9B. Second flange 141b extends from a posterior side of body 142 and is configured to be received in third cutting slot 124c. These flanges 141a-b connect augment trial 140 to femoral component 100. Body 142 also defines a slot 146 which is aligned with flange 141b so that slot 146 operates as a replacement for third resection slot 124c when augment trial is connected to femoral component 100 and second flange is connected to third resection slot 124c. Spring member 148 is disposed between flanges 141a-b. Spring member 148 is cantilevered to body 142 and is curved to conform to an interior of component 100 so that when flanges 141a-b are positioned in their associated resection slots 124a-b, the spring member 148 provides resistance which serves to hold trial 140 in position via frictional engagement between flanges 141a-b and slots 124a-b. Spring member 148 also prevents movement of trial 140 relative to component 100 so that the operator can obtain an accurate assessment of fit.

Figure 10B:
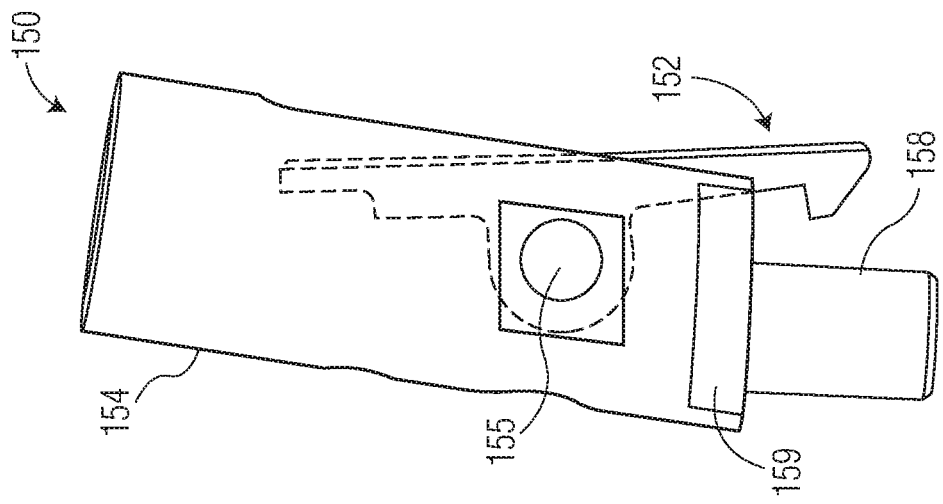
FIG. 10B is a side view of the valgus adaptor of FIG. 8A.
Figure 10A:
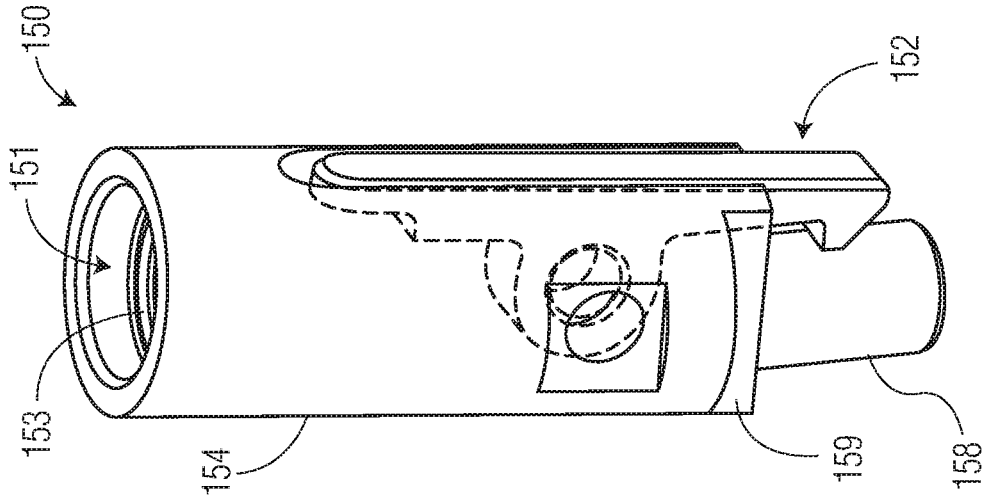
FIG. 10A is a perspective view of the valgus adaptor of FIG. 8A.

FIGS. 10A-10B depict the valgus adaptor 150 which can be used to connect an intramedullary stem (not shown) to femoral component 100 and to also apply a desired valgus angle to femoral component 100 relative to the femur. Valgus adaptor or stem adaptor 150 generally includes a stem connection member 154, a post 158 and a locking pawl 152. Stem connection member 154 is substantially cylindrical and defines an opening 151 that extends along its length. Opening 151 has internal threads 153 for connection to an intramedullary stem. A slot extends through the side of connection member 154. Locking pawl 152 is disposed within this slot and is rotatably connected to connection member 154. The distal end of connection member 154 adjacent post 158 has flat side surfaces 159 that interface with walls 118 of adaptor connection member 112 so as to help prevent rotation of adaptor 150 relative to femoral component 100. Post 158 extends from connection member 154 and has a smaller cross-sectional dimension than connection member 154. Post 158 defines a longitudinal axis that intersects a longitudinal axis of connection member 154 at an oblique angle. This angle may be about 0 to 9 degrees. However, this angle is preferably 6 degrees. Such angle defines the desired valgus angle of femoral component 100 relative to a femur.

Figure 11:
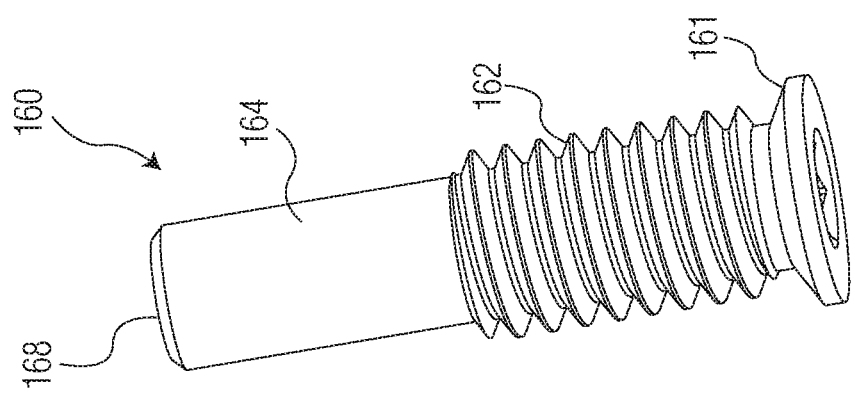
FIG. 11 is a perspective view of a distalizing screw of the femoral trial assembly of FIG. 1.

FIG. 11 depicts distalizing screw 160. Distalizing screw 160 includes a threaded portion 162 and unthreaded portion 164. Threaded portion 162 is configured to threadedly engage a threaded opening 123 of the femoral component 100. Screw 160 has a length sufficient to extend through femoral component 100 and contact a bone surface. Unthreaded portion 164 is at an opposite end of screw 160 from the head 161 of screw 160 and terminates at a flat tip 168. Such flat tip 168 helps push against a bone surface to distract femoral component 100 away from a bone surface, as is described in more detail below.

As mentioned above, femoral trial assembly 14 has a first configuration adapted to mount to a five-cut femur, such as for a revision procedure. In such assembly, distalizing screws 160 are threaded into threaded openings 123, and valgus adaptor 150 is connected to adaptor connection member 112. In this regard, post 158 extends into post opening 114, locking pawl 152 is connected to latch opening 116, and sidewalls 118 interface with surfaces 159. It is noted that latch opening 116 extends entirely through connection member 112 so that valgus adaptor 150 can be connected in two different orientations depending on which leg femoral component 100 is mounted to. In this regard, femoral component 100 is universal to both a right and left leg of a patient.

In the second configuration of femoral trial assembly 14, which is adapted for mounting to a three-cut femur, valgus adaptor 150 is connected to connection member 112 in the same manner as in the first configuration, and augment trials 140 are additionally connected to femoral component 100, as is shown in FIG. 8A. In this regard, two augment trials 140 are connected to opposite sides of femoral component 100 so that chamfer surface 144 faces anteriorly and first and second flanges 141a-b thereof engage respective second and third cutting slots 124b-c.

Figure 12B:
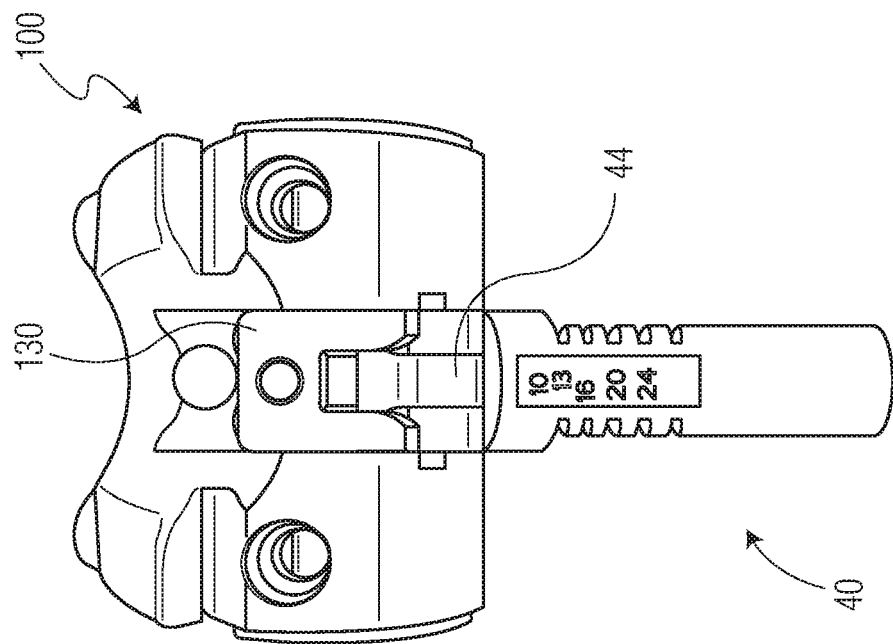
FIG. 12B is a front view of the femoral trial assembly and intercondylar axle component of the assembly of FIG. 1, as assembled in a second configuration.
Figure 12A:
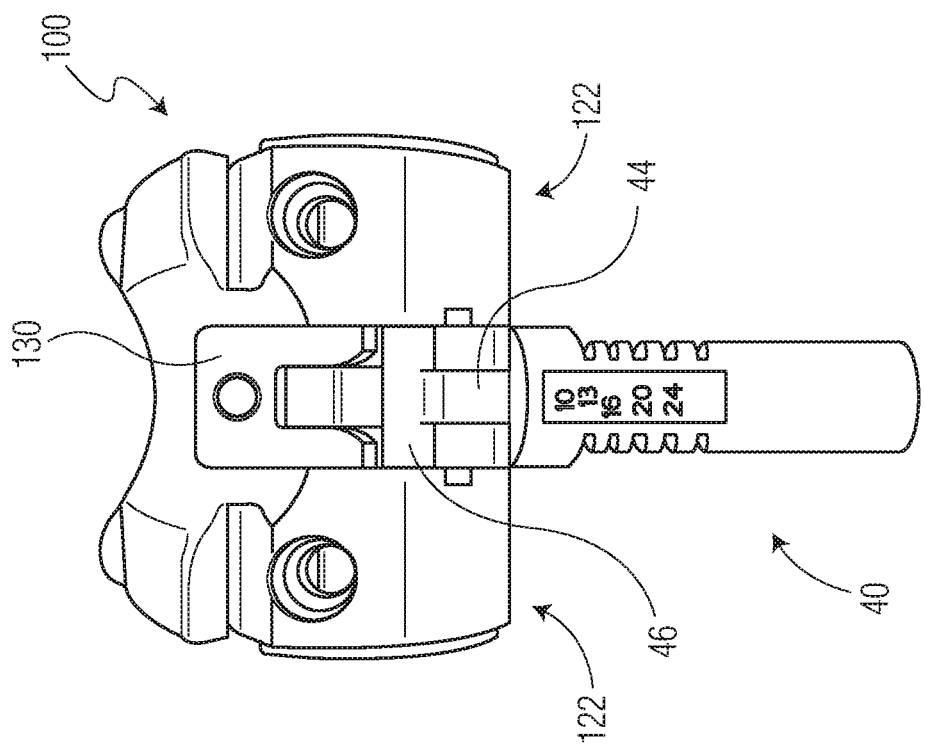
FIG. 12A is a front view of the femoral trial assembly and intercondylar axle component of the assembly of FIG. 1, as assembled in a first configuration.

Femoral trial assembly 14 can be connected to tibial trial assembly 12 via axle member 40. In this regard, locking shuttle 130 is located at its anterior position to expose axle recess 115. Axle 46 is passed through an intercondylar space between first and second condylar portions 122 and into recess 115, as shown in FIG. 12A. The length of axle 46 is such that axle 46 can pass through this space lengthwise. When axle 46 is inserted into recess 115, axle support 44 is located in posterior notch 113 allowing unimpeded freedom of rotation of axle component 40 relative to femoral component 100. To help retain axle 46 within recess 115, locking shuttle 130 is slid into its posterior position so that legs 132 at least partially extend over axle 46, as shown in FIG. 12B. Recess 134 provides clearance for axle support 44 when axle component 40 is rotated relative to femoral component 100 through flexion and extension.

Tibial trial assembly 12 can be utilized to trial a tibia in a revision procedure, and also utilized in an oncology procedure where a femur has a cancerous growth and the tibia adjacent the malignant femur is pristine. In such an oncology procedure, a significant portion of a patient's femur may be removed leaving only a portion of the femur's diaphysis at the femur's distal end. In this regard, femoral trial assembly 14 cannot be used in conjunction with tibial trial assembly as there would be no bone for assembly 14 to connect. However, an alternative femoral trial may be utilized.

Figure 13:
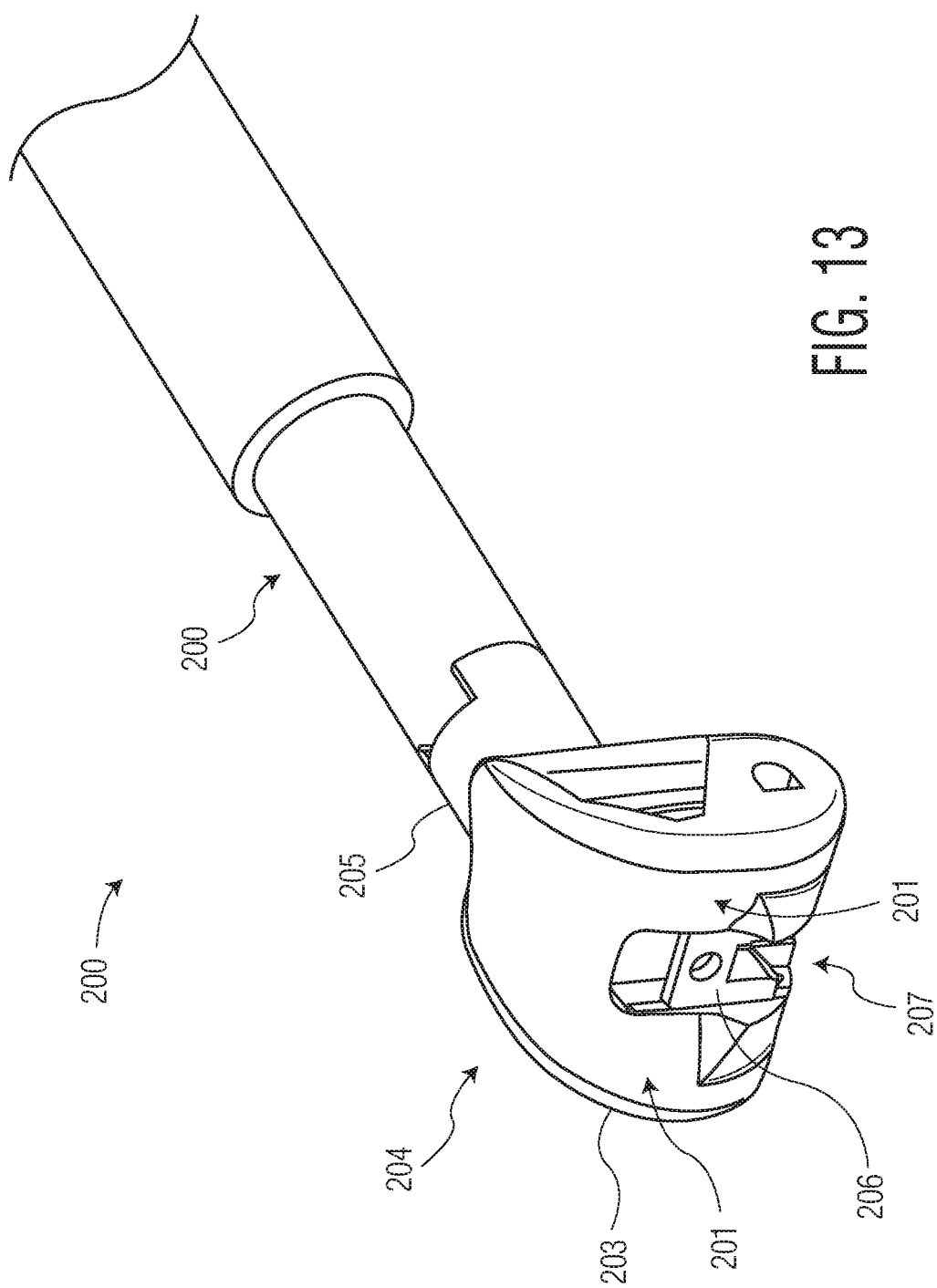
FIG. 13 is a perspective view of a femoral oncology trial according to an embodiment of the present disclosure.

FIG. 13 depicts a femoral oncology trial 200 which may be used as an alternative to femoral trial assembly 14 for femoral oncology procedures. Trial 200 includes a distal femoral component 204 and a diaphyseal extension member 202. Distal femoral component 204 includes a metaphyseal portion 203 and a diaphyseal portion 205. Diaphyseal portion 205 extends from metaphyseal portion 203 and is configured to connect to a resected diaphysis of a femur or, alternatively, to diaphyseal extension member 202. Metaphyseal portion 203 defines condylar portions 201 and an intercondylar portion 207. Intercondylar portion 207 is similar to intercondylar portion 110 in that it includes an axle recess, anterior notch and locking shuttle 206. This allows femoral oncology trial 200 to be connected to tibial trial assembly 12 in the same fashion as femoral trial assembly 14.

Figure 17I:
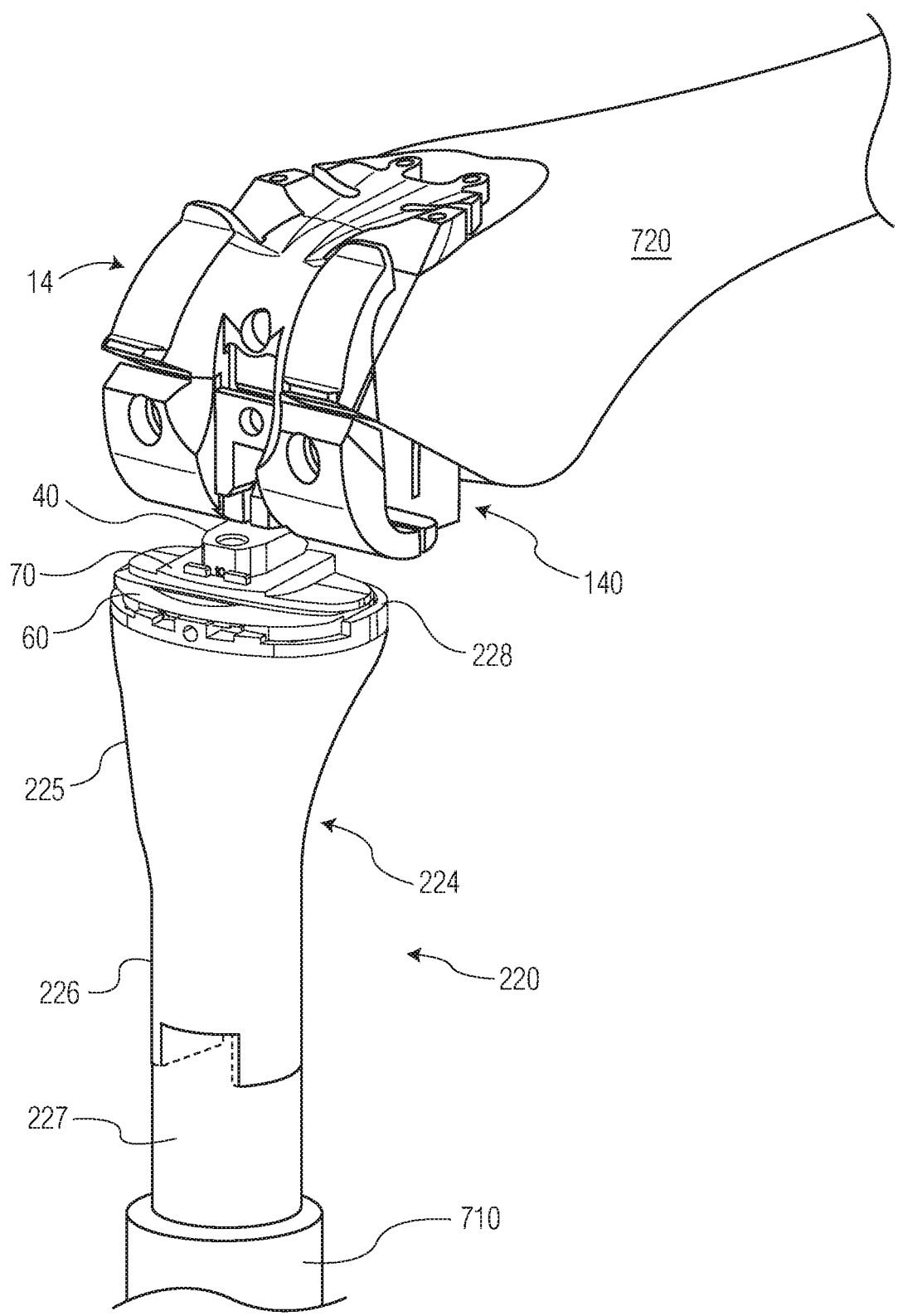
Figure 17J:
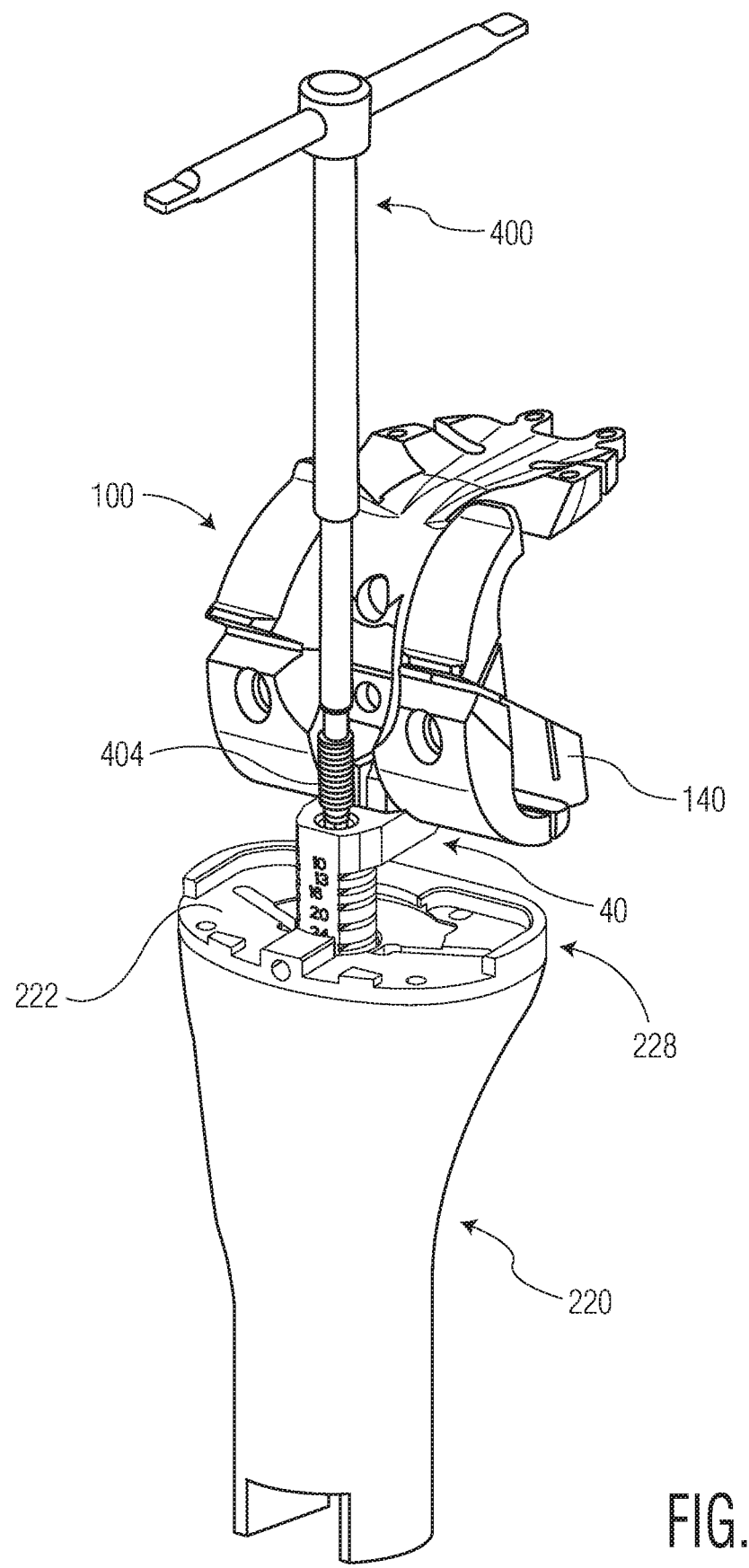

In other oncology procedures where a tibia has a cancerous growth, tibial trial assembly 12 cannot be utilized as the patient's proximal tibia may be completely removed to eliminate the cancerous growth. However, alternatives may be utilized that can operate in conjunction with femoral trial assembly 14 or femoral oncology trial 200. One such alternative is tibial oncology trial 220 depicted in FIG. 17I. Tibial oncology trial 220 includes a proximal tibial component 224 and a diaphyseal extension member 227. Proximal tibial component 224 includes a metaphyseal portion 225 and a diaphyseal portion 226. Diaphyseal portion 226 extends from metaphyseal portion 225 and is configured to connect to a resected diaphysis of a tibia or, alternatively, to diaphyseal extension member 227. Metaphyseal portion 225 defines a tray portion 228 at its proximal end that is configured to receive tibial insert 60. In addition, metaphyseal portion 225 defines a boss opening (not shown) that is configured to receive boss of axle component 40 so that tibial oncology trial 220 can operate in a similar fashion to that of tibial trial assembly 12.

Figure 14A:
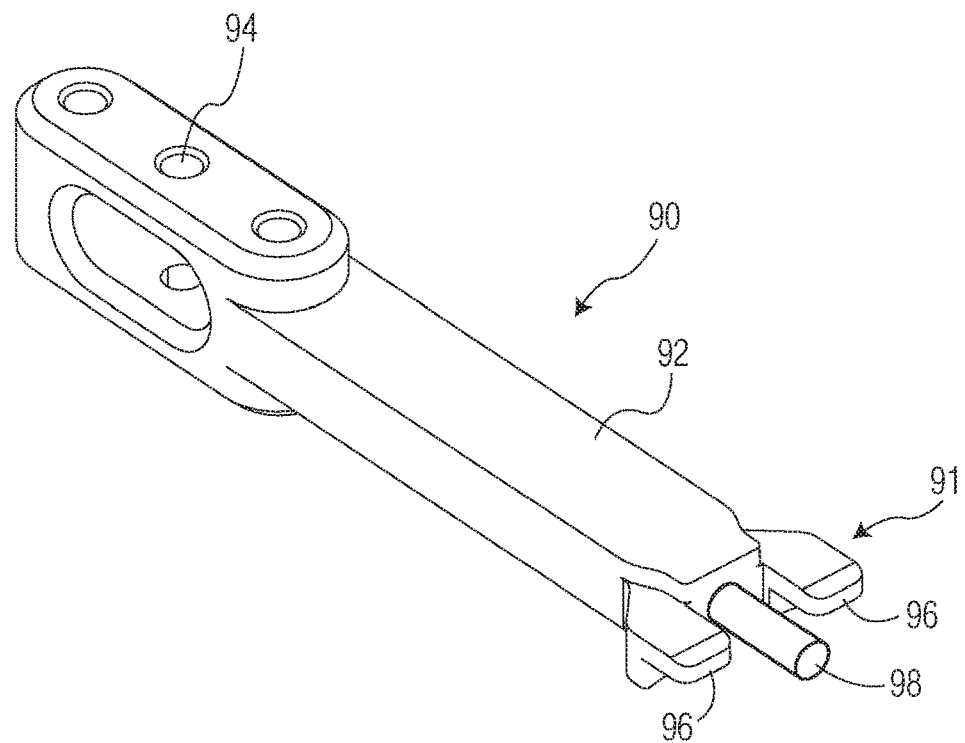
FIG. 14A is a perspective view of an alignment handle according to an embodiment of the present disclosure.
Figure 14B:
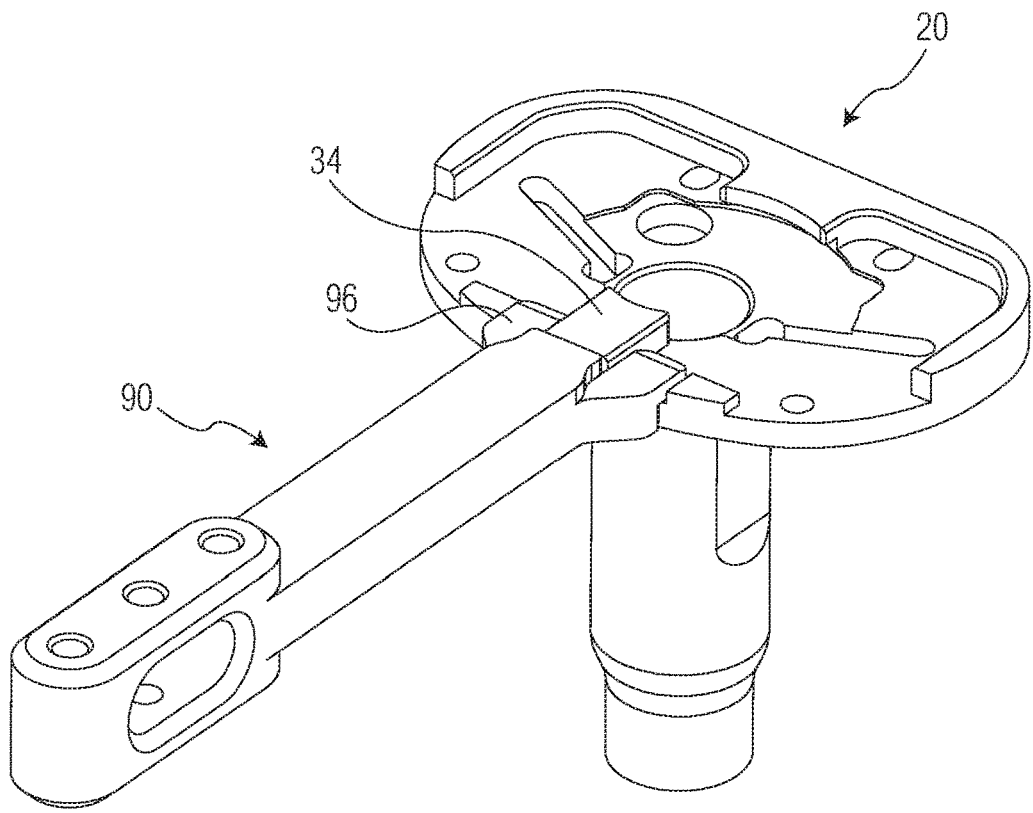
FIG. 14B is a perspective view of the alignment handle in engagement with the tibial baseplate trial of FIG. 2A.

Other instruments may be utilized in conjunction with hinge knee trial assembly 10. For example, FIGS. 14A and 14B depict an alignment handle 90. Alignment handle 90 can be used to assess alignment of baseplate component 20 relative to a patient's tibia. Handle 90 includes an elongate body 92 and an engagement end 91. Openings 94 extend through elongate body 92 and are configured to receive an extramedullary rod. Engagement end 91 includes stabilizing flanges 96 and a cylindrical projection 98. Cylindrical projection 98 is configured to extend into anterior opening 36 of baseplate component 20 while flanges 96 contact proximal plate surface 32 to orient and stabilize handle 90 to prevent handle 90 from rotating, as shown in FIG. 14B.

As mentioned above, hinge knee trial assembly 10 and the various components thereof, may be utilized in various different surgical procedures, such as revision procedures and oncology procedures. However, it should be understood that such devices could be utilized in other procedures, such as in a primary TKA, in which a hinge knee prosthesis is to be implanted.

Figure 15A:
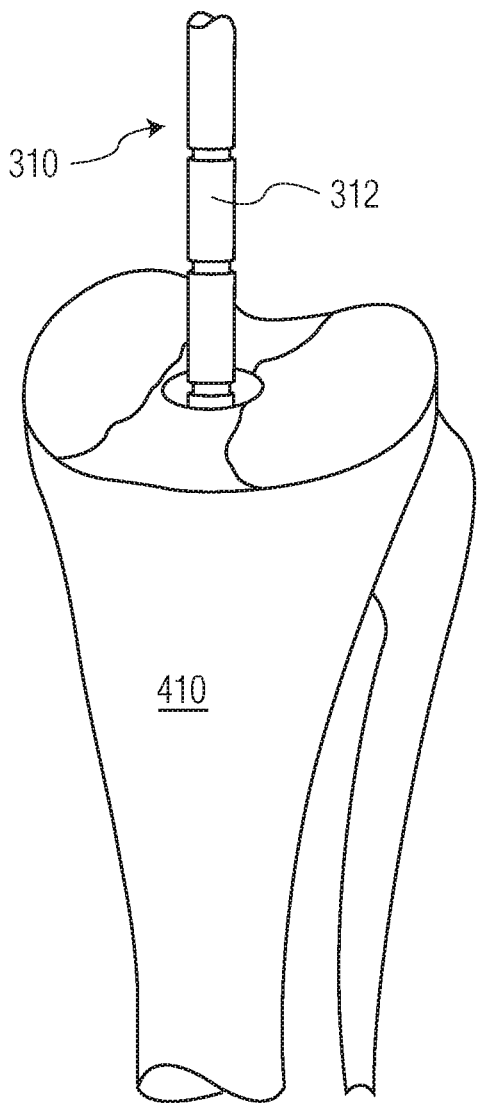
FIGS. 15A-15N depict a method of preparing a femur and tibia for a hinge knee prosthesis in a revision procedure according to an embodiment of the present disclosure.
Figure 15C:
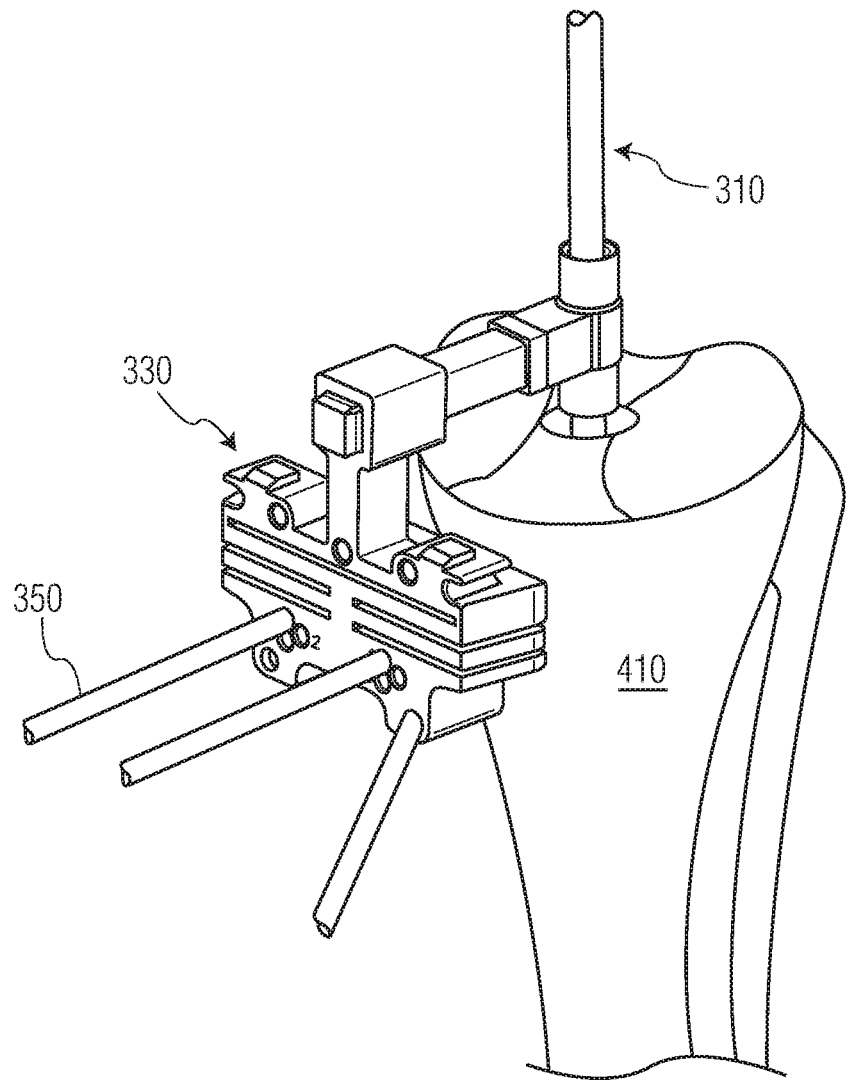
Figure 15D:
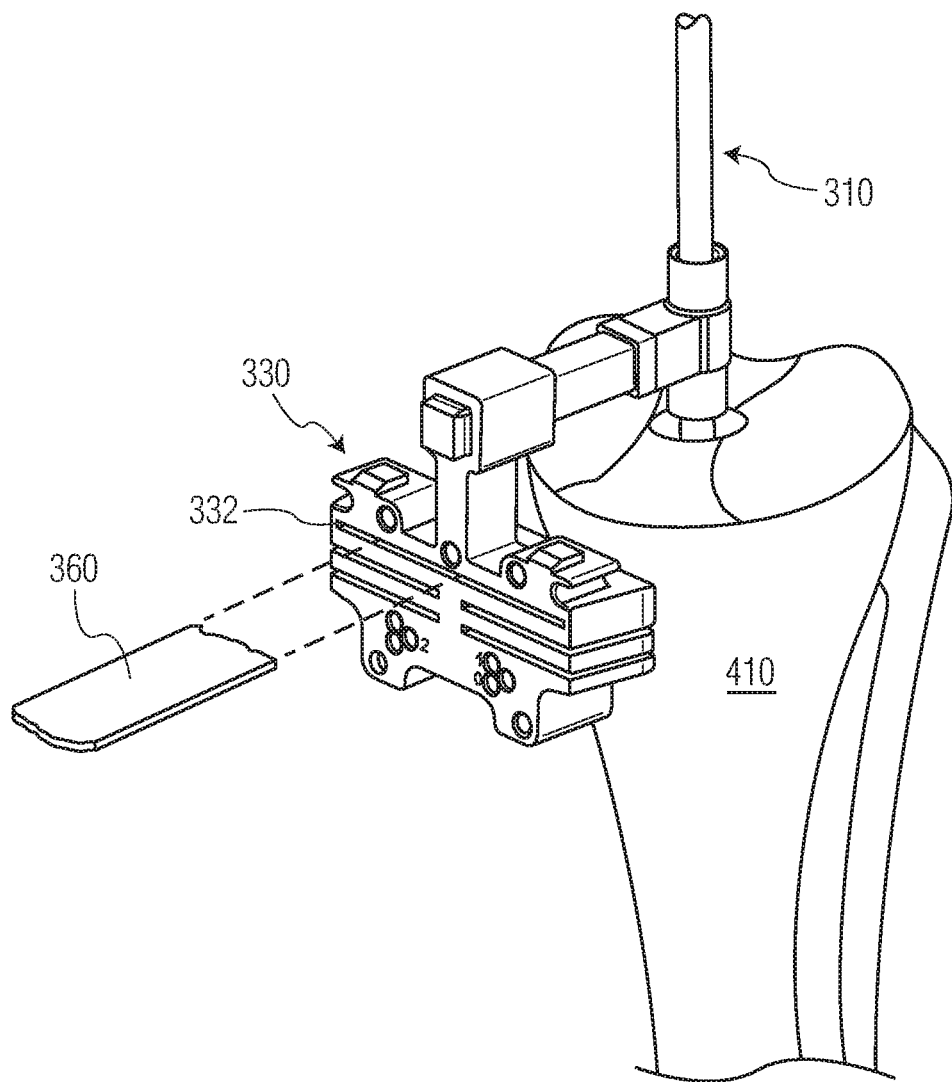
Figure 15E:
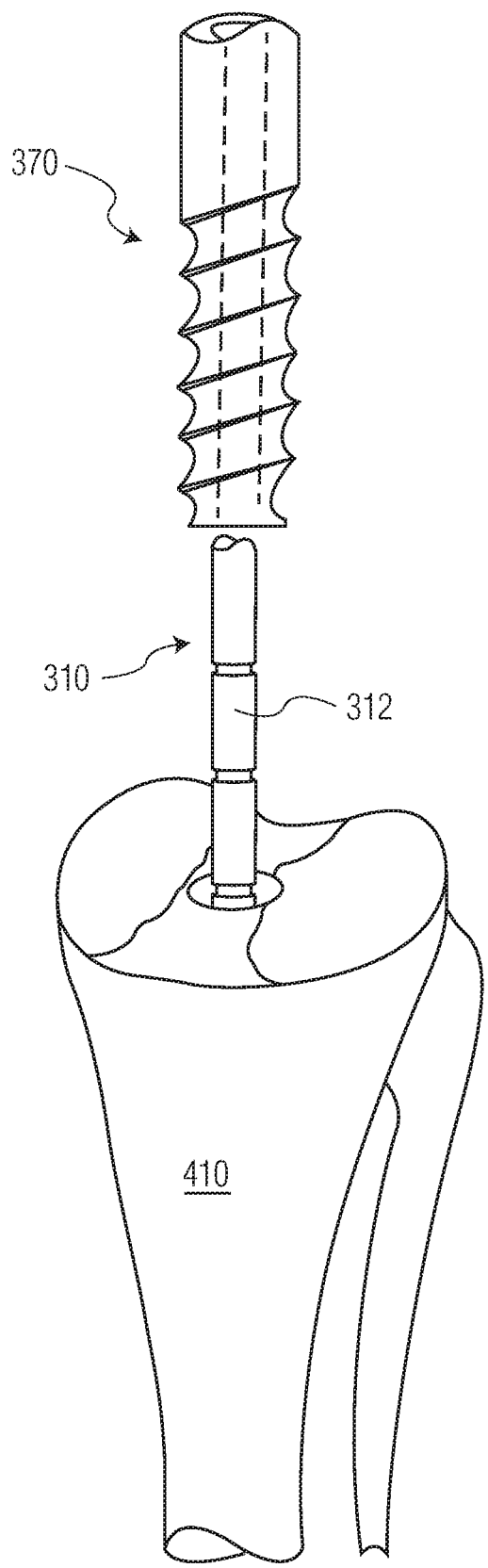
Figure 15F:
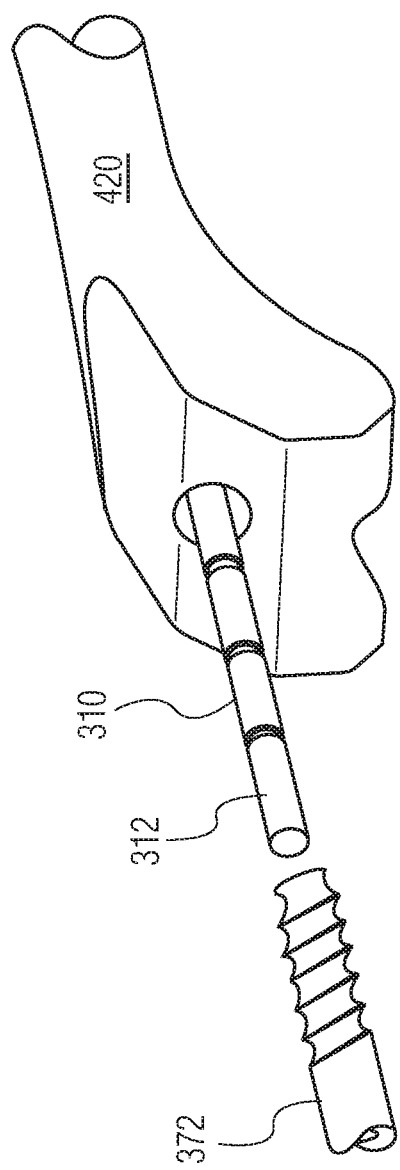
Figure 15G:
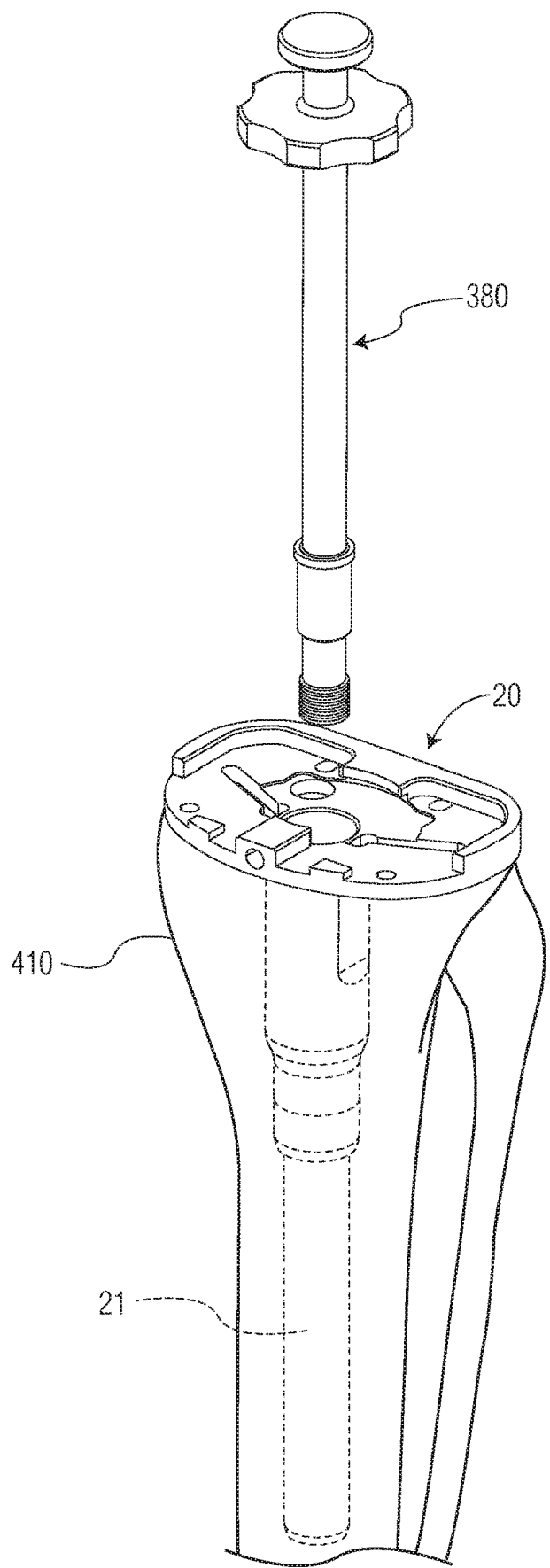
Figure 15H:
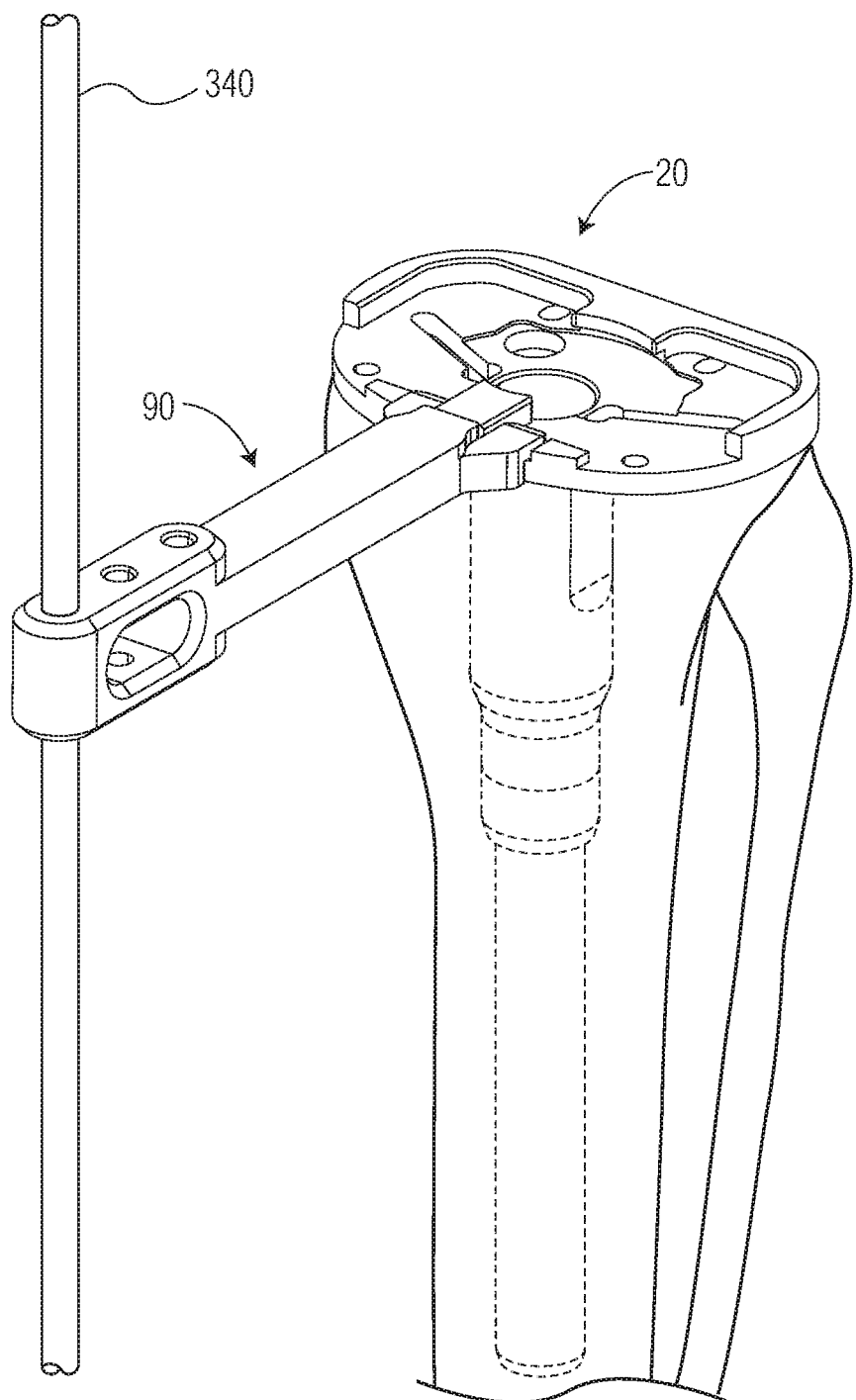
Figure 15I:
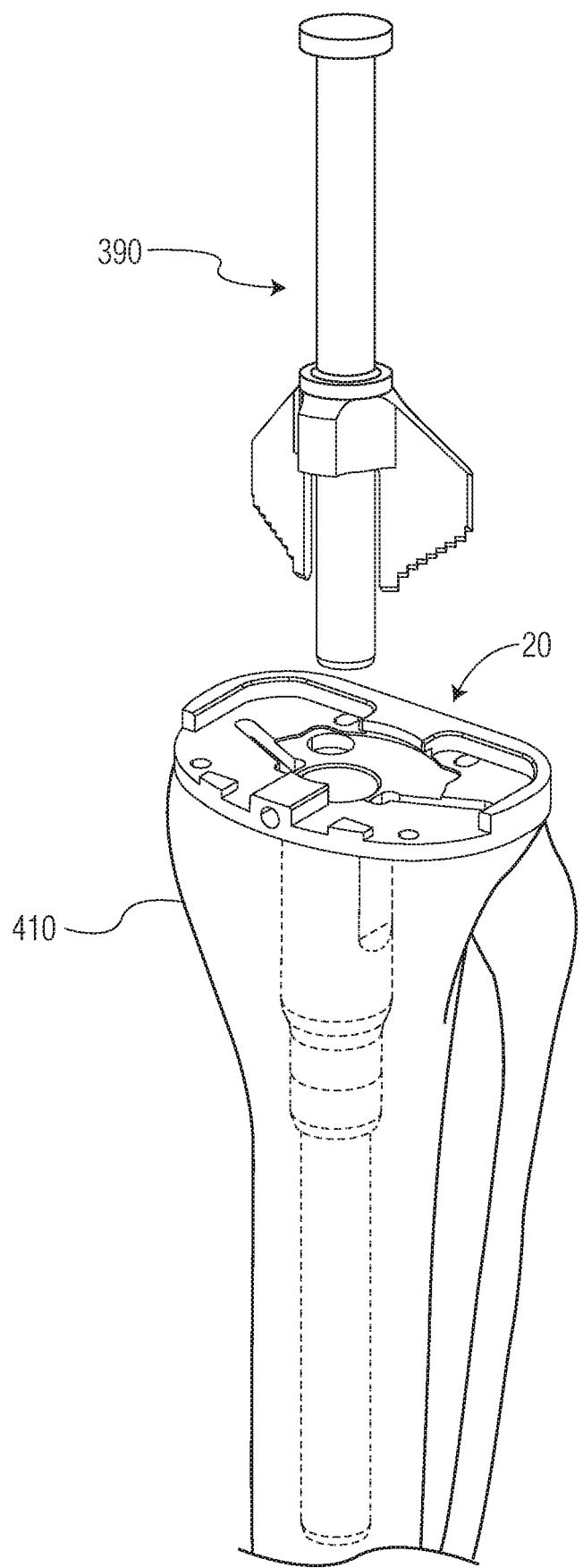
Figure 15J:
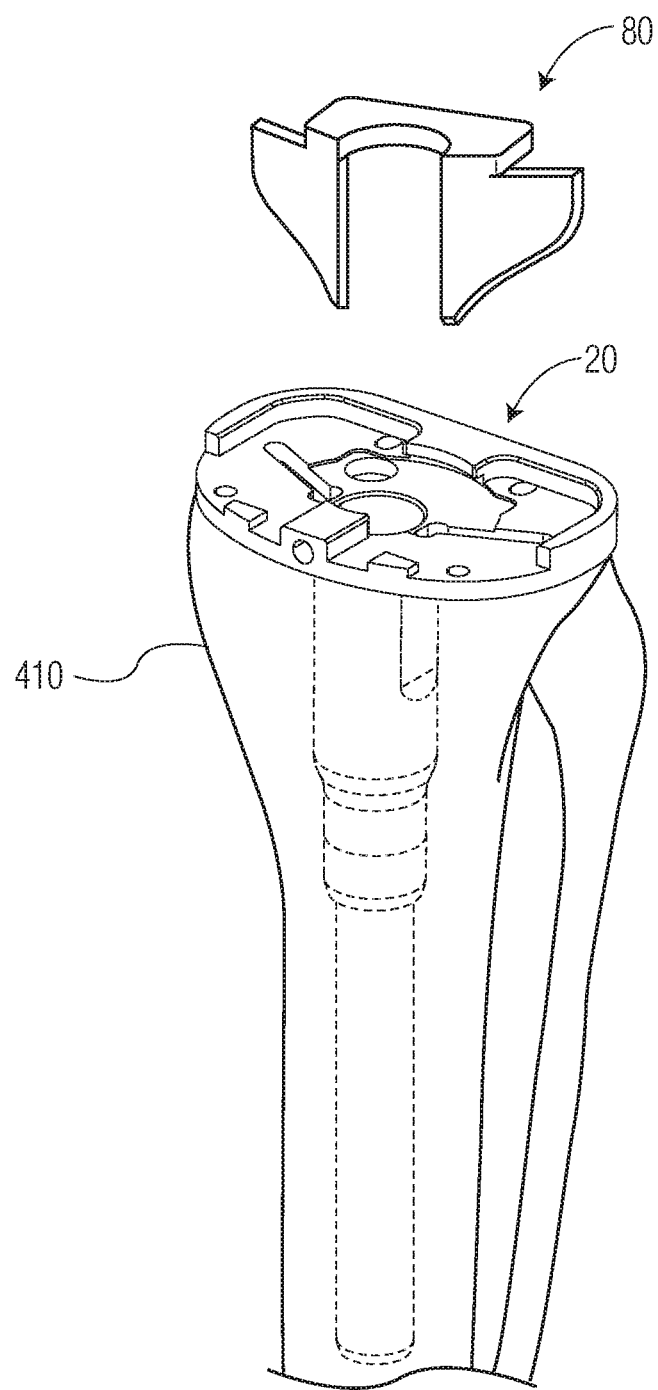
Figure 15K:
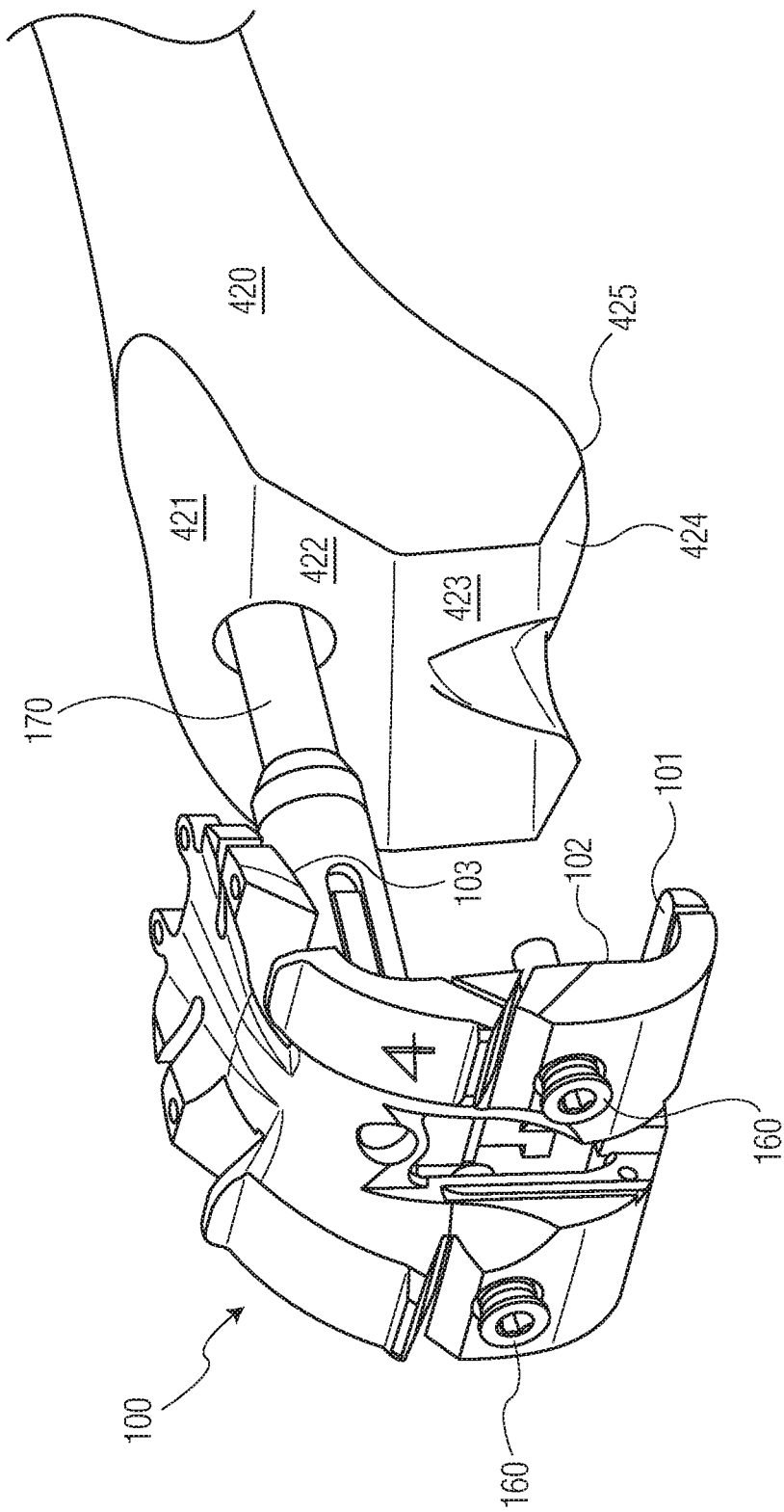
Figure 15L:
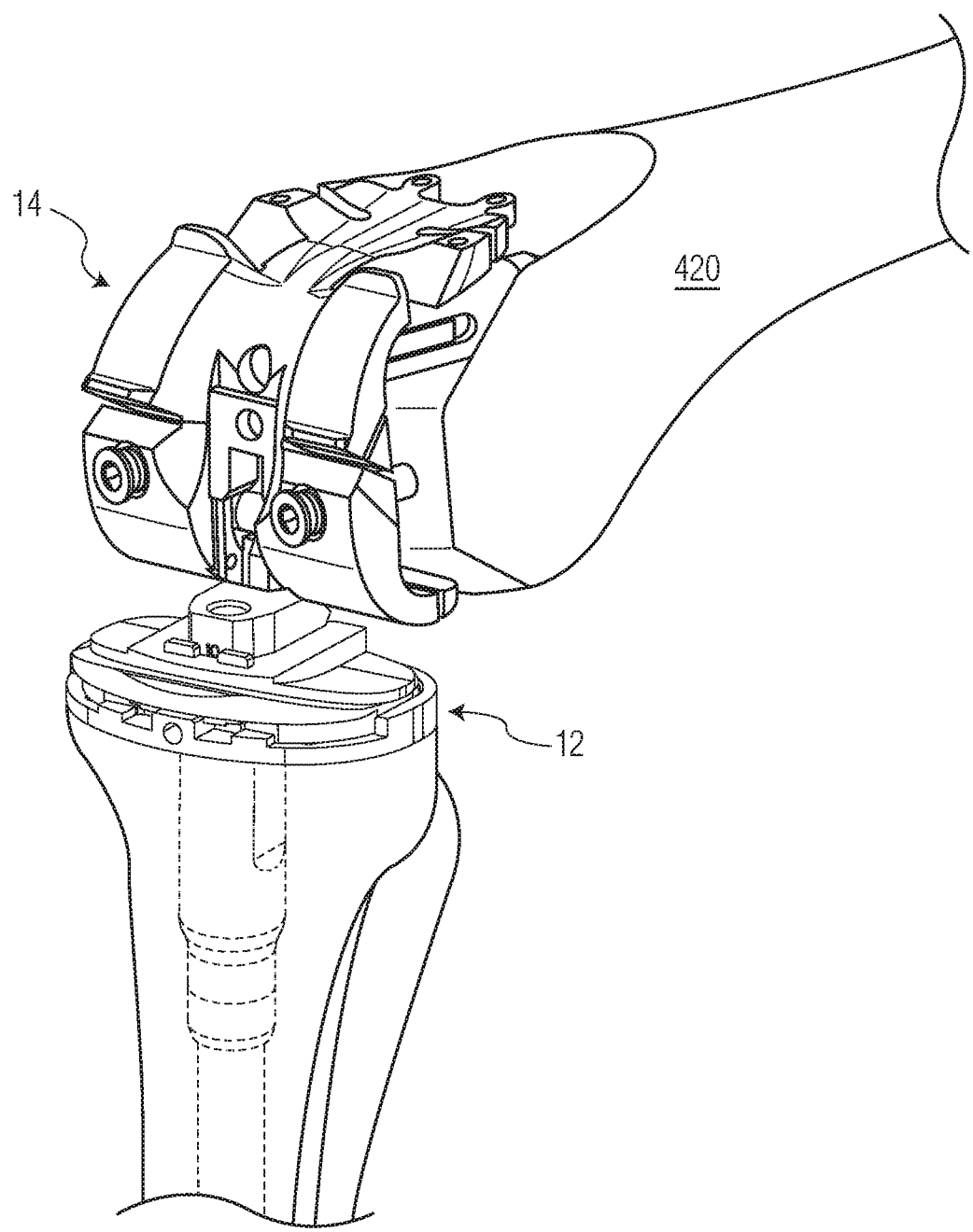
Figure 15N:
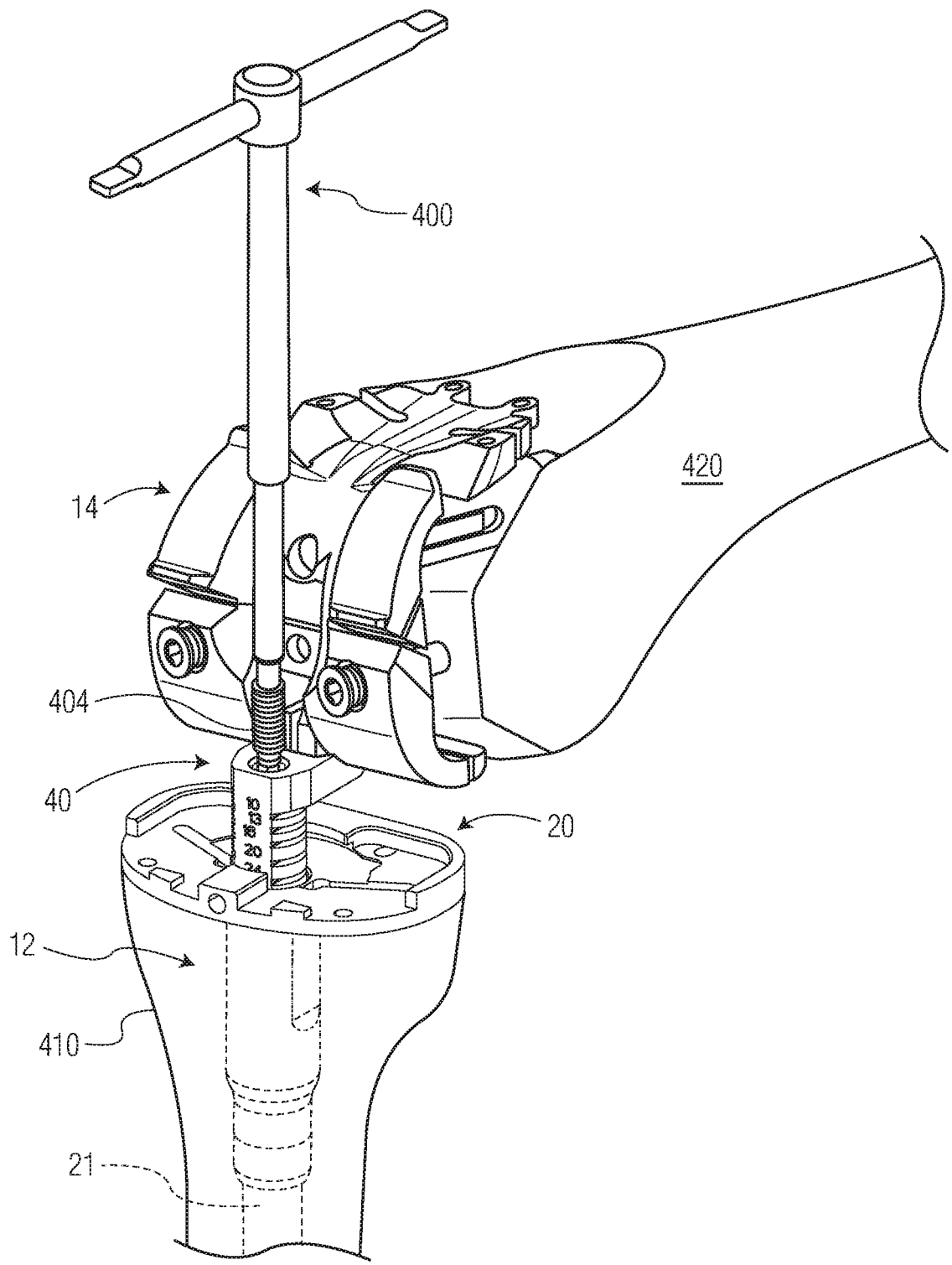

FIGS. 15A-15N illustrate a method of preparing a knee joint utilizing hinge knee trial assembly 10 in a revision procedure. In the method, after an operator gains access to the patient's knee joint, a previously implanted prosthesis is removed from a femur 420 and tibia 410 to expose the proximal tibia and distal femur. As is typically the case in a revision procedure, the proximal tibia and distal femur have resected surfaces which were formed in the previous procedure in which the previous prosthesis was implanted. In this regard, the tibia 410 has a resected proximal surface. In addition, femur 420 may be a five-cut femur in which femur 420 has anterior, anterior chamfer, distal, posterior chamfer, and posterior resected surfaces 421-425, as best shown in FIG. 15K.

Once the previously implanted prosthesis is removed, tibia 410 is prepared to receive tibial trial assembly 12. In this regard, fluted reamers are sequentially advanced into the intramedullary canal leaving the last reamer 310 in situ so that a shank 312 of reamer 310 extends from the proximal tibia (see FIG. 15A). Thereafter, a resection jig 330 is assembled to reamer shank 312 so that a resection slot 332 of resection jig 330 is placed adjacent to tibia 410 (see FIG. 15B). The rotational alignment of cutting jig 330 is verified by connecting alignment handle 90 to jig 330 which is achieved by inserting cylindrical projection 98 into a corresponding opening 334 of resection jig and placing stabilizing flanges 96 on respective surfaces 336 of jig 330. An extramedullary rod 340 is inserted through opening 94 in handle 90 and is used to reference the alignment of resection slot 332 relative to an axis of tibia 410. When the desired alignment is achieved, jig 330 is pinned to tibia 410 (see FIG. 15C) via bone pins 350, and a saw 360 is inserted through resection slot 332 to perform a clean-up skim cut of the proximal tibia (see FIG. 15D). If necessary, appropriate augment cuts may be performed through other resection slots in jig 330. Thereafter, jig 330 is removed from shank 312 of intramedullary reamer 310 and a cannulated boss reamer 370 reams into tibia over shank 312 so as to form a bone void for receipt of boss 22 of tibial baseplate 20 (see FIG. 15E). Reamer 310 is then removed.

Femur 420 is also prepared so that it can receive femoral trial assembly 14. In this regard, fluted reamers are sequentially advanced into the intramedullary canal of the femur leaving the last reamer 310 in situ so that shank 312 of reamer 310 extends from the distal femur (see FIG. 15F). A cannulated boss reamer 372 reams femur 420 over shank 312 so as to form a void for valgus adaptor 150. Reamer 310 is then removed from femur 420.

Once tibia 410 is prepared, a stem trial 21 is connected to baseplate component 20 by threading stem trial 21 to internal threads 24 of baseplate boss 22. An introducer 380 is connected to baseplate component 20. Baseplate component 20 and stem trial 21 are inserted into the intramedullary canal and introducer 380 is impacted to seat distal surface 33 of tray portion 30 against the proximal resected surface of tibia 410 (see FIG. 15G). Rotational alignment of baseplate component 20 is verified by connecting alignment handle 90 to tray portion 30 so that cylindrical projection 98 is received in anterior opening 36 and stabilizing flanges 96 rest on proximal plate surface 32 (see FIG. 15H). An extramedullary rod 340 connected to handle 90 is observed relative to an axis of tibia 410 and adjustments are made when necessary.

Once alignment and rotation of baseplate component 20 is verified, a keel punch 390 is inserted through keel slots 38 of baseplate component 20 and impacted so as to form spaces in tibia 410 for keel trial 80 (see FIG. 15I). Thereafter, keel trial 80 is assembled to baseplate component 20 by inserting keel portions 82 through keel slots 38 and positioning bridge on proximal plate surface 32 between keel slots 38 (see FIG. 15J).

Thereafter, tibial insert 60 is mounted onto plate portion 30 and keel trial 80. Bearing plate 70 is engaged to axle component 40 by engaging a first pair of grooves 56 with flanges 76 of bearing plate 70. Boss 50 of axle component 40 is inserted into boss opening 28 of baseplate component 20 until shoulder 55 comes to rest on shelf 26, and/or until bearing component 70 rests on tibial insert 60.

Once femur 420 is prepared for femoral trial assembly 14, femoral trial assembly 14 is mounted to the distal femur (see FIG. 15K). In this regard, an appropriate valgus adaptor 150 is selected depending on the desired valgus angle. Valgus adaptor 150 is then connected to femoral component 100 by inserting post 158 into post opening 114 until locking pawl 152 latches to latch opening 116. A stem trial 170 is connected to valgus adaptor 150 via internal threads 151. Also, distalizing screws 160 are inserted into respective threaded openings 123 in condylar portions 122. It is noted that femoral component 100 does not include augment trials 140 for this method involving a revision femur. Once femoral trial assembly 14 is assembled, stem 170 is inserted into femur 420 and femoral component 100 may be mounted to the distal femur so that first bone contact surface 101 contacts posterior resected surface 425. However, in many cases, first bone contact surface 101 may not contact posterior resected surface 425 due to posterior bone loss. In addition, second bone contact surface 102 contacts distal resected surface 423, and third bone contact surface 103 contacts anterior resected surface 421. Anterior chamfer and posterior chamfer resected surfaces 422, 424 may not be contacted or contacted in any significant way.

After the tibial trial assembly 12 is mounted to tibia 410, and femoral trial assembly 14 is mounted to femur 420, tibial trial assembly 12 and femoral trial assembly 14 are connected (see FIG. 15L). In this regard, axle 46 is inserted into recess 115 of femoral component 100 between condylar portions 122. Locking shuttle 130 is moved into its posterior position to lock axle 46 into place.

Once assemblies are connected, joint kinematics and joint alignment is assessed. In particular, the patient's patella is observed relative to femoral component 100 to assess for patella baja or patella alta conditions. In the event of a patella baja condition, femoral component 100 can be adjusted distally to align femoral component 100 with the patella. This is achieved by turning distalizing screws 160 with a wrench 400 which causes screws 160 to push against distal resected surface 423 so as to distract femoral component 100 relative to femur 420 (see FIG. 15M). Once the desired alignment of femoral component 100 relative to the patella is achieved, a pin 352 is inserted into bone through pin slot 128, which constrains femoral component 100 in a proximal-distal direction while allowing for internal/external rotation thereof. Internal/external rotation of femoral component 100 may be assessed relative to a bony landmark. Once rotational alignment is achieved, a pin 352 is inserted through one or more pinholes 129 to completely constrain femoral component 100 relative to femur 420.

Kinematic assessment of the joint is continued by rotating tibia 410 relative to femur 420 through flexion and extension to assess tightness or instability of the joint. Where more tension in the joint is desirable, the knee is flexed to about 90 degrees of flexion. Tibial insert 60 and bearing plate 70 are preferably removed. Although in some embodiments, they may remain in place. Wrench 400, which has a threaded distal end 404, is inserted into tool opening 53 of axle component 40 so that threads 404 engage internal threads 51 of axle boss 50 (see FIG. 15N). Wrench 400 is turned clockwise which causes wrench 400 to advance distally until it contacts a proximal end of stem trial 21 which resists the wrench's advancement causing axle component 40 to be advanced proximally relative to baseplate component 20 which distracts assemblies 12 and 14. This is performed until bearing component 70 can be engaged to a second pair of grooves 56 and while axle 46 remains disposed within bearing recess 115. In this regard, bearing plate 70 is engaged to a second pair of grooves 56 located more distal than the first pair of grooves 56 and insert 60 is mounted back onto tray portion 30. Wrench 400 is removed from axle component 40 and bearing component 70 is allowed to once again contact insert 60. At this point, femoral trial assembly 14 is more distant from tibial trial assembly 12 than when bearing plate 70 was engaged to the first pair of grooves 56. Joint kinematics are re-evaluated and the distance between assemblies 12 and 14 is adjusted again as necessary. Once the appropriate separation between assemblies 12 and 14 is achieved, the operator reads indicia 58 through viewing notch 71 which indicates to the operator the appropriate sized insert 60 for use in the final hinge knee prosthesis.

Once the joint kinematics and alignment are as desired, distalizing screws 160 are removed from femoral component 100. A bone saw is then used to resect femur 420 along second and third planes 125b-c which converts distal femur 100 from a five-cut femur to a three-cut femur capable of receiving a hinge knee prosthesis. A bone saw may optionally be used to perform an augment cut along first resection plane 125a to account for bone deformities in the distal femur. Thereafter, assemblies 12 and 14 are removed from their respective bones and the hinge knee prosthesis is implanted. This method is particularly beneficial at least because it allows an operator to assess joint kinematics and adjust assemblies 12 and 14 to determine the proper alignment and proper tibial insert size for the final prosthesis before resecting the femur. In addition, kinematic assessment and adjustments may be performed without disassembling assemblies 12 and 14.

FIGS. 16A-16H illustrate another method embodiment in which tibial trial assembly 12 and femoral oncology trial 200 are utilized to prepare a tibia 510 and femur 520 for a final prosthesis. In this regard, tibia 510 may be pristine or otherwise in its natural condition, while femur 520 includes a cancerous growth 522 at its distal end. In the method, a distal femoral template 600 is used to reference the joint line and mark a location for resection that ensures complete removal of the cancerous growth 522 (see FIG. 16A). Rotational alignment is also marked on the femoral shaft (see FIG. 16B). Reference measurements may also be made that can be later verified to help ensure leg length is restored (see FIG. 16C).

Figure 16C:
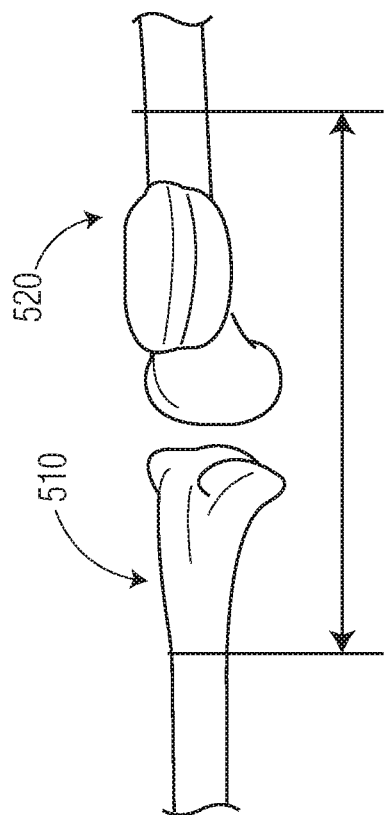
FIGS. 16A-16H depict a method of preparing a femur and tibia for a hinge knee prosthesis in an oncology procedure involving a cancerous femur.
Figure 16B:
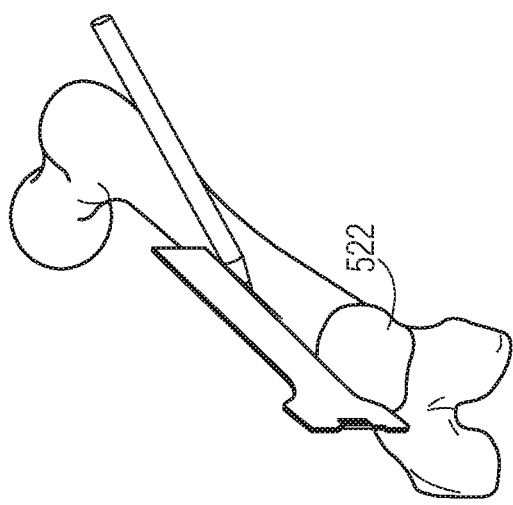
Figure 16A:
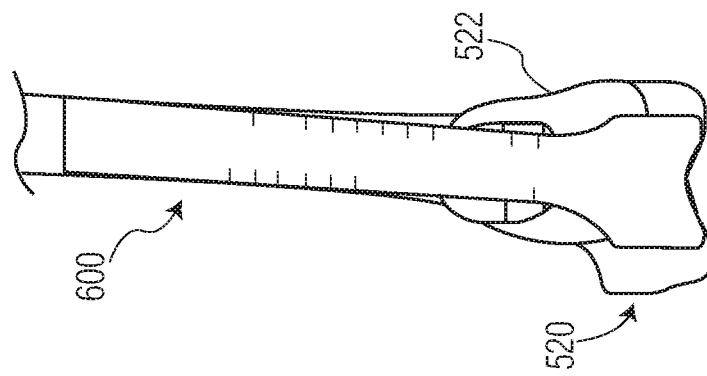
Figure 16D:
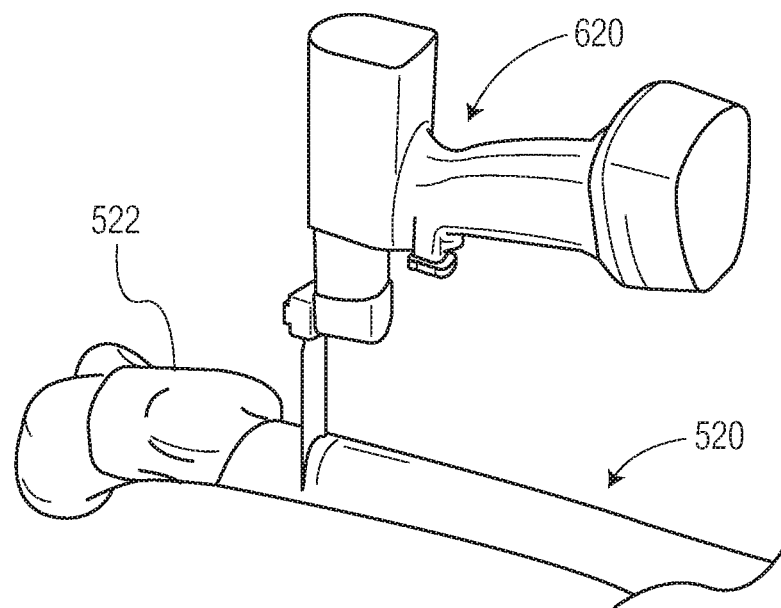
Figure 16E:
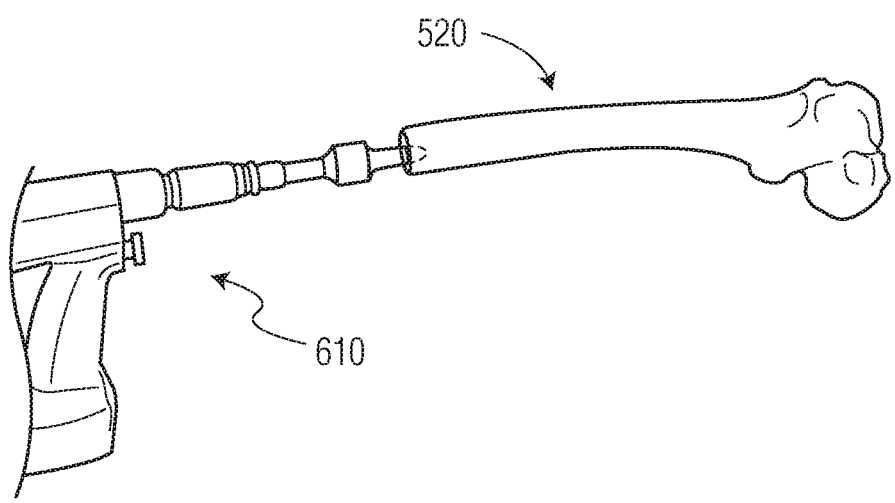
Figure 16F:
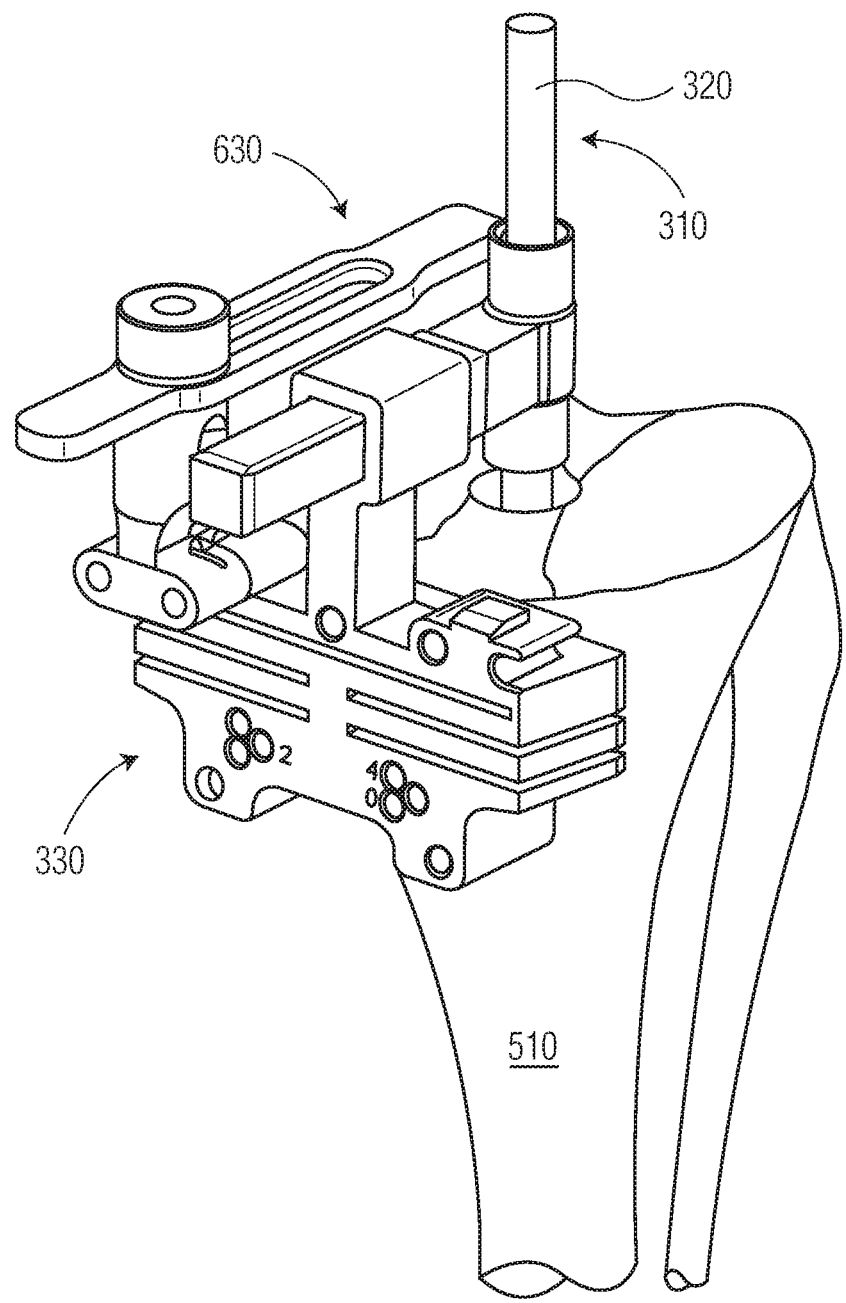
Figure 16G:
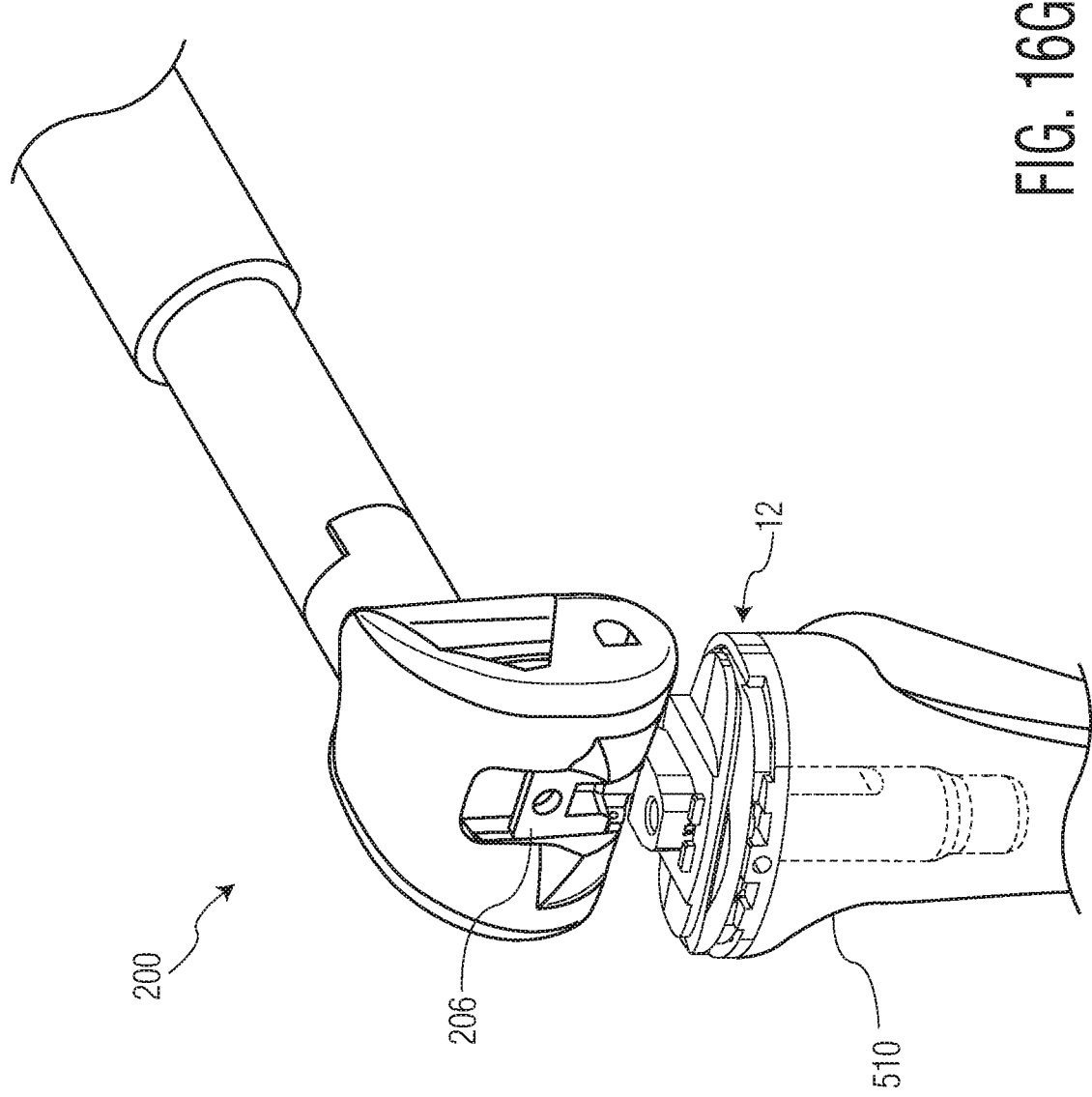
Figure 16H:
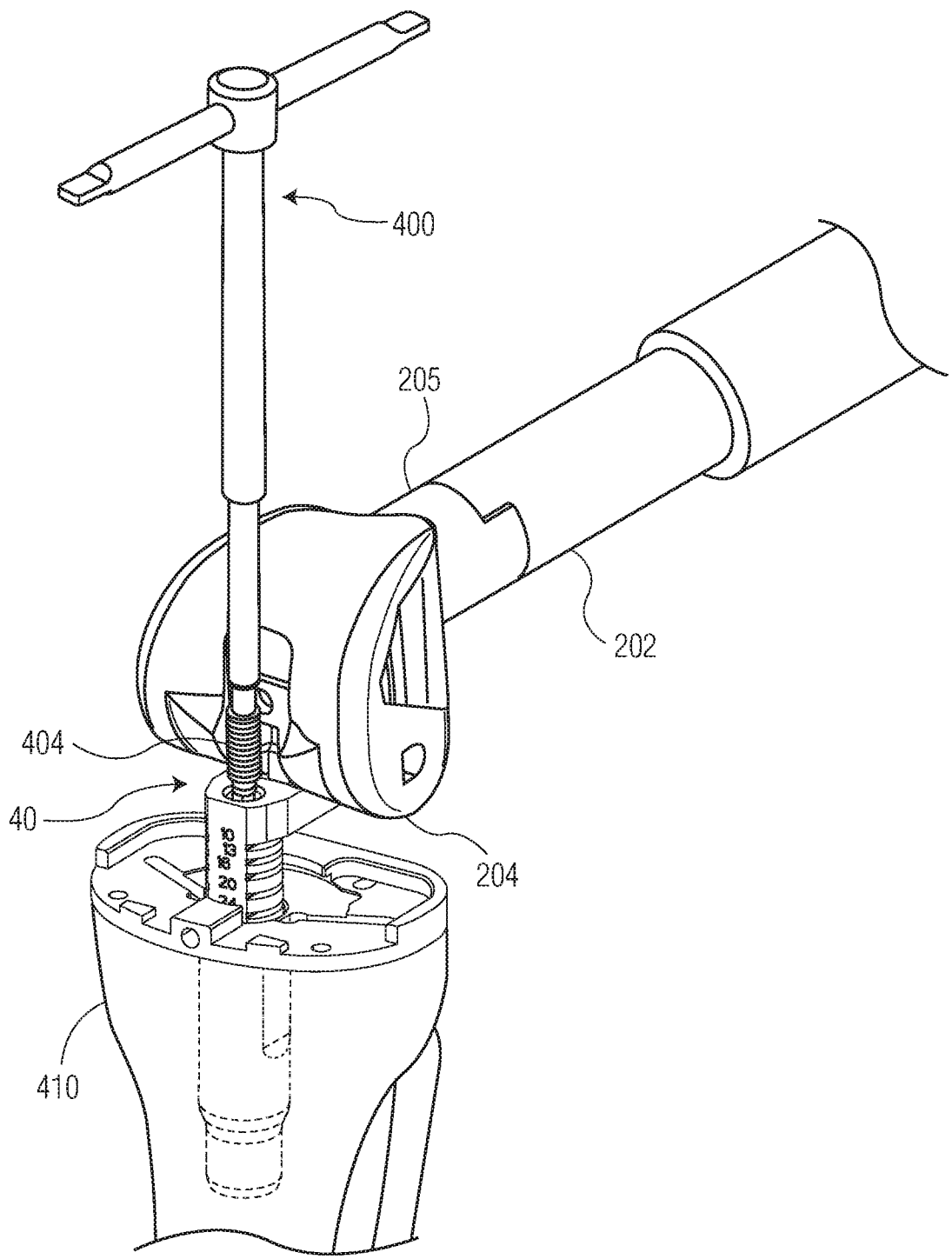

After the appropriate markings and measurements are completed, a femoral osteotomy is performed by resecting via bone saw 620 along the femoral diaphysis perpendicular to the femoral shaft axis (see FIG. 16D). A reamer 610 is then used to ream the intramedullary canal and to plane the osteotomy site so as to ensure accurate seating of femoral oncology trial 200 and the final prosthesis (see FIG. 16E).

As mentioned, tibia 510 may be pristine and is, therefore, resected to prepare tibia 510 for tibial trial assembly 12. In this regard, fluted reamers are sequentially advanced into the intramedullary canal of the tibia leaving the last reamer 310 in situ so that the shank 320 of reamer 310 extends from the proximal tibia. Resection jig 330 is connected to reamer shank 320 and a stylus 630 is connected to resection jig 330 so that stylus 630 contacts the proximal tibia as reference (see FIG. 16F). Rotational alignment of resection jig 330 may be assessed via alignment handle 90 as previously described. Jig 330 is then pinned to the proximal tibia. A bone saw is advanced through a resection slot to resect tibia 510 and form a resected proximal surface. Resection jig 330 is then removed and a boss reamer is used to further ream the proximal tibia. Reamer 310 is then removed from tibia 510.

Once tibia 510 is prepared for tibial trial assembly 12, tibial trial assembly 12 is assembled and mounted to tibia 510 as described above with regard to the revision method. Femoral oncology trial 200 is also assembled by attaching appropriate diaphyseal extensions 202, as necessary, to diaphyseal portion 205 of distal femoral component 204. Femoral oncology trial 200 is mounted onto femur 520. Thereafter, tibial trial assembly 12 and femoral oncology trial 200 are connected. In this regard, axle 46 is inserted into a bearing recess of distal femoral component 204 between condylar portions 201. Locking shuttle 206 is moved into a posterior position to lock axle 46 into place (see FIG. 16G).

Patella tracking and overall joint kinematics is evaluated by rotating tibial assembly 12 relative to femoral oncology trial 200 and about axle 46. If more distance between assemblies 12 and 200 is required, the knee is flexed to about 90 degrees and tibial insert 60 is removed from tray portion 20 and bearing component 70 is disengaged from a first pair of grooves 56. Threaded wrench 400 is inserted into the axle so as to engage internal threads 51 (see FIG. 16H). Wrench 400 is turned clockwise which distracts tibial trial assembly 12 and femoral trial assembly 200. This is performed until bearing component 70 can be engaged to a second pair of grooves 56 and while axle 46 remains disposed within the bearing recess of distal femoral component 204. In this regard, bearing component 70 is engaged to a second pair of grooves 56 located more distal than the first pair of grooves 56 and insert 60 is mounted back onto tray portion 30. Wrench 400 is removed from axle component 40 and bearing component 70 is allowed to once again contact insert 60. At this point, femoral oncology trial 200 is more distant from tibial trial assembly 12 than when bearing component 70 was engaged to the first pair of grooves 56. Joint kinematics are re-evaluated and the distance between assemblies 12 and 200 is adjusted again as necessary. Once the appropriate separation between assemblies 12 and 200 is achieved, the operator reads indicia 58 through viewing notch 71 which indicates to the operator the appropriate sized tibial insert for use in the final hinge knee prosthesis. The assemblies 12 and 200 are then disassembled and the final hinge knee prosthesis is implanted.

FIGS. 17A-17J illustrate a further method embodiment in which tibial oncology trial 220 and femoral trial assembly 14 are utilized to prepare a tibia 710 and femur 720 for a final prosthesis. In this regard, femur 720 may be pristine or otherwise in its natural condition, while tibia 710 includes a cancerous growth 722 at its proximal end. In the method, reference measurements may be made that can be later verified to help ensure leg length is restored (see FIG. 17A). A tibial template 700 is then used to reference the joint line and mark a location for resection that ensures complete removal of the cancerous growth (see FIG. 17B).

After the appropriate markings and measurements are performed, a tibial osteotomy is performed by resecting via a bone saw 620 along the diaphysis of tibia 710 perpendicular to the tibial shaft axis (see FIG. 17C). A reamer is then used to ream the intramedullary canal of tibia 710 and to plane the osteotomy site so as to ensure accurate seating of tibial oncology trial 220 and the final prosthesis.

As mentioned, femur 720 may be pristine and is, therefore, resected to prepare femur 720 for femoral trial assembly 14. In this regard, fluted reamers are sequentially advanced into the intramedullary canal of femur 720 leaving the last reamer 310 in situ so that the shank 320 of reamer 310 extends from the distal femur. A boss reamer 372 further reams femur 720 over shank 320 of reamer 310 (see FIG. 17D). A distal referencing guide 335 and resection jig 330 are connected to reamer shank 320. Once varus-valgus and internal-external rotational alignment is achieved, jig 330 is pinned to femur 420 via pins 350 and a bone saw 360 is advanced through jig 330 to resect the distal femur and form a distal resected surface (see FIG. 17E). Resection jig 330, distal referencing guide 335 and reamer 310 are then removed from femur 420.

Thereafter, a 3-in-1 cutting block 250 is connected to valgus adaptor 150. In this regard, 3-in-1 cutting block 250 has an adaptor connection member at a proximal side thereof that is similar to adaptor connection member 112. Valgus adaptor 150 is connected to such adaptor connection member as described above with relation to connection member 112. A trial stem 170 is threaded to valgus adaptor 150. Trial stem 170 and adaptor 150 are inserted into femur 720 until cutting block 250 contacts the distal resected surface (see FIG. 17F). Thereafter block 250 is pinned via pin 350 and a saw 360 is advanced through resection slots in cutting block 250 to perform an anterior skim cut, anterior chamfer cut, and a posterior chamfer cut.

Once femur 720 is resected, femur 720 is prepared for a hinge knee prosthesis. Femoral trial assembly 14 is assembled by connecting valgus adaptor 150 and stem trial 170 to femoral component 100, as previously described. In addition, since femur 720 is a 3-cut femur, adaptor trials 140 are also connected to femoral component 100. This is achieved by engaging second and third resection slots 124*b-c* with corresponding flanges 141*a-b* of adaptor trials 140. Femoral trial assembly 14 is then mounted to the distal femur (see FIG. 17H).

Once tibia 710 is prepared, tibial oncology trial 220 is also assembled by attaching appropriate diaphyseal extensions 227, as necessary, to diaphyseal portion 226 of proximal tibial component 224. In addition, insert 60 is mounted to tray portion 228, bearing component 70 is engaged to axle component 40, and axle boss 50 is inserted into the proximal end of tibial oncology trial 200. Tibial oncology trial 220 is connected to tibia 710, and femoral trial assembly 14 and tibial oncology trial 220 are connected (see FIG. 17I). In this regard, axle 46 is inserted into a bearing recess 115 of femoral component 100 between condylar portions 122. Locking shuttle 130 is moved into a posterior position to lock axle 46 into place.

Patella tracking and overall joint kinematics is evaluated by rotating tibial oncology trial 220 relative to femoral trial assembly 14 and about axle 46. In this particular method, distalizing screws 160 may not be utilized as the initial resection of the distal femur should be sufficient to appropriately align femoral component 100 in a proximal-distal direction relative to the patella when femoral component 100 is mounted to the distal femur. In addition, resecting through femoral component 100 need not be performed as the appropriate resections are performed with resection jig 330 and 3-in-1 cutting block 250 and as femoral augments are likely unnecessary as femur 720 may have been pristine prior to the procedure. If necessary, further resections may be performed on tibia 710.

If more distance between assemblies is required, the knee is flexed to about 90 degrees and tibial insert 60 is removed from tray portion and bearing component 70 is disengaged from a first pair of grooves 56. Threaded wrench 400 is inserted into axle component 40 so as to engage internal threads 51 (see FIG. 17J). Wrench 400 is turned clockwise which distracts tibial oncology trial 220 and femoral trial assembly 14. This is performed until bearing component 70 can be engaged to a second pair of grooves 56 and while axle 46 remains disposed within the bearing recess 115 of femoral component 100. In this regard, bearing component 70 is engaged to a second pair of grooves 56 located more distal than the first pair of grooves 56 and insert 60 is mounted back onto tray portion 30. Wrench 400 is removed from axle component 40 and bearing component 70 is allowed to once again contact insert 60. At this point, tibial oncology trial 220 is more distant from femoral trial assembly 14 than when bearing component 70 was engaged to the first pair of grooves 56. Joint kinematics are re-evaluated and the distance between assemblies 14 and 220 is adjusted again as necessary. Once the appropriate separation between assemblies 14 and 220 is achieved, the operator reads indicia 58 through viewing notch 71 which indicates to the operator the appropriate sized tibial insert for use in the final hinge knee prosthesis. The assemblies 14 and 220 are then disassembled and the final hinge knee prosthesis is implanted.

Figure 18A:
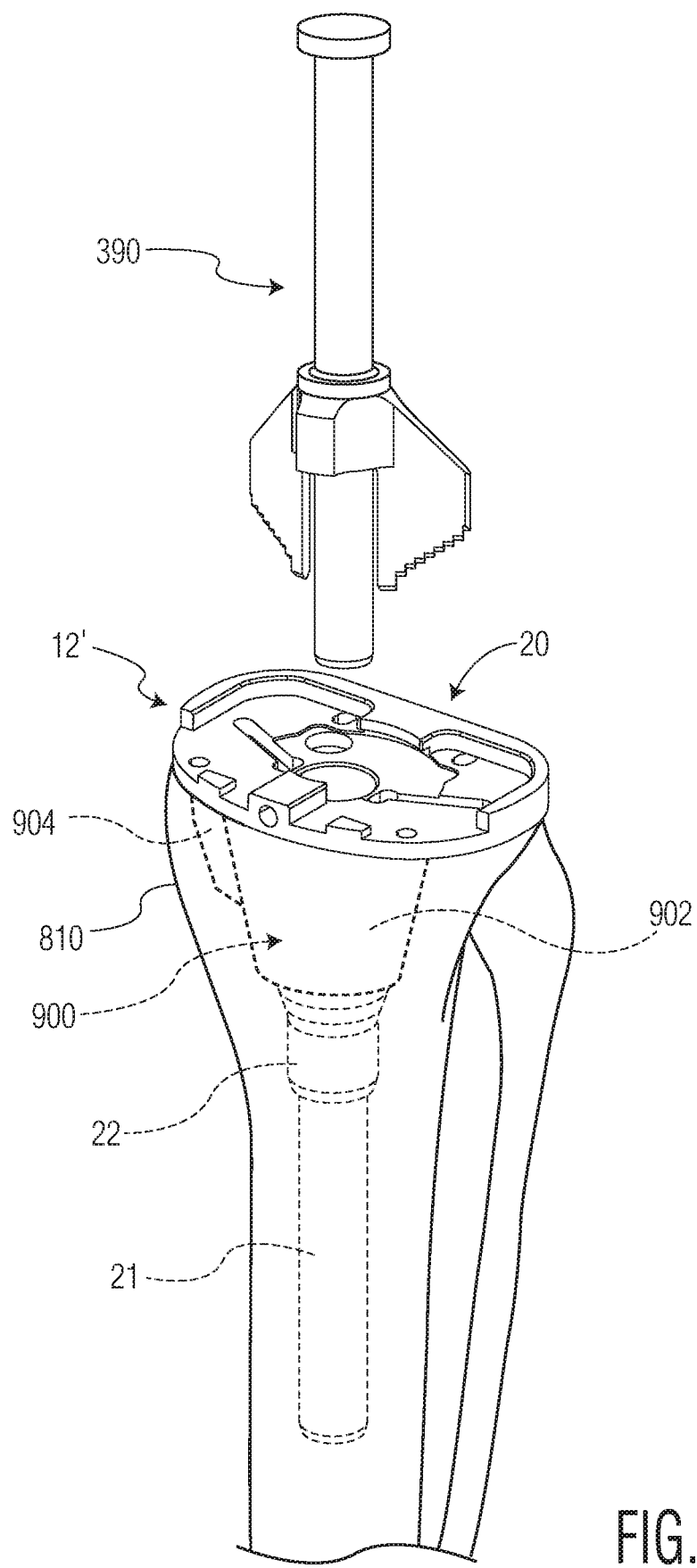
FIG. 18A depicts a method of preparing a tibia for a hinge knee prosthesis in a revision procedure according to another embodiment of the present disclosure.
Figure 18B:
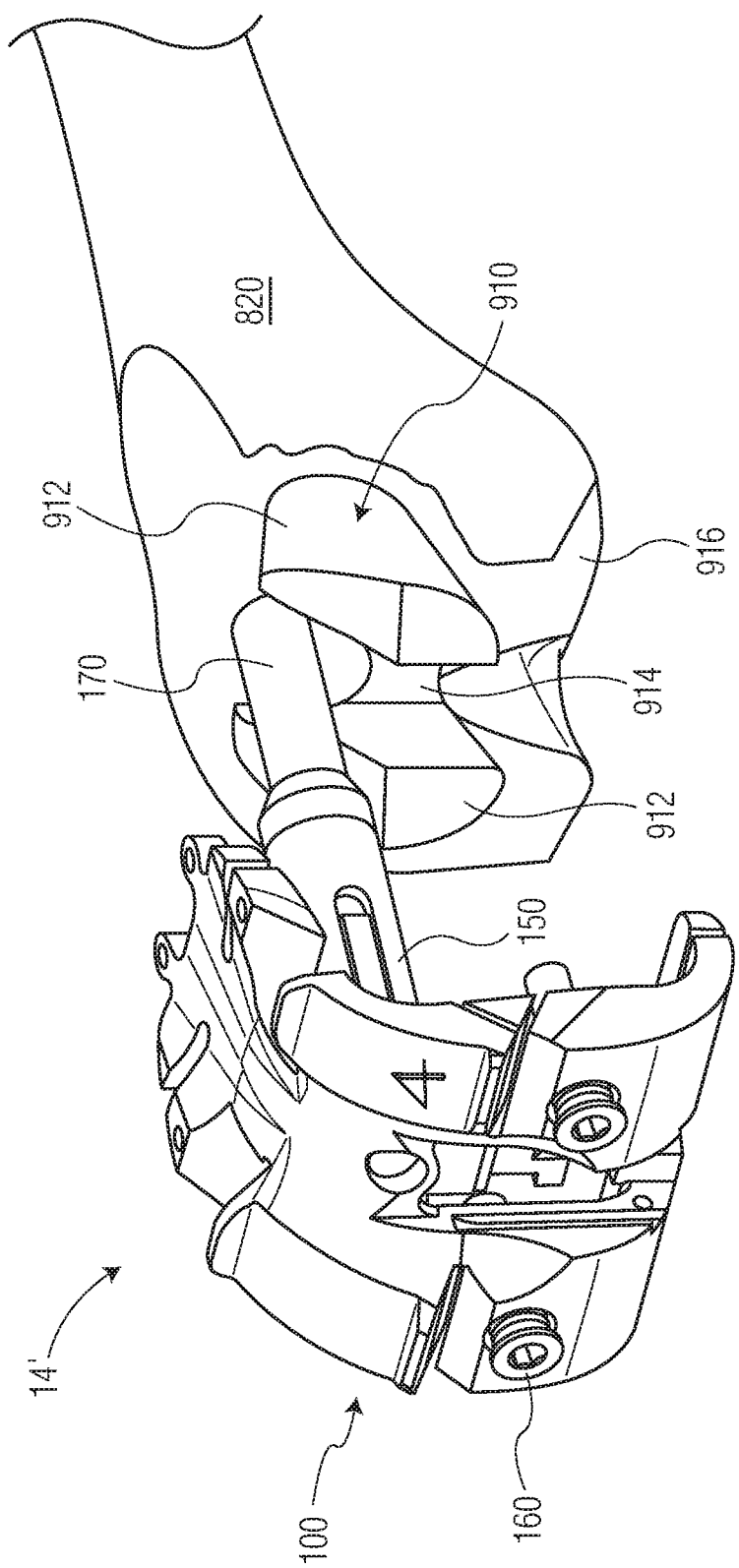
FIG. 18B depicts a method of preparing a femur for a hinge knee prosthesis in a revision procedure according to a further embodiment of the present disclosure.

FIGS. 18A and 18B illustrate further method embodiments of preparing a tibia and femur to receive a hinge knee prosthesis. In a revision procedure, bone deformities, such as bone voids, are often found in a distal femur or proximal tibia. Such deformities may make it difficult to obtain bone-to-prosthesis contact when a hinge knee prosthesis is implanted and may weaken the bone. In this regard, void filling prostheses, such as cones or sleeves, can be utilized to fill such deformities and provide structural support. Examples of such void filling prostheses are disclosed in U.S. application Ser. No. 14/992,695; U.S. Publication No. 2014/0277567; and U.S. Pat. Nos. 9,011,444 and 9,149,282, the disclosures of which are hereby incorporated by reference herein in their entireties.

As shown in FIG. 18A, an alternative tibial trial assembly 12' includes baseplate component 20, trial stem 21, and tibial void filling trial 900. Also included in trial assembly 12', but not depicted in FIG. 18A, is tibial insert 60, bearing component 70, keel trial 80 and axle component 90. Tibial void filling trial 900 mimics a tibial void filling prosthesis and includes a body 902 that has an opening extending through it in a proximal-distal direction. In addition, in the embodiment depicted, void filling trial 900 includes a lobe portion 904 connected to body 902. Lobe portion 904 may help fill lateral or medial voids that extend beyond the boundaries of body 902 when implanted.

In a method of preparing a tibia utilizing tibial trial assembly 12', a previously implanted tibial prosthesis is removed from a tibia 810, an intramedullary canal of tibia 810 is reamed and the proximal tibia is cut, as described in detail above. Further reaming is performed in the proximal tibia using void forming reaming assembles, examples of which are also described in the heretofore incorporated documents, to form a uniform void in locations where bone deformities are present. After such uniform void is formed, void filling trial 900 is inserted into the void. Trial stem 21 and baseplate component 20 are inserted into the opening of void filling trial 900 using an introducer, such as introducer 390, so that stem 21 extends through void filling prosthesis 900 and boss 22 is at least partially disposed within the opening of void filling trial 900. Thereafter, keel punch 390 is punched through keel slots 38 and through one or more slots in trial 900, and keel trial 80 is coupled to baseplate component 20 so that keel portions 82 at least partially extend into void filling trial 90 and into bone. Tibial insert 60, axle component 90, and bearing component 70 are also assembled to baseplate component 20. Once tibial trial assembly 12' is assembled and mounted to tibia 810, trial assembly 12' is connected to femoral trial assembly 14, or 14' as described below, via axle 46 of axle component 40. Joint kinematics are then assessed, and adjustments, as necessary, are performed, as previously described.

As shown in FIG. 18B, an alternative femoral trail assembly 14' includes femoral component 100, valgus adaptor 150, stem 170, and femoral void filling trial 910. Femoral void filling trial 910, as depicted, mimics a femoral void filling prosthesis and includes a central body 914 and leg members 912 connected to central body 914. An opening 916 extends through body 916 and between leg members 912.

In a method of preparing a femur utilizing femoral trial assembly 14', a previously implanted femoral prosthesis is removed from a femur 820 and an intramedullary canal of femur 820 is reamed, as described in detail above. Further reaming is performed in the distal femur using void forming reaming assembles, examples of which are described in the heretofore incorporated references, to form a uniform void in locations where bone deformities are present. After such uniform void is formed, femoral void filling trial 910 is inserted into the void. Trial stem 170 and valgus adaptor 150 are inserted into opening 916 of femoral void filling trial 910 so that stem 170 extends through void filling prosthesis 910 and valgus adaptor 150 is at least partially disposed within opening 916 of femoral void filling trial 910. Once femoral trial assembly 14' is mounted to femur 820, femoral trial assembly 14' is connected to tibial trial assembly 12 or 12' via axle component 40. Joint kinematics are assessed, and adjustments, such as via distalizing screws 160, are performed, as previously described.

Although hinge knee trial assembly 10 has been described as a trial, it is also contemplated that certain aspects of assembly 10 can be implemented in a final prosthesis, such as axle 46 and its connection to femoral component 100. In addition, various alternatives are contemplated. For example, hinge knee trial assembly 10 may not include bearing plate 70. Instead condylar portions of the femoral component 122 may directly contact proximally facing bearing surfaces 64 of insert 60. In such embodiment, tibial inserts, like insert 60, of varying thickness may be attached to baseplate component 20 in lieu of bearing plate 70 to adjust the distance between the femoral trial assembly 14 and the tibial trial assembly while axle 46 is connected to femoral component 100.

Moreover, it was discussed that tibial trial assembly 12 and femoral trial assembly 14 may be utilized in a revision procedure, tibial trial assembly 12 and femoral oncology trial 200 may be utilized in a femoral oncology procedure, and femoral trial assembly 14 and tibial oncology trial 220 may be utilized in a tibial oncology procedure. However, it is also contemplated that femoral oncology trial 200 and tibial oncology trial 220 may be utilized in the same procedure where both a femur and tibia include cancerous growths.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A knee arthroplasty system, comprising:
    a femoral component having a first side and a second side, the first side defining first and second condylar portions, the second side having an adaptor connection member;
    a valgus adaptor having a first member, a second member, and a locking pawl, the first member and locking pawl being configured to releasably engage the adaptor connection member of the femoral component to selectively secure it thereto, wherein the second member has a slot extending along its side and wherein the locking pawl is partially disposed and moveable within said slot; and
    a stem having a distal end configured to be received within an intramedullary canal of a femur and a proximal end configured to engage the second member of the valgus adaptor to secure it thereto.

2. The system of claim 1, wherein the adaptor connection member comprises a sidewall and the valgus adaptor comprises a flat surface corresponding to the sidewall such that, when the first member is engaged to the adaptor connection member, the sidewall engages the flat surface to prevent rotation of the valgus adaptor relative to the femoral component.

3. The system of claim 2, wherein the adaptor connection member comprises a latch opening.

4. The system of claim 3, wherein the locking pawl is rotatably coupled to the second member of the valgus adaptor and is configured to releasably engage with the latch opening.

5. The system of claim 1, wherein the first and second members each define a longitudinal axis, the longitudinal axes of the first and second members being at an oblique angle relative to each other.

6. The system of claim 5, wherein the oblique angle is 6 degrees.

7. The system of claim 1, wherein the first and second members are each cylindrical, the first member having a smaller cross-sectional dimension than the second member of the valgus adaptor.

8. The system of claim 7, wherein the second member of the valgus adaptor includes an opening extending therein.

9. The system of claim 7, wherein the adaptor connection member defines an opening configured to receive the first member of the valgus adaptor therein.

10. The system of claim 1, wherein the femoral component is a cutting guide having the adaptor connection member at a proximal side thereof, the first member and the locking pawl being configured to releasably engage the adaptor connection member of the cutting guide.

11. A knee arthroplasty system, comprising:
    a femoral cutting guide having first and second sides and first guide slot extending through the first and second sides, the second side having an adaptor connection member extending therefrom;
    a valgus stem adaptor having first and second members and a locking pawl, the first member and locking pawl being configured to selectively engage the adaptor connection member, wherein the second member has a slot extending along its side and wherein the locking pawl is partially disposed and moveable within said slot; and
    a stem having a distal end configured to be received within an intramedullary canal of a femur and a proximal end configured to engage the second member of the valgus adaptor to secure it thereto.

12. The system of claim 11, wherein the femoral cutting guide has a planar bone contact surface and a second guide slot, the first and second guide slots extending through the planar bone contact surface.

13. The system of claim 11, further comprising an augment trial having a body, the body configured to attach to the second side of the femoral cutting guide.

14. The system of claim 13, wherein the augment trial comprises at least one slot, said at least one slot aligning with the first guide slot when the augment trial is attached to the femoral cutting guide.

15. The system of claim 14, wherein the femoral cutting guide includes a second guide slot and the augment trial comprises a first flange configured to engage with the second guide slot of the femoral cutting guide.

16. The system of claim 15, wherein the augment trial further comprises a spring member having a curved edge wherein the curved edge conforms to a curved surface of the femoral component and is adapted to provide resistance to hold the augment trial in place.

17. The system of claim 13, wherein the first side of the femoral cutting guide includes first and second condylar portions, and the second side of the femoral cutting guide includes first and second surfaces and a curved surface connecting the first and second surfaces.

* * * * *